US010888280B2

(12) United States Patent
Newberry

(10) Patent No.: US 10,888,280 B2
(45) Date of Patent: *Jan. 12, 2021

(54) SYSTEM AND METHOD FOR OBTAINING HEALTH DATA USING A NEURAL NETWORK

(71) Applicant: Sanmina Corporation, San Jose, CA (US)

(72) Inventor: Robert Steven Newberry, New Hope, AL (US)

(73) Assignee: Sanmina Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/898,580

(22) Filed: Feb. 17, 2018

(65) Prior Publication Data
US 2018/0214088 A1    Aug. 2, 2018

Related U.S. Application Data

(63) Continuation-in-part of application No. 15/867,632, filed on Jan. 10, 2018, now Pat. No. 10,039,500, and
(Continued)

(51) Int. Cl.
*A61B 5/00* (2006.01)
*A61B 5/024* (2006.01)
(Continued)

(52) U.S. Cl.
CPC ........ *A61B 5/7264* (2013.01); *A61B 5/02416* (2013.01); *A61B 5/6817* (2013.01);
(Continued)

(58) Field of Classification Search
None
See application file for complete search history.

(56) References Cited

U.S. PATENT DOCUMENTS 4,913,150 A    4/1990    Cheung et al.
5,115,133 A    5/1992    Knudson
(Continued)

FOREIGN PATENT DOCUMENTS

CN    102609627 A    7/2012
EP    2544124 A1 *   1/2013    ........... A61B 5/1455
(Continued)

OTHER PUBLICATIONS

Neural network for photoplethysmographic respiratory rate monitoring. (Med Biol Eng Comput. May 2003;41(3):242-8., <https://www.ncbi.nlm.nih.gov/pubmed/12803287>, accessed Aug. 27, 2018.*
(Continued)

*Primary Examiner* — Christopher Koharski
*Assistant Examiner* — James Moss
(74) *Attorney, Agent, or Firm* — Loza & Loza, LLP; Jessica Smith

(57) ABSTRACT

A photoplethysmography (PPG) circuit or non-contact camera obtains PPG signals at a plurality of wavelengths. A signal processing module obtains at least a first spectral response around a first wavelength and a second spectral response around a second wavelength. The signal processing device generates PPG input data using the PPG signals, wherein the PPG input data includes one or more parameters obtained from each of the first spectral response and the second spectral response. A neural network processing device generates an input vector including the PPG input data and determines an output vector including health data, wherein the health data includes for example, an oxygen saturation level, a glucose level or a blood alcohol level.

24 Claims, 28 Drawing Sheets

Related U.S. Application Data a continuation-in-part of application No. 15/859,147, filed on Dec. 29, 2017, now Pat. No. 10,194,871, and a continuation-in-part of application No. 15/811,479, filed on Nov. 13, 2017, now Pat. No. 10,238,346, and a continuation-in-part of application No. 15/804,581, filed on Nov. 6, 2017, now Pat. No. 10,231,674, and a continuation-in-part of application No. 15/718,721, filed on Sep. 28, 2017, now Pat. No. 10,517,515, and a continuation-in-part of application No. 15/680,991, filed on Aug. 18, 2017, now Pat. No. 9,968,289, said application No. 15/718,721 is a continuation of application No. 15/622,941, filed on Jun. 14, 2017, now Pat. No. 9,788,767, application No. 15/898,580, which is a continuation-in-part of application No. 15/490,813, filed on Apr. 18, 2017, now Pat. No. 9,980,676, and a continuation-in-part of application No. 15/489,391, filed on Apr. 17, 2017, now Pat. No. 9,974,451, and a continuation-in-part of application No. 15/485,816, filed on Apr. 12, 2017, now Pat. No. 10,155,087, and a continuation-in-part of application No. 15/462,700, filed on Mar. 17, 2017, now Pat. No. 10,500,354, said application No. 15/804,581 is a continuation of application No. 15/404,117, filed on Jan. 11, 2017, application No. 15/898,580, which is a continuation-in-part of application No. 15/400,916, filed on Jan. 6, 2017, now Pat. No. 10,750,981, which is a continuation of application No. 15/276,760, filed on Sep. 26, 2016, now Pat. No. 9,636,457, said application No. 15/489,391 is a continuation of application No. 15/275,444, filed on Sep. 25, 2016, now Pat. No. 9,642,538, said application No. 15/490,813 is a continuation of application No. 15/275,388, filed on Sep. 24, 2016, now Pat. No. 9,642,578.

(60) Provisional application No. 62/613,388, filed on Jan. 3, 2018, provisional application No. 62/463,104, filed on Feb. 24, 2017, provisional application No. 62/457,138, filed on Feb. 9, 2017.

(51) Int. Cl.
*A61B 5/1455* (2006.01)
*A61B 5/145* (2006.01)
*A61B 5/08* (2006.01)

(52) U.S. Cl.
CPC ............ *A61B 5/7275* (2013.01); *A61B 5/743* (2013.01); *A61B 5/0002* (2013.01); *A61B 5/0022* (2013.01); *A61B 5/0077* (2013.01); *A61B 5/024* (2013.01); *A61B 5/0816* (2013.01); *A61B 5/1455* (2013.01); *A61B 5/14532* (2013.01); *A61B 5/14551* (2013.01); *A61B 5/6826* (2013.01); *A61B 5/7225* (2013.01); *A61B 2560/0223* (2013.01)

(56) References Cited

U.S. PATENT DOCUMENTS

| | | | |
|---|---|---|---|
| 5,269,310 A | 12/1993 | Jones et al. | |
| 5,358,703 A | 10/1994 | Lai | |
| 5,515,847 A | 5/1996 | Braig et al. | |
| 5,553,616 A | 9/1996 | Ham et al. | |
| 5,673,692 A | 10/1997 | Schulze et al. | |
| 5,823,966 A | 10/1998 | Buchert | |
| 5,947,911 A | 9/1999 | Wong et al. | |
| 5,983,121 A | 11/1999 | Tsuchiya | |
| 6,087,087 A | 7/2000 | Yonetani et al. | |
| 6,280,390 B1 | 8/2001 | Akselrod et al. | |
| 6,285,896 B1 | 9/2001 | Tobler et al. | |
| 6,305,804 B1 | 10/2001 | Rice et al. | |
| 6,537,225 B1 | 3/2003 | Mills | |
| 6,694,180 B1 | 2/2004 | Boesen | |
| 6,719,705 B2 | 4/2004 | Mills | |
| 6,819,950 B2 | 11/2004 | Mills | |
| 6,921,367 B2 | 7/2005 | Mills | |
| 6,985,763 B2 | 1/2006 | Boas et al. | |
| 7,154,592 B2 | 12/2006 | Reynolds et al. | |
| 7,167,736 B2 | 1/2007 | Winther | |
| 7,171,251 B2 | 1/2007 | Sarussi et al. | |
| 7,179,228 B2 | 2/2007 | Banet | |
| 7,209,775 B2 | 4/2007 | Bae et al. | |
| 7,291,497 B2 | 11/2007 | Holmes et al. | |
| 7,371,562 B2 | 5/2008 | Cunningham et al. | |
| 7,608,045 B2 | 10/2009 | Mills | |
| 7,647,083 B2 | 1/2010 | Al-Ali et al. | |
| 7,761,127 B2 | 7/2010 | Al-Ali et al. | |
| 7,763,472 B2 | 7/2010 | Doctor et al. | |
| 7,764,982 B2 | 7/2010 | Dalke et al. | |
| 7,941,199 B2 | 5/2011 | Kiani | |
| 8,172,459 B2 * | 5/2012 | Abreu | A61B 5/0002 374/208 |
| 8,224,411 B2 | 7/2012 | Al-Ali et al. | |
| 8,255,027 B2 | 8/2012 | Al-Ali et al. | |
| 8,328,420 B2 | 12/2012 | Abreu | |
| 8,385,996 B2 | 2/2013 | Smith et al. | |
| 8,401,605 B2 | 3/2013 | Huiku | |
| 8,483,787 B2 | 7/2013 | Al-Ali et al. | |
| 8,494,507 B1 | 7/2013 | Tedesco et al. | |
| 8,597,274 B2 | 12/2013 | Sloan et al. | |
| 8,652,040 B2 | 2/2014 | Leboeuf et al. | |
| 8,676,284 B2 | 3/2014 | He | |
| 8,730,047 B2 | 5/2014 | Ridder et al. | |
| 8,868,149 B2 | 10/2014 | Eisen et al. | |
| 8,888,701 B2 | 11/2014 | Leboeuf et al. | |
| 8,906,693 B2 | 12/2014 | Schultz et al. | |
| 8,923,918 B2 | 12/2014 | Kreger et al. | |
| 8,961,932 B2 | 2/2015 | Silverman | |
| 9,022,973 B2 | 5/2015 | Sexton et al. | |
| 9,131,882 B2 | 9/2015 | Al-Ali et al. | |
| 9,149,216 B2 | 10/2015 | Eisen et al. | |
| 9,149,646 B2 | 10/2015 | Keswarpu et al. | |
| 9,387,033 B2 | 7/2016 | Yodfat et al. | |
| 9,442,092 B2 | 9/2016 | Lane | |
| 9,521,970 B2 | 12/2016 | Hoppe et al. | |
| 9,554,738 B1 | 1/2017 | Gulati et al. | |
| 9,636,457 B2 * | 5/2017 | Newberry | A61M 5/1723 |
| 9,642,538 B2 * | 5/2017 | Newberry | A61B 5/02055 |
| 9,642,578 B2 * | 5/2017 | Newberry | A61B 5/7275 |
| 9,668,701 B2 | 6/2017 | Maarek | |
| 9,713,428 B2 | 7/2017 | Chon et al. | |
| 9,739,663 B2 | 8/2017 | Halder et al. | |
| 9,820,656 B2 | 11/2017 | Olivier | |
| 9,839,381 B1 | 12/2017 | Weber et al. | |
| 9,924,895 B2 | 3/2018 | Rawicz et al. | |
| 9,949,675 B2 | 4/2018 | Miller | |
| 9,999,355 B2 | 6/2018 | Kirenko | |
| 10,028,682 B2 | 7/2018 | Thiele | |
| D824,937 S | 8/2018 | Sparandara et al. | |
| 10,099,554 B2 | 10/2018 | Steeg et al. | |
| 10,130,285 B1 | 11/2018 | Singamsetty et al. | |
| 10,153,796 B2 | 12/2018 | Fung et al. | |
| 10,181,021 B2 | 1/2019 | Venkatraman et al. | |
| 10,206,619 B1 | 2/2019 | Lee et al. | |
| 10,215,698 B2 | 2/2019 | Han et al. | |
| 10,227,063 B2 | 3/2019 | Abreu | |
| 10,232,156 B2 | 3/2019 | Netzel et al. | |
| 10,278,591 B2 | 5/2019 | Gil | |
| D850,316 S | 6/2019 | Ennis et al. | |
| 10,314,500 B2 | 6/2019 | Olivier | |
| 10,322,728 B1 | 6/2019 | Porikli et al. | |
| 10,342,495 B2 | 7/2019 | Melkoniemi et al. | |
| 10,349,847 B2 | 7/2019 | Kwon et al. | |
| 10,420,470 B2 | 9/2019 | Kwon et al. | |
| 10,420,491 B2 | 9/2019 | Rajan et al. | |
| 10,433,726 B2 | 10/2019 | Ramesh et al. | |
| 10,433,738 B2 | 10/2019 | Thomas et al. | |
| 10,433,739 B2 | 10/2019 | Weekly et al. | |

(56) References Cited

U.S. PATENT DOCUMENTS

| | | |
|---|---|---|
| 10,463,283 B2 | 11/2019 | Ferber et al. |
| 2002/0049389 A1 | 4/2002 | Abreu |
| 2003/0229276 A1* | 12/2003 | Sarussi .............. A61B 5/02433 600/322 |
| 2004/0078219 A1 | 4/2004 | Kaylor et al. |
| 2004/0100376 A1 | 5/2004 | Lye et al. |
| 2004/0157341 A1 | 8/2004 | Reynolds et al. |
| 2005/0010090 A1* | 1/2005 | Acosta ................ A61B 5/0075 600/316 |
| 2005/0043894 A1 | 2/2005 | Fernandez |
| 2005/0049470 A1 | 3/2005 | Terry |
| 2005/0101841 A9 | 5/2005 | Kaylor et al. |
| 2005/0209516 A1 | 9/2005 | Fraden |
| 2005/0228244 A1 | 10/2005 | Banet |
| 2005/0228299 A1 | 10/2005 | Banet |
| 2005/0245831 A1 | 11/2005 | Banet |
| 2006/0009698 A1 | 1/2006 | Banet |
| 2006/0074282 A1* | 4/2006 | Ward ................... A61B 5/0071 600/310 |
| 2006/0094942 A1 | 5/2006 | Winther |
| 2006/0287589 A1 | 12/2006 | Wobermin et al. |
| 2007/0106172 A1 | 5/2007 | Abreu |
| 2007/0202605 A1 | 8/2007 | Doctor et al. |
| 2007/0203405 A1 | 8/2007 | Shimomura |
| 2007/0260132 A1 | 11/2007 | Sterling |
| 2008/0146890 A1 | 6/2008 | LeBoeuf et al. |
| 2008/0165017 A1 | 7/2008 | Schwartz |
| 2008/0208019 A1 | 8/2008 | Nitzan |
| 2008/0241199 A1 | 10/2008 | Silverman |
| 2009/0043178 A1 | 2/2009 | Belotserkovsky |
| 2009/0156988 A1 | 6/2009 | Ferren et al. |
| 2009/0187167 A1 | 7/2009 | Sexton et al. |
| 2009/0287120 A1 | 11/2009 | Ferren et al. |
| 2010/0049020 A1 | 2/2010 | Dalke et al. |
| 2010/0191080 A1 | 7/2010 | Mills |
| 2010/0274101 A1 | 10/2010 | Lin et al. |
| 2010/0274102 A1 | 10/2010 | Teixeira |
| 2010/0331631 A1 | 12/2010 | Maclaughlin |
| 2011/0071376 A1* | 3/2011 | McKenna .......... G06K 9/00557 600/336 |
| 2011/0082355 A1 | 4/2011 | Eisen et al. |
| 2011/0106050 A1 | 5/2011 | Yodfat et al. |
| 2011/0137141 A1 | 6/2011 | Razoumov et al. |
| 2011/0160697 A1 | 6/2011 | Yodfat et al. |
| 2011/0166553 A1 | 7/2011 | Holmes et al. |
| 2011/0224518 A1 | 9/2011 | Tindi et al. |
| 2011/0237464 A1 | 9/2011 | Cunningham et al. |
| 2011/0275978 A1 | 11/2011 | Hyde et al. |
| 2012/0010683 A1 | 1/2012 | Keswarpu et al. |
| 2012/0029363 A1 | 2/2012 | Lund |
| 2012/0095302 A1 | 4/2012 | Adhikari |
| 2012/0131507 A1 | 5/2012 | Sparandara et al. |
| 2012/0136054 A1 | 5/2012 | Schultz et al. |
| 2012/0156933 A1 | 6/2012 | Kreger et al. |
| 2012/0203077 A1 | 8/2012 | He et al. |
| 2012/0238844 A1 | 9/2012 | Grata et al. |
| 2012/0330126 A1 | 12/2012 | Hoppe et al. |
| 2013/0030259 A1* | 1/2013 | Thomsen ........... A61B 5/02028 600/301 |
| 2013/0060098 A1 | 3/2013 | Thomsen et al. |
| 2013/0066176 A1 | 3/2013 | Addison et al. |
| 2013/0110311 A1 | 5/2013 | Ver Steeg et al. |
| 2013/0310669 A1 | 11/2013 | Nitzan |
| 2014/0046160 A1 | 2/2014 | Terashima et al. |
| 2014/0100432 A1 | 4/2014 | Golda et al. |
| 2014/0112940 A1 | 4/2014 | Lane |
| 2014/0194342 A1 | 7/2014 | Zhang et al. |
| 2014/0243648 A1 | 8/2014 | Dubielczyk |
| 2014/0253709 A1 | 9/2014 | Bresch et al. |
| 2014/0275852 A1 | 9/2014 | Hong et al. |
| 2014/0297313 A1 | 10/2014 | Condurso et al. |
| 2014/0303454 A1 | 10/2014 | Clifton et al. |
| 2014/0316226 A1 | 10/2014 | Ferber et al. |
| 2015/0066238 A1 | 3/2015 | Todd et al. |
| 2015/0088007 A1 | 3/2015 | Bardy et al. |
| 2015/0094914 A1 | 4/2015 | Abreu |
| 2015/0105638 A1 | 4/2015 | Eisen et al. |
| 2015/0109617 A1 | 4/2015 | Gilbert et al. |
| 2015/0148622 A1 | 5/2015 | Moyer et al. |
| 2015/0148635 A1 | 5/2015 | Benaron |
| 2015/0150453 A1 | 6/2015 | Abreu |
| 2015/0182172 A1 | 7/2015 | Shelley et al. |
| 2015/0229341 A1 | 8/2015 | Fung et al. |
| 2015/0250404 A1 | 9/2015 | Maarek |
| 2015/0282747 A1 | 10/2015 | Thiele |
| 2015/0366471 A1 | 12/2015 | Leboeuf et al. |
| 2016/0004827 A1 | 1/2016 | Silva et al. |
| 2016/0018257 A1 | 1/2016 | Mirov et al. |
| 2016/0058308 A1 | 3/2016 | Robinson |
| 2016/0058347 A1 | 3/2016 | Reichgott et al. |
| 2016/0066863 A1* | 3/2016 | Thaveeprungsriporn .................... A61B 5/7235 600/323 |
| 2016/0100781 A1 | 4/2016 | Bechtel et al. |
| 2016/0135706 A1* | 5/2016 | Sullivan ............... A61B 5/0059 600/301 |
| 2016/0262707 A1 | 9/2016 | Devries |
| 2016/0367154 A1 | 12/2016 | Gladshtein et al. |
| 2017/0014035 A1 | 1/2017 | Newberry |
| 2017/0027521 A1 | 2/2017 | Geva et al. |
| 2017/0050518 A1 | 2/2017 | Steeg et al. |
| 2017/0071550 A1 | 3/2017 | Newberry |
| 2017/0091436 A1 | 3/2017 | Cao et al. |
| 2017/0172477 A1 | 6/2017 | Adusumilli et al. |
| 2017/0215811 A1 | 8/2017 | Newberry |
| 2017/0256110 A1 | 9/2017 | Divincent et al. |
| 2017/0347894 A1 | 12/2017 | Bhushan et al. |
| 2017/0347899 A1 | 12/2017 | Bhushan et al. |
| 2018/0117291 A1 | 5/2018 | Netzel et al. |
| 2018/0140210 A1 | 5/2018 | Jelfs et al. |
| 2018/0140237 A1 | 5/2018 | Rajan et al. |
| 2018/0177416 A1 | 6/2018 | Church et al. |
| 2018/0177440 A1 | 6/2018 | Jelfs et al. |
| 2018/0200433 A1 | 7/2018 | Cirit |
| 2018/0264242 A1 | 9/2018 | Hoffman et al. |
| 2018/0353137 A1 | 12/2018 | Balajadia et al. |
| 2018/0358119 A1 | 12/2018 | Bhushan et al. |
| 2019/0046039 A1 | 2/2019 | Ramesh et al. |
| 2019/0050622 A1 | 2/2019 | Cabibihan et al. |
| 2019/0086331 A1 | 3/2019 | Han |
| 2019/0099114 A1 | 4/2019 | Mouradian et al. |
| 2019/0110745 A1 | 4/2019 | Linnes et al. |
| 2019/0125963 A1 | 5/2019 | Mou et al. |
| 2019/0125964 A1 | 5/2019 | Mou et al. |
| 2019/0133471 A1 | 5/2019 | Olson et al. |
| 2019/0192085 A1 | 6/2019 | Krishna et al. |
| 2019/0192086 A1 | 6/2019 | Krishna et al. |
| 2019/0251238 A1 | 8/2019 | Venkatraman et al. |
| 2019/0358387 A1 | 11/2019 | Elbadry et al. |

FOREIGN PATENT DOCUMENTS

| | | |
|---|---|---|
| EP | 2017001250 A1 | 1/2017 |
| EP | 3488776 A1 | 5/2019 |
| WO | 2004047630 A1 | 6/2004 |
| WO | 2007013054 A1 | 2/2007 |
| WO | 2008006150 A1 | 1/2008 |
| WO | 2010128852 A3 | 11/2010 |
| WO | 2010147968 A1 | 12/2010 |
| WO | 2012108895 A1 | 8/2012 |
| WO | 2013052318 A1 | 4/2013 |
| WO | 2013127564 A1 | 9/2013 |
| WO | 2014163583 A1 | 10/2014 |
| WO | 2015143197 A1 | 9/2015 |
| WO | 2015200148 A1 | 12/2015 |
| WO | 2017001249 A1 | 1/2017 |
| WO | 2018206875 A1 | 11/2018 |

(56) References Cited

FOREIGN PATENT DOCUMENTS

WO    2019030700 A1    2/2019
WO    2019118053 A1    6/2019

OTHER PUBLICATIONS

Mohamad Soltane et al., Artificial Neural Networks (ANN) Approach to PPG Signal Classification, International Journal of Computer and Information Sciences vol. 2, No. 1, Apr. 2004, < http://www.ijcis.info/Vol2N1/58-65S.pdf >, accessed Aug. 27, 2018.*

"Visible." Merriam-Webster.com. Merriam-Webster, n.d. Web. Aug. 23, 2018.*

"Near-ultraviolet." Merriam-Webster.com. Merriam-Webster, n.d. Web. Aug. 23, 2018.*

M.S. Wróbel et al., "Non-invasive blood glucose monitoring with Raman spectroscopy: prospects for device miniaturization", 2016 IOP Conf. Ser.: Mater. Sci. Eng. 104 012036, published Jan. 21, 2016.*

Allen, John. (2007). Photoplethysmography and it application in clinical physiological measurement. Physiological measurement. 28 . R1-39. 10.1088/0967-3334/28/3/R01.*

Merriam-Webster, "Near-ultraviolet", https://www.merriam-webster.com/dictionary/near-ultraviolet.*

Merriam-Webster, "Visible", https://www.merriam-webster.com/dictionary/visible.*

Enric Monte-Moreno, "Non-invasive estimate of blood glucose and blood pressure from a photoplethysmograph by means of machine learning techniques", Artificial Intelligence in Medicine, vol. 53, Issue 2, 2011, pp. 127-138, ISSN 0933-3657, https://doi.org/10.1016/j.artmed.2011.05.001.*

KC Manhesh et al., Wearable Wireless Intelligent Multi-Parameter Health Monitoring Watch, 2013, Texas Instruments India Educators' Conference, IEEE, p. 61-64.

Abdallah et al., Design of a Compact Multi-Sensor System for Non-Invasive Glucose Monitoring Using Optical Spectroscopy, International Conference on Electronics, Biomedical Engineering and its Applications (ICEBEA'2012), Jan. 7-8, 2012, p. 310-317.

Forst et al., Cardiovascular Effects of Disturbed Insulin Activity in Metabolic Syndrome and in Type 2 Diabetic Patients, Insulin Secretion and Action, Horm Metab Res; 2009, 41; p. 123-131.

Mohamed Elgendi, On the Analysis of Fingertip Photoplethysmogram Signals, Current Cardiology Reviews, 2012, 8, p. 14-25, Bentham Science Publishers.

Wikipedia, Cytochrome P450, Dec. 31, 2015, p. 1-12.

Oliver Wieben, Light Absorbance in Pulse Oximetry, Taylor & Francis, 1997, IOP Publishing, p. 1-20.

Wikipedia, Photoplethysmogram, Jul. 25, 2015, p. 1-4.

PCT/US2016/053631 . Int'l search Report & Written Opinion (Dec. 8, 2016).

Babbage, "A cardiac biometric recognition system hopes to replace passwords and keys." Economist.com (May 9, 2013).

Elgendi, "On the analysis of fingertip photoplethysmogram signals." Current Cardiology Reviews 8:14-25 (2012).

PCT/US2019/018639. Int'l Preliminary Report on Patenability (dated Apr. 6, 2020).

PCT/US2019/018639. Int'l Search Report—Written Opinion (dated May 1, 2019).

* cited by examiner

SYSTEM AND METHOD FOR OBTAINING HEALTH DATA USING A NEURAL NETWORK

CROSS REFERENCE TO RELATED APPLICATIONS

The present application claims priority under 35 U.S.C. § 120 as a continuation in part application to U.S. patent application Ser. No. 15/811,479 entitled, "SYSTEM AND METHOD FOR A BIOSENSOR INTEGRATED IN A VEHICLE," filed Nov. 13, 2017 and hereby expressly incorporated by reference herein.

The present application claims priority under 35 U.S.C. § 120 as a continuation in part application to U.S. patent application Ser. No. 15/490,813 entitled, "SYSTEM AND METHOD FOR HEALTH MONITORING USING A NON-INVASIVE, MULTI-BAND BIOSENSOR," filed Apr. 18, 2017 and hereby expressly incorporated by reference herein which claims priority under 35 U.S.C. § 120 as a continuation application to U.S. Utility application Ser. No. 15/275,388 entitled, "SYSTEM AND METHOD FOR HEALTH MONITORING USING A NON-INVASIVE, MULTI-BAND BIOSENSOR," filed Sep. 24, 2016, now U.S. Pat. No. 9,642,578 issued May 9, 2017, and hereby expressly incorporated by reference herein.

The present application claims priority under 35 U.S.C. § 120 as a continuation in part application to U.S. patent application Ser. No. 15/489,391 entitled, "SYSTEM AND METHOD FOR A BIOSENSOR MONITORING AND TRACKING BAND," filed Apr. 17, 2017 and hereby expressly incorporated by reference herein, which claims priority under 35 U.S.C. § 120 as a continuation application to U.S. Utility application Ser. No. 15/275,444, entitled, "SYSTEM AND METHOD FOR A BIOSENSOR MONITORING AND TRACKING BAND," filed Sep. 25, 2016, now U.S. Pat. No. 9,642,538 issued May 9, 2017, and hereby expressly incorporated by reference herein.

The present application claims priority under 35 U.S.C. § 120 as a continuation in part application to U.S. patent application Ser. No. 15/485,816 entitled, "SYSTEM AND METHOD FOR A DRUG DELIVERY AND BIOSENSOR PATCH," filed Apr. 12, 2017 and hereby expressly incorporated by reference herein, which claims priority under 35 U.S.C. § 120 as a continuation application to U.S. Utility application Ser. No. 15/276,760, entitled, "SYSTEM AND METHOD FOR A DRUG DELIVERY AND BIOSENSOR PATCH," filed Sep. 26, 2016, now U.S. Pat. No. 9,636,457 issued May 2, 2017, which is hereby expressly incorporated by reference herein.

The present application claims priority under 35 U.S.C. § 120 as a continuation in part application to U.S. patent application Ser. No. 15/718,721 entitled, "SYSTEM AND METHOD FOR MONITORING NITRIC OXIDE LEVELS USING A NON-INVASIVE, MULTI-BAND BIOSENSOR," filed Sep. 28, 2017 and hereby expressly incorporated by reference herein, which claims priority as a continuation application to U.S. Utility application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017, now U.S. Pat. No. 9,788,767 issued Oct. 17, 2017, and hereby expressly incorporated by reference herein, which claims priority under 35 U.S.C. § 119 to U.S. Provisional Application No. 62/463,104 entitled, "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein.

The present application claims priority under 35 U.S.C. § 120 as a continuation in part application to U.S. patent application Ser. No. 15/804,581 entitled, "SYSTEM AND METHOD FOR HEALTH MONITORING INCLUDING A USER DEVICE AND BIOSENSOR," filed Nov. 6, 2017 and hereby expressly incorporated by reference herein, which claims priority as a continuation application to U.S. patent application Ser. No. 15/404,117 entitled, "SYSTEM AND METHOD FOR HEALTH MONITORING INCLUDING A USER DEVICE AND BIOSENSOR," filed Jan. 11, 2017 and hereby expressly incorporated by reference herein.

The present application claims priority under 35 U.S.C. § 120 as a continuation in part application to U.S. patent application Ser. No. 15/462,700 entitled, "SYSTEM AND METHOD FOR ATOMIZING AND MONITORING A DRUG CARTRIDGE DURING INHALATION TREATMENTS," filed Mar. 17, 2017 and hereby expressly incorporated by reference herein, which claims priority under 35 U.S.C. § 119(e) to U.S. Provisional Application No. 62/457,138 entitled, "SYSTEM AND METHOD FOR ATOMIZING AND MONITORING A DRUG CARTRIDGE DURING INHALATION TREATMENTS," filed Feb. 9, 2017, and hereby expressly incorporated by reference herein.

The present application claims priority under 35 U.S.C. § 120 as a continuation in part application to U.S. Utility application Ser. No. 15/680,991 entitled, "SYSTEM AND METHOD FOR DETECTING A SEPSIS CONDITION," filed Aug. 18, 2017, and hereby expressly incorporated by reference herein.

The present application claims priority under 35 U.S.C. § 120 as a continuation in part application to U.S. patent application Ser. No. 15/400,916 entitled, "SYSTEM AND METHOD FOR HEALTH MONITORING INCLUDING A REMOTE DEVICE," filed Jan. 6, 2017 and hereby expressly incorporated by reference herein.

The present application claims priority under 35 U.S.C. § 120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein.

The present application claims priority under 35 U.S.C. § 120 as a continuation in part to U.S. patent application Ser. No. 15/867,632 entitled, "SYSTEM AND METHOD FOR BLOOD TYOING USING PPG TECHNOLOGY," filed Jan. 10, 2018, and hereby expressly incorporated by reference herein.

The present application claims priority under 35 U.S.C. § 120 as a continuation in part to U.S. patent application Ser. No. 15/859,147 entitled, "VEHICLULAR HEALTH MONITORING SYSTEM AND METHOD," filed Dec. 29, 2017 and hereby expressly incorporated by reference herein.

The present application claims priority under 35 U.S.C. § 119(e) to U.S. Provisional Application No. 62/613,388 entitled, "SYSTEM AND METHOD FOR INFECTION DISCRIMINATION USING PPG TECHNOLOGY," filed Jan. 3, 2018, and hereby expressly incorporated by reference herein.

FIELD

This application relates to a system and methods of non-invasive health monitoring integrated in a vehicle, and in particular a system and method for health monitoring using spectral data from a plurality of biosensors integrated in a vehicle.

BACKGROUND

A person's vitals, such as temperature, blood oxygen levels, respiration rate, relative blood pressure, etc., may need to be monitored periodically typically using one or more instruments. For example, instruments for obtaining vitals of a user include blood pressure cuffs, thermometers, $SpO_2$ measurement devices, glucose level meters, etc. Often, multiple instruments must be used to obtain vitals of a person. This monitoring process is time consuming, inconvenient and is not always continuous. This multitude of instruments is also not portable or readily available to operators of a vehicle.

In addition, detection of substances and measurement of concentration level or indicators of various substances in a user's blood stream is important in health monitoring. Currently, detection of concentration levels of blood substances is performed by drawing blood from a blood vessel using a needle and syringe. The blood sample is then transported to a lab for analysis. This type of monitoring is invasive, non-continuous and time consuming.

One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood. Such PPG techniques are heretofore been limited to determining oxygen saturation.

When the heart pumps blood to the body and the lungs during systole, the amount of blood that reaches the capillaries in the skin surface increases, resulting in more light absorption. The blood then travels back to the heart through the venous network, leading to a decrease of blood volume in the capillaries and less light absorption. The measured PPG waveform therefore comprises a pulsatile (often called "AC") physiological waveform that reflects cardiac synchronous changes in the blood volume with each heartbeat, which is superimposed on a much larger slowly varying quasi-static ("DC") baseline As such, there is a need for a non-invasive health monitoring system and method that measures user vitals and monitors concentration levels or indicators of one or more substances in blood flow.

In addition, there is a need for a non-invasive, non-contact health monitoring system and method integrated in a user device to measure health data.

SUMMARY

According to a first aspect, a device includes a signal processing module configured to receive photoplethysmography (PPG) signals, wherein the PPG signals include a first spectral response obtained from light reflected around a first wavelength from skin tissue of a patient and a second spectral response obtained from light reflected around a second wavelength from skin tissue of a patient. The first wavelength has a high absorption coefficient for nitric oxide (NO), and the second wavelength has a lower absorption coefficient for NO. The signal processing module generates PPG input data using the PPG signals, wherein the PPG input data includes at least one of the first spectral response and the second spectral response; or one or more parameters obtained from the first spectral response and the second spectral response. The device further includes a neural network processing device configured to generate an input vector including the PPG input data and determine an output vector including the health data, wherein the health data includes one or more of: an oxygen saturation level, an NO concentration level or a glucose concentration level.

According to a second aspect, a device includes a signal processing module configured to receive photoplethysmography (PPG) signals, wherein the PPG signals include a first spectral response obtained from light reflected around a first wavelength from skin tissue of a patient and a second spectral response obtained from light reflected around a second wavelength from skin tissue of a patient and a third spectral response obtained from light reflected around a third wavelength from skin tissue of a patient. The signal processing module generates PPG input data using the PPG signals, wherein the PPG input data includes at least one of the first spectral response, the second spectral response and the third spectral response; or one or more parameters obtained from each of the first spectral response, the second spectral response, and the third spectral response. The device also includes a neural network processing device configured to generate an input vector including the PPG input data; and determine an output vector including health data, wherein the health data includes an oxygen saturation level and at least one additional substance in blood flow.

According to a third aspect, a neural network processing device includes a signal processing module configured to receive photoplethysmography (PPG) signals, wherein the PPG signals include a first spectral response obtained from light reflected around a first wavelength from skin tissue of a patient and a second spectral response obtained from light reflected around a second wavelength from skin tissue of a patient. The device also generates PPG input data using the PPG signals, wherein the PPG input data includes at least one of: the first spectral response and the second spectral response; or one or more parameters obtained from the first spectral response and the second spectral response. The device further includes a processing device configured to generate an input vector including the PPG input data and determine an output vector including health data, wherein the health data includes one or more of: a blood alcohol level, a liver enzyme level, or an ethanol level.

In one or more of the above aspects, the first wavelength is in a UV range and the second wavelength is in at least one of a visible range or an infrared (IR) range. For example, the first wavelength is in a range of 370 nm to 410 nm. The device of claim 1, wherein the health data further includes a risk of sepsis, a level of vasodilation, a diabetic risk factor, blood pressure, heart rate, or respiration rate.

In one or more of the above aspects, the input vector may further include patient data on pre-existing conditions, wherein at least one pre-existing condition includes data on a potential head injury and wherein the health data further includes a risk of concussion.

In one or more of the above aspects, the input vector further includes patient data on pre-existing conditions, wherein at least one pre-existing condition is a traumatic event and wherein the health data further includes PTSD.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Embodiment of the Biosensor

In an embodiment, a biosensor includes an optical sensor or photoplethysmography (PPG) circuit configured to transmit light at a plurality of wavelengths directed at skin tissue of a user or patient. The user/patient may include any living organism, human or non-human. The PPG circuit detects the light reflected from the skin tissue or transmitted through the skin tissue and generates one or more spectral responses at one or more wavelengths. A processing circuit integrated in the biosensor or in communication with the biosensor processes the spectral data to obtain a user's vitals, concentrations of substances in blood flow and/or other health information.

Figure 1:
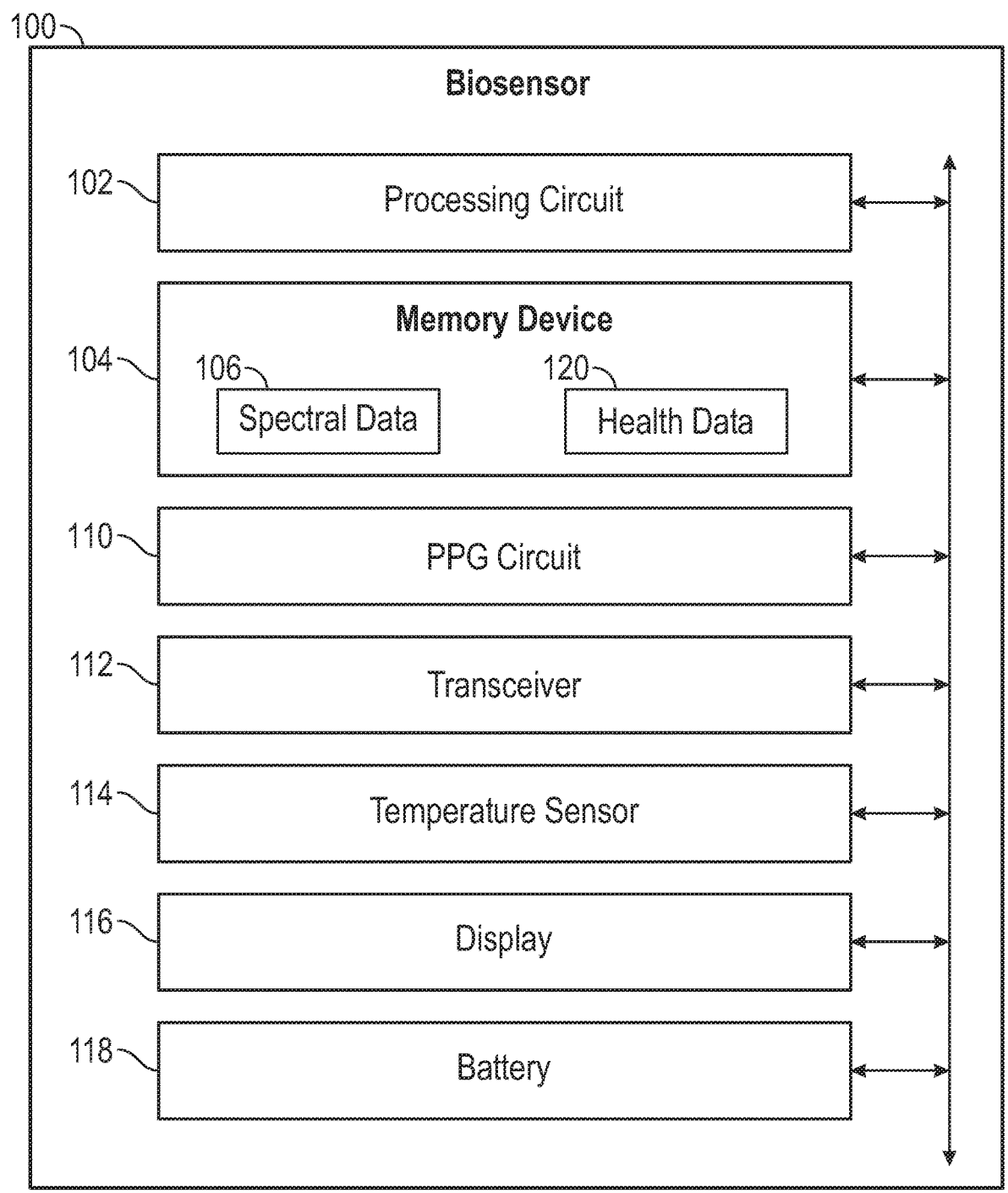
FIG. 1 illustrates a schematic block diagram of exemplary components in an embodiment of the biosensor.

FIG. 1 illustrates a schematic block diagram of exemplary components in an embodiment of the biosensor 100. The biosensor 100 includes a PPG circuit 110 as described in more detail herein. The PPG circuit 110 may be configured to detect oxygen saturation (SaO2 or SpO2) levels in blood flow, as well as heart rate and respiration rate. In addition, the PPG circuit 110 is configured to detect concentration levels of one or more substances in blood flow of a user, e.g., using one or more measurement techniques as described in more detail herein.

The biosensor 100 may include one or more processing circuits 102 communicatively coupled to a memory device 104. In one aspect, the memory device 104 may include one or more non-transitory processor readable memories that store instructions which when executed by the one or more processing circuits 102, causes the one or more processing circuits 102 to perform one or more functions described herein. The processing circuit 102 may be co-located with one or more of the other circuits of the biosensor 100 in a same physical circuit board or encasement or located separately in a different circuit board or encasement. The processing circuit 102 may also be communicatively coupled to a central control module or server in a remote location as described further herein. The biosensor 100 may be battery operated and include a battery 118, such as a lithium ion battery. The memory device may store spectral data 106 or health data 120 obtained by the biosensor 100.

The biosensor 100 may include a temperature sensor 114 configured to detect a temperature of a user. For example, the temperature sensor 108 may include an array of sensors (e.g., 16×16 pixels) to detect a temperature of skin tissue of a user. The temperature sensor 114 may also be used to calibrate the PPG circuit 110. The biosensor 100 may include a display 116 to display biosensor data or control GUI for the biosensor 100.

The biosensor 100 further includes a transceiver 112. The transceiver 112 may include a wireless or wired transceiver configured to communicate with or with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. The transceiver 112 may also include a wired transceiver interface, e.g., a USB port or other type of wired connection, for communication with one or more other devices over a LAN, MAN and/or WAN. The transceiver 112 may include a wireless or wired transceiver configured to communicate with a vehicle or its components over a controller area network (CAN), Local Interconnect Network (LIN), Flex Ray, Media Oriented Systems Transport (MOST), (On-Board Diagnostics II), Ethernet or using another type of network or protocol. The biosensor 100 may transmit the health information using the transceiver 112 over a wide area network, such as a cellular network, to a third party service provider, such as a health care provider or emergency service provider. The vehicle may also transmit the health data 120, e.g. via a Bluetooth or WLAN interface, to a user device.

Embodiment—PPG Circuit

Figure 2:
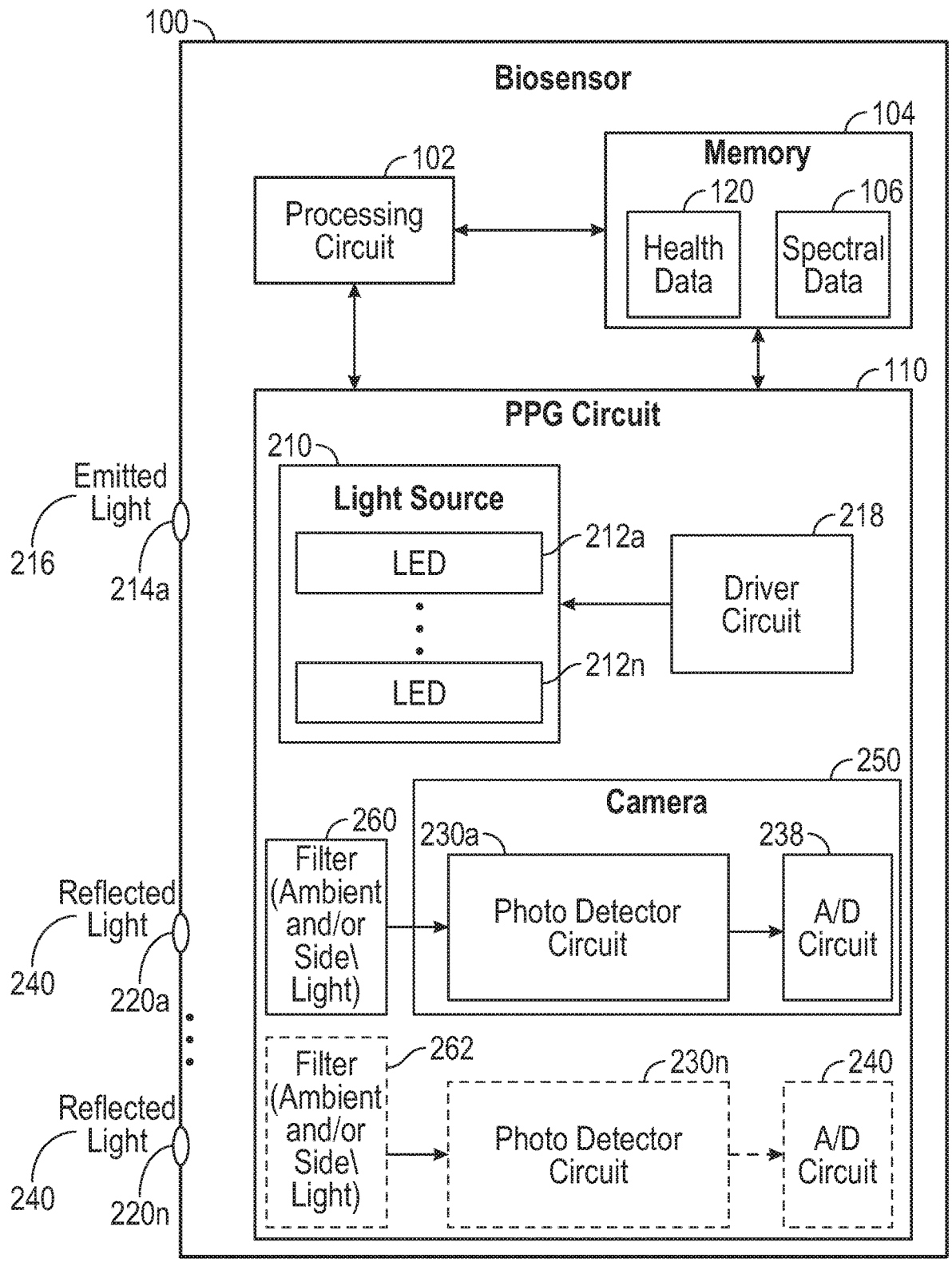
FIG. 2 illustrates a schematic block diagram of an embodiment of the PPG circuit in more detail.

FIG. 2 illustrates a schematic block diagram of an embodiment of the PPG circuit 110 in more detail. The PPG circuit 110 includes a light source 210 configured to emit a plurality of wavelengths of light across various spectrums. The plurality of LEDs 212a-n are configured to emit light in one or more spectrums, including infrared (IR) light, ultraviolet (UV) light, near IR light or visible light, in response to driver circuit 218. For example, the biosensor 100 may include a first LED 212a that emits visible light and a second LED 212b that emits infrared light and a third LED 212c that emits UV light, etc. In another embodiment, one or more of the light sources 212a-n may include tunable LEDs or lasers operable to emit light over one or more frequencies or ranges of frequencies or spectrums in response to driver circuit 218.

In an embodiment, the driver circuit 218 is configured to control the one or more LEDs 212a-n to generate light at one or more frequencies for predetermined periods of time. The driver circuit 218 may control the LEDs 212a-n to operate concurrently or consecutively. The driver circuit 218 is configured to control a power level, emission period and frequency of emission of the LEDs 212a-n. The biosensor 100 is thus configured to emit one or more wavelengths of light in one or more spectrums that is directed at the surface or epidermal layer of the skin tissue of a user. The emitted light 216 passes through at least one aperture 214 directed at the surface or epidermal layer of the skin tissue of a user.

The PPG circuit 110 further includes one or more photodetector circuits 230a-n. The photodetector circuits 230 may be implemented as part of a camera 250. For example, a first photodetector circuit 230 may be configured to detect visible light and the second photodetector circuit 230 may be configured to detect IR light. Alternatively, one or more of the photodetectors 230a-n may be configured to detect light across multiple spectrums. When multiple photodetectors 230 are implemented, the detected signals obtained from each of the photodetectors may be added or averaged. Alternatively, a detected light signal with more optimal signal to noise ration may be selected from the multiple photodetector circuits 230a-n.

The first photodetector circuit 230 and the second photodetector circuit 230 may also include a first filter 260 and a second filter 262 configured to filter ambient light and/or scattered light. For example, in some embodiments, only light reflected at an approximately perpendicular angle to the skin surface of the user is desired to pass through the filters. The first photodetector circuit 230 and the second photodetector circuit 230n are coupled to a first A/D circuit 238 and a second A/D circuit 240. Alternatively, a single A/D circuit may be coupled to each of the photodetector circuits 230a-n.

In another embodiment, a single photodetector circuit 230 may be implemented operable to detect light over multiple spectrums or frequency ranges. The one or more photodetector circuits 230 include one or more types of spectrometers or photodiodes or other type of circuit configured to detect an intensity of light as a function of wavelength to obtain a spectral response. In use, the one or more photodetector circuits 230 detect the intensity of reflected light 240 from skin tissue of a user that enters one or more apertures 220a-n of the biosensor 100. In another example, the one or more photodetector circuits 230 detect the intensity of light due to transmissive absorption (e.g., light transmitted through tissues, such as a fingertip or ear lobe). The one or more photodetector circuits 230a-n then obtain a spectral response of the reflected or transmissive light by measuring an intensity of the light at one or more wavelengths.

In another embodiment, the light source 210 may include a broad spectrum light source, such as a white light to infrared (IR) or near IR LED, that emits light with wavelengths across multiple spectrums, e.g. from 350 nm to 2500 nm. Broad spectrum light sources with different ranges may be implemented. In an aspect, a broad spectrum light source is implemented with a range across 100 nm wavelengths to 2000 nm range of wavelengths in the visible, IR and/or UV frequencies. For example, a broadband tungsten light source for spectroscopy may be used. The spectral response of the reflected light 240 is then measured across the wavelengths in the broad spectrum, e.g. from 350 nm to 2500 nm, concurrently. In an aspect, a charge coupled device (CCD) spectrometer may be configured in the photodetector circuit 230 to measure the spectral response of the detected light over the broad spectrum.

The PPG circuit 110 may also include a digital signal processing (DSP) circuit or filters or amplifiers to process the spectral data. The spectral data may then be processed by the processing circuit 102 to obtain health data 120 of a user. The spectral data 106 may alternatively or in additionally be transmitted by the biosensor 100 to a central control module for processing to obtain health data 120 of a user.

One or more of the embodiments of the biosensor 100 described herein is configured to detect a concentration level of one or more substances within blood flow using photoplethysmography (PPG) techniques. For example, the biosensor 100 may detect nitric oxide (NO) concentration levels and correlate the NO concentration level to a blood glucose level. The biosensor 100 may also detect oxygen saturation (SaO2 or SpO2) levels in blood flow. The biosensor may also be configured to detect a liver enzyme cytochrome oxidase (P450) enzyme and correlate the P450 concentration level to a blood alcohol level. The biosensor 100 may also detect vitals, such as heart rate and respiration rate. Because blood flow to the skin can be modulated by multiple other physiological systems, the biosensor 100 may also be used to monitor hypovolemia and other circulatory conditions.

In use, the biosensor 100 performs PPG techniques using the PPG circuit 110 to detect the concentration levels of one or more substances in blood flow. In one aspect, the biosensor 100 receives reflected light or transmissive light from skin tissue to obtain a spectral response. The spectral response includes a spectral curve that illustrates an intensity or power or energy at a frequency or wavelength in a spectral region of the detected light. The ratio of the resonance absorption peaks from two different frequencies can be calculated and based on the Beer-Lambert law used to obtain the levels of substances in the blood flow.

First, the spectral response of a substance or substances in the arterial blood flow is determined in a controlled environment, so that an absorption coefficient $\alpha_{g1}$ can be obtained at a first light wavelength $\lambda 1$ and at a second wavelength $\lambda 2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined. For example, the concentration Cg may be obtained from the following equations:

At the first wavelength $\lambda_1$, $I_1 = I_{in1} * 10^{-(\alpha_{g1} C_{gw} + \alpha_{w1} C_w)*l}$ At the second wavelength $\lambda_2$, $I_2 = I_{in2} * 10^{-(\alpha_{g2} C_{gw} + \alpha_{w2} C_w)*l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I_1}{I_{in1}}\right)}{\log 10\left(\frac{I_2}{I_{in2}}\right)}$$

The concentration of the substance Cg may then be equal to:

$$Cg = \frac{Cgw}{Cgw + Cw} = \frac{\alpha_{w2} R - \alpha_{w1}}{(\alpha_{w2} - \alpha_{gw2}) * R - (\alpha_{w1} - \alpha_{gw1})}$$

The biosensor 100 may thus determine the concentration of various substances in arterial blood flow from the Beer-Lambert principles using the spectral responses of at least two different wavelengths.

Figure 3:
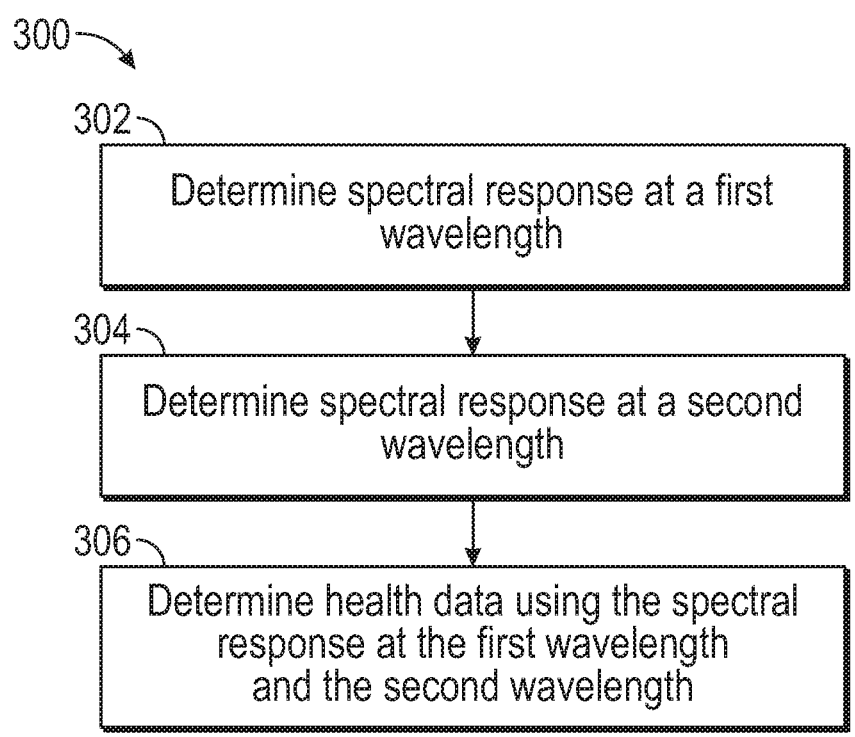
FIG. 3 illustrates a logical flow diagram of an embodiment of a method for determining concentration level of a substance in blood flow using Beer-Lambert principles.

FIG. 3 illustrates a logical flow diagram of an embodiment of a method 300 for determining concentration level of a substance in blood flow using Beer-Lambert principles. The biosensor 100 transmits light at a first predetermined wavelength and at a second predetermined wavelength. The biosensor 100 detects the light (reflected from the skin or transmitted through the skin) and determines the spectral response at the first wavelength at 302 and at the second wavelength at 304. The biosensor 100 then determines health data, such as an indicator or concentration level of substances in blood flow, using the spectral responses of the first and second wavelength at 306. In general, the first predetermined wavelength is selected that has a high absorption coefficient for the substance in blood flow while the second predetermined wavelength is selected that has a lower absorption coefficient for the substance in blood flow. Thus, it is generally desired that the spectral response for the first predetermined wavelength have a higher intensity level in response to the substance than the spectral response for the second predetermined wavelength.

In an embodiment, the biosensor 100 may detect a concentration level of nitric oxide (NO) in blood flow using a first predetermined wavelength in a range of 380-410 nm and in particular at 390 nm or 395 nm. In another aspect, the biosensor 100 may transmit light at the first predetermined wavelength in a range of approximately 1 nm to 50 nm around the first predetermined wavelength. Similarly, the biosensor 100 may transmit light at the second predetermined wavelength in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated at 302 and 304. The biosensor 100 analyzes the first and second spectral responses to detect an indicator or concentration level of NO in the arterial blood flow at 306.

Photoplethysmography (PPG) is used to measure time-dependent volumetric properties of blood in blood vessels due to the cardiac cycle. For example, the heartbeat affects the volume of blood flow and the concentration or absorption levels of substances being measured in the arterial blood flow. Over a cardiac cycle, pulsating arterial blood changes the volume of blood flow in a blood vessel. Incident light $I_O$ is directed at a tissue site and a certain amount of light is reflected or transmitted and a certain amount of light is absorbed. At a peak of blood flow or volume in a cardiac cycle, the reflected/transmitted light $I_L$ is at a minimum due to absorption by the increased blood volume, e.g, due to the pulsating blood in the vessel. At a minimum of blood volume during the cardiac cycle, the transmitted/reflected light $I_H$ 416 is at a maximum due to lack of absorption from the pulsating blood.

The biosensor 100 is configured to filter the reflected/transmitted light $I_L$ of the pulsating blood from the transmitted/reflected light $I_H$. This filtering isolates the light due to reflection/transmission of the pulsating blood from the light due to reflection/transmission from non-pulsating blood, vessel walls, surrounding tissue, etc. The biosensor 100 may then measure the concentration levels of one or more substances from the reflected/transmitted light $I_L$ 814 in the pulsating blood.

For example, incident light $I_O$ is directed at a tissue site at one or more wavelengths. The reflected/transmitted light I is detected by a photodetector or sensor array in a camera. At a peak of blood flow or volume, the reflected light $I_L$ 414 is at a minimum due to absorption by the pulsating blood, non-pulsating blood, other tissue, etc. At a minimum of blood flow or volume during the cardiac cycle, the Incident or reflected light $I_H$ 416 is at a maximum due to lack of absorption from the pulsating blood volume. Since the light I is reflected or traverses through a different volume of blood at the two measurement times, the measurement provided by a PPG sensor is said to be a 'volumetric measurement' descriptive of the differential volumes of blood present at a certain location within the user's vessels at different times during the cardiac cycle. These principles described herein may be applied to venous blood flow and arterial blood flow.

In general, the relative magnitudes of the AC and DC contributions to the reflected/transmitted light signal I may be determined. In general, AC contribution of the reflected light signal I is due to the pulsating blood flow. A difference function may thus be computed to determine the relative magnitudes of the AC and DC components of the reflected light I to determine the magnitude of the reflected light due to the pulsating blood flow. The described techniques herein for determining the relative magnitudes of the AC and DC contributions is not intended as limiting. It will be appreciated that other methods may be employed to isolate or otherwise determine the relative magnitude of the light $I_L$ due to pulsating blood flow (arterial and/or venous).

Figure 4:
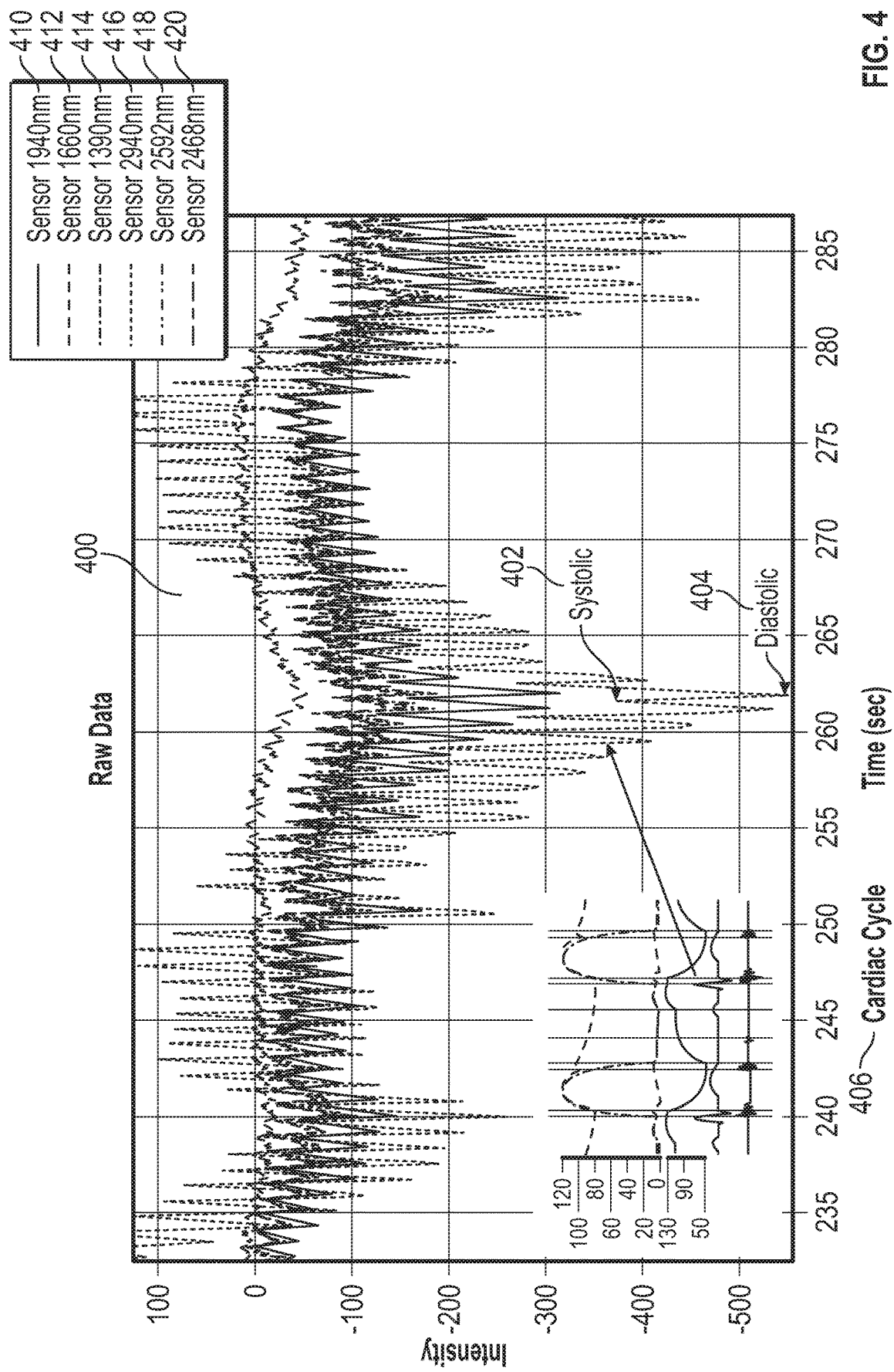
FIG. 4 illustrates a schematic diagram of a graph of spectral data obtained using an embodiment of the biosensor.

FIG. 4 illustrates a schematic diagram of a graph of spectral data obtained using an embodiment of the biosensor 100. In one aspect, the biosensor 100 is configured to emit or pulse light at a plurality of wavelengths during a measurement period. The light at each wavelength (or range of wavelengths) may be emitted concurrently or sequentially. The intensity of the reflected light at each of the wavelengths (or range of wavelengths) is detected, and the spectral response is graphed over the measurement period. The spectral responses for the plurality of wavelengths are obtained using an embodiment of the biosensor in clinical trials. In this clinical trial, two biosensors 100 attached to two separate fingertips of a user were used to obtain the spectral responses 508. The first biosensor 100 obtained the spectral response for a wavelength at 940 nm 410, a wavelength at 660 nm 412 and a wavelength at 390 nm 414. The second biosensor 100 obtained the spectral response for a wavelength at 940 nm 416, a wavelength at 592 nm 418 and a wavelength at 468 nm 420.

In one aspect, the spectral response obtained at each wavelength may be aligned based on the systolic 502 and diastolic 504 points in their respective spectral responses. This alignment is useful to associate each spectral response with a particular stage or phase of the pulse-induced local pressure wave within the blood vessel (which roughly mimics the cardiac cycle 406 and thus include systolic and diastolic stages and sub-stages thereof). This temporal alignment helps to determine the absorption measurements acquired near a systolic point in time of the cardiac cycle and near the diastolic point in time of the cardiac cycle 506 associated with the local pressure wave within the user's blood vessels. This measured local pulse timing information may be useful for properly interpreting the absorption measurements in order to determine the relative contributions of the AC and DC components measured by the biosensor 100. So for one or more wavelengths, the systolic points 502 and diastolic points 504 in the spectral response are determined. These systolic points 502 and diastolic points 504 for the one or more wavelengths may then be aligned as a method to discern concurrent responses across the one or more wavelengths.

In another embodiment, the systolic points 502 and diastolic points 504 in the absorbance measurements are temporally correlated to the pulse-driven pressure wave within the blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 4 illustrates the spectral response obtained at the plurality of wavelengths with the systolic points 402 and diastolic points 404 aligned.

Figure 5:
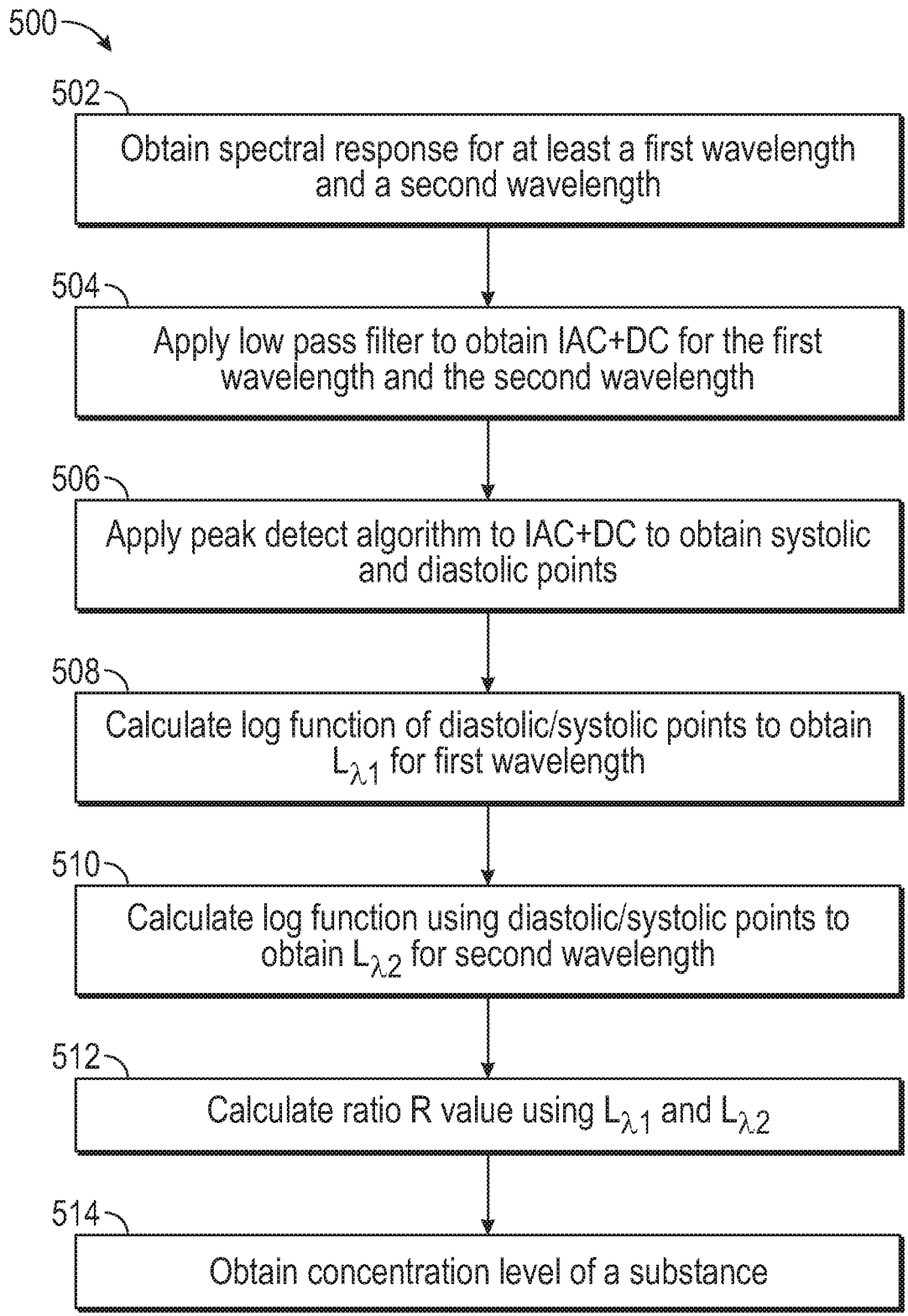
FIG. 5 illustrates a logical flow diagram of an embodiment of a method of the biosensor.

FIG. 5 illustrates a logical flow diagram of an embodiment of a method 500 of the biosensor 100. In one aspect, the biosensor 100 emits and detects light at a plurality of predetermined frequencies or wavelengths, such as approximately 940 nm, 660 nm, 390 nm, 592 nm, and 468 nm or in ranges thereof. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the user in a range of 360 nm to 410 nm including the predetermined wavelength 390 nm. For the predetermined wavelength of 940 nm, the biosensor 100 may transmit light directed at the skin tissue of the user in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 502. The spectral responses may be measured over a predetermined period (such as 300 usec) or at least over 2-3 cardiac cycles. This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The spectral data obtained by the PPG circuit 110, such as the digital or analog spectral responses, may be processed locally by the biosensor 100 or transmitted to a central control module for processing.

The systolic and diastolic points of the spectral response are then determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined.

A low pass filter (such as a 5 Hz low pass filter) is applied to the spectral response signal at 504. The relative contributions of the AC and DC components are obtained $I_{AC+DC}$ and $I_{AC}$. A peak detection algorithm is applied to determine the systolic and diastolic points at 506. If not detected concurrently, the systolic and diastolic points of the spectral response for each of the wavelengths may be aligned or may be aligned with systolic and diastolic points of a pressure pulse waveform or cardiac cycle.

Beer Lambert equations are then applied as described herein. For example, the $L_\lambda$ values are then calculated for the first wavelength $\lambda_1$ at 508 and the second wavelength $\lambda_2$ at 510, wherein the $L_\lambda$ values for a wavelength equals:

$$L_\lambda = \text{Log}10\left(\frac{IAC + DC}{IDC}\right)$$

wherein $I_{AC+DC}$ is the intensity of the detected light with AC and DC components and $I_{DC}$ is the intensity of the detected light with the AC component filtered by the low pass filter. The value $L_\lambda$ isolates the spectral response due to pulsating arterial blood flow, e.g. the AC component of the spectral response.

A ratio R of the $L_\lambda$ values at two wavelengths may then be determined at 512. For example, the ratio R may be obtained from the following:

$$\text{Ratio } R = \frac{L\lambda 1}{L\lambda 2}$$

The spectral responses may be measured and the $L_\lambda$ values and Ratio R determined continuously, e.g. every 1-2 seconds, and the obtained $L_\lambda$ values and/or Ratio R averaged over a predetermined time period, such as over 1-2 minutes. The concentration level of a substance may then be obtained from the R value and a calibration database at 514. The biosensor 100 may continuously monitor a user over 2-3 hours or continuously over days or weeks.

In one embodiment, the $R_{390,940}$ value with $L_{\lambda 1=390\,nm}$ and $L_{\lambda 2=940}$ may be non-invasively and quickly and easily obtained using the biosensor 100 to determine a concentration level of nitric oxide NO in blood flow of a user. In particular, in unexpected results, it is believed that the nitric oxide NO levels in the blood flow is being measured at least in part by the biosensor 100 at wavelengths in the range of 380-410 and in particular at $\lambda_1$=390 nm. Thus, the biosensor 100 measurements to determine the $L_{390\,nm}$ values are the first time NO concentration levels in arterial blood flow have been measured directly in vivo. These and other aspects of the biosensor 100 are described in more detail herein with clinical trial results.

Figure 6:
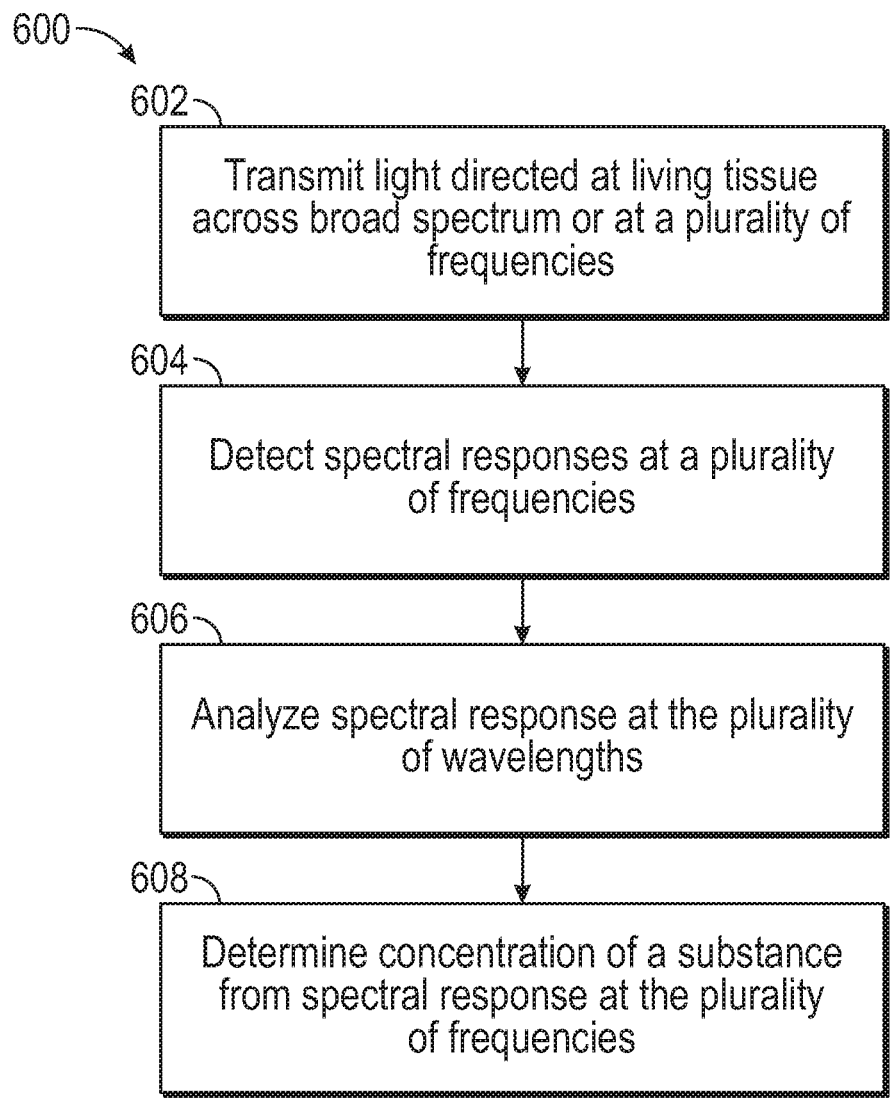
FIG. 6 illustrates a logical flow diagram of an exemplary method to determine levels of a substance in blood flow using the spectral responses at a plurality of wavelengths.

Embodiment—Determination of Concentration Level of a Substance Using PPG Signals at a Plurality of Wavelengths FIG. 6 illustrates a logical flow diagram of an exemplary method 600 to determine levels of a substance in blood flow using the PPG spectral responses at a plurality of wavelengths. The absorption coefficient of a substance may be sufficiently higher at a plurality of wavelengths, e.g. due to isoforms or derivative compounds. For example, the increased intensity of light at a plurality of wavelengths may be due to reflectance by isoforms or other compounds in the arterial blood flow. Another method for determining the concentration levels may then be used by measuring the spectral responses and determining L and R values at a plurality of different wavelengths of light. In this example then, the concentration level of the substance is determined using spectral responses at multiple wavelengths. An example for calculating the concentration of a substance over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n When the absorption coefficients $\mu_{1-n}$ of a substance, its isoforms or other compounds including the substance are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of the substance may be isolated from the isoforms or other compounds by compensating for the concentration of the compounds. Thus, using the spectral responses at multiple frequencies provides a more robust determination of the concentration level of a substance.

In use, the biosensor 100 transmits light directed at skin tissue at a plurality of wavelengths or over a broad spectrum at 602. The spectral response of light from the skin tissue is detected at 604, and the spectral responses are analyzed at a plurality of wavelengths (and in one aspect including a range of +/−10 to 50 nm around each of the wavelengths) at 606. Then, the concentration level C of the substance may be determined using the spectral responses at the plurality of wavelengths at 608. The concentration level of the substance may be isolated from isoforms or other compounds by compensating for the concentration of the compounds.

Figure 7:
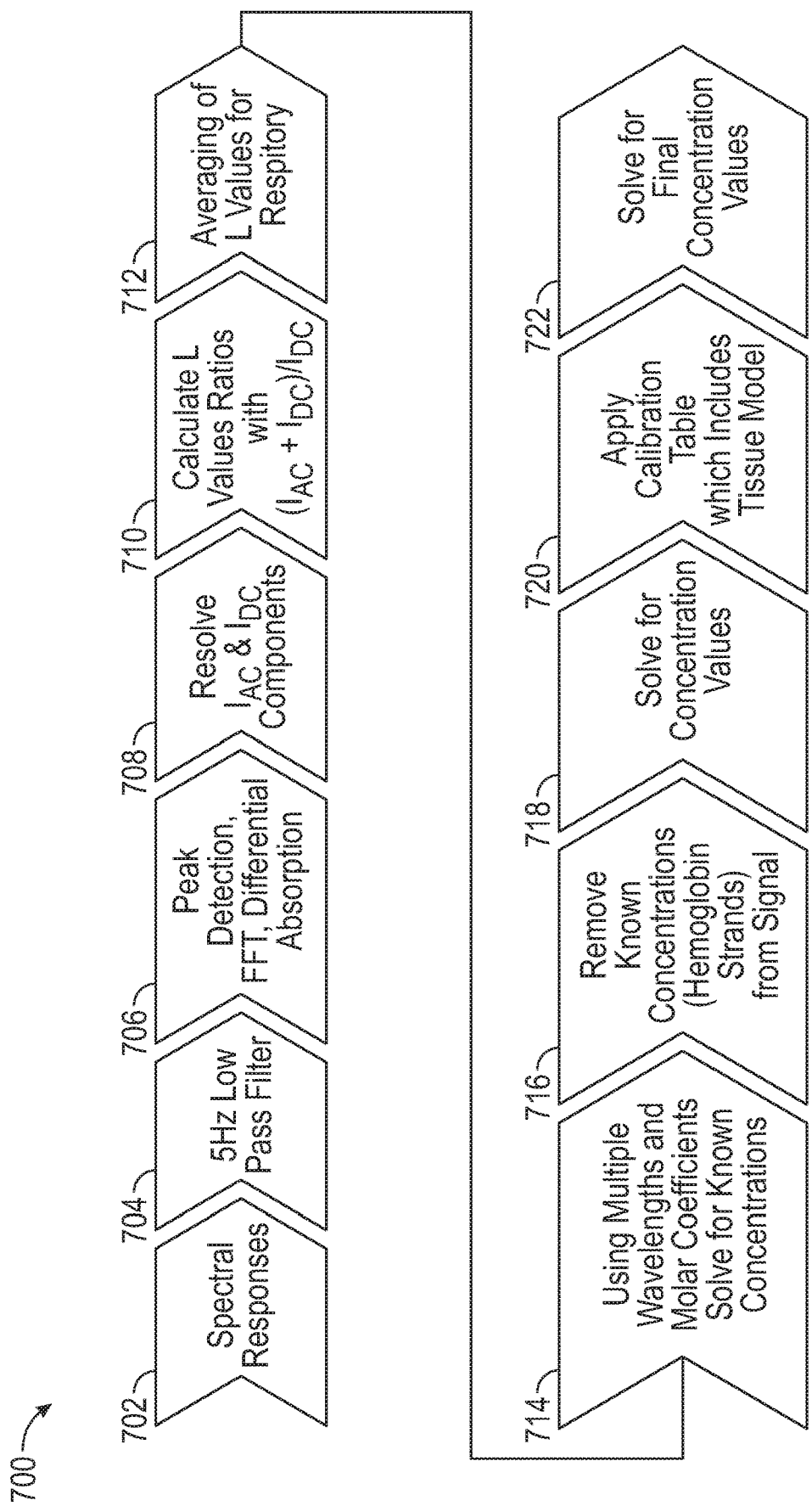
FIG. 7 illustrates a logical flow diagram of an exemplary method to determine levels of a substance using the spectral responses at a plurality of wavelengths in more detail.

FIG. 7 illustrates a logical flow diagram of an exemplary method 700 to determine levels of a substance using the spectral responses at a plurality of wavelengths in more detail. The spectral responses are obtained at 702. The spectral response signals include AC and DC components $T_{AC+DC}$. A low pass filter (such as a 5 Hz low pass filter) is applied to each of the spectral response signals $I_{AC+DC}$ to isolate the DC component of each of the spectral response signals $I_{DC}$ at 704. The AC fluctuation is due to the pulsatile expansion of the vessels due to the volume increase in pulsating blood. In order to measure the AC fluctuation, measurements are taken at different times and a peak detection algorithm is used to determine the diastolic point and the systolic point of the spectral responses at 706. A Fast Fourier transform (FFT) algorithm may also be used to isolate the DC component $I_{DC}$ and AC component of each spectral response signal at 706. A differential absorption technique may also be used as described in more detail herein. The $I_{DC}$ component is thus isolated from the spectral signal at 708.

The $I_{AC+DC}$ and $I_{DC}$ components are then used to compute the L values at 710. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period) or over a plurality of cardiac cycles at 712.

In an embodiment, isoforms of a substance may be attached in the blood stream to one or more types of hemoglobin compounds. The concentration level of the hemoglobin compounds may then need to be accounted for to isolate the concentration level of the substance from the hemoglobin compounds. For example, nitric oxide (NO) is found in the blood stream in a gaseous form and also attached to hemoglobin compounds. Thus, the spectral responses obtained around 390 nm (+/−20 nm) may include a concentration level of the hemoglobin compounds as well as nitric oxide. The hemoglobin compound concentration levels must thus be compensated for to isolate the nitric oxide concentration levels. Multiple wavelengths and absorption coefficients for hemoglobin are used to determine a concentration of the hemoglobin compounds at 714. Other methods may also be used to obtain a concentration level of hemoglobin in the blood flow as well. The concentration of the hemoglobin compounds is then adjusted from the measurements at 716. The concentration values of the substance may then be obtained at 718. For example, the R values are then determined at 718.

To determine a concentration level of the substance, a calibration table or database is used that associates the obtained R value to a concentration level of the substance at 720. The calibration database correlates the R value with a concentration level. The calibration database may be generated for a specific user or may be generated from clinical data of a large sample population. For example, it is determined that the R values should correlate to similar NO concentration levels across a large sample population. Thus, the calibration database may be generated from testing of a large sample of a general population to associate R values and NO concentration levels.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and concentration levels of a substance depending on the underlying skin tissue characteristics that were measured. The concentration level of the substance in blood flow is then obtained using the calibration table at 722. The concentration level may be expressed as mmol/liter, as a saturation level percentage, as a relative level on a scale, etc.

In another embodiment, in order to remove the hemoglobin concentration(s) from the original PPG signals, a mapping function may be created which is constructed through clinical data and tissue modeling. For example, known $SpO_2$ values in the infrared region and the same signals at the UV side of the spectrum are obtained. Then a linear inversion map can be constructed where the R values are input into a function and the desired concentration(s) can be determined. For example, a curve that correlates R values to concentration levels may be tabulated. A polynomial equation with multiple factors can also be used to account for different R values to represent the linear inversion map. This correlation may be derived from validated clinical data.

For example, a regression curve that correlates R values and NO concentration levels may be generated based on clinical data from a large general population. A polynomial may be derived from the curve and used to solve for an NO concentration level from the R value. The polynomial is stored in the calibration database and may be used rather than using a calibration look-up table or curve.

Embodiment—Determination of a Concentration of Hemoglobin Compounds

The Beer-Lambert theory may be generalized for a multi-wavelength system to determine a concentration of known hemoglobin species using the following matrix notation:

$$\begin{bmatrix} dA_{\lambda 1}^{LB} \\ \vdots \\ dA_{\lambda n}^{LB} \end{bmatrix} = \begin{bmatrix} \Delta l_{\lambda 1} & \cdots & 0 \\ \vdots & & \vdots \\ 0 & \cdots & \Delta l_{\lambda n} \end{bmatrix} \begin{bmatrix} \varepsilon_{\lambda 1, HbX_1} & \cdots & \varepsilon_{\lambda 1, HbX_m} \\ \vdots & \ddots & \vdots \\ \varepsilon_{\lambda n, HbX_1} & \cdots & \varepsilon_{\lambda n, HbX_m} \end{bmatrix} \cdot \begin{bmatrix} HbX_1 \\ \vdots \\ HbX_m \end{bmatrix} \cdot c(Hb),$$

wherein
$dA_\lambda^{LB}$ is a differential absorption within the Beer-Lambert model
$\varepsilon_{\lambda n1, HbX1}$ is an extinction coefficient
HbX are hemoglobin fractions
$\Delta l\lambda$ is the optical path-length for wavelength $\lambda$
c(Hb) is the hemoglobin concentration
This Beer-Lambert matrix equation for determining hemoglobin concentration levels may be solved when m is equal or greater than n, e.g., which means that at least four wavelengths are needed to solve for four hemoglobin species. The spectral responses at these four wavelengths may be analyzed to determine the concentration of the plurality of hemoglobin species.

The hemoglobin species include, e.g., Oxyhemoglobin [$HbO_2$ or OxyHb], Carboxyhemoglobin [HbCO or CarboxyHb], Methemoglobin [HbMet or MetHb], and deoxygenated hemoglobin (DeoxyHb or RHb). A method for determining the relative concentration or composition of hemoglobin species included in blood is described in more detail in U.S. Pat. No. 6,104,938 issued on Aug. 15, 2000, which is hereby incorporated by reference herein.

A direct calibration method for calculating hemoglobin species may be implemented by the biosensor 100. Using four wavelengths and applying a direct model for four hemoglobin species in the blood, the following equation results:

$$HbX = \frac{a_1 * dA_1 + a_2 * dA_2 + a_3 * dA_3 + a_4 * dA_4}{b_1 * dA_1 + b_2 * dA_2 + b_3 * dA_3 + b_4 * dA_4}$$

wherein $dA_\lambda$ is the differential absorption signal $a_n$ and $b_n$ are calibration coefficients The calibration coefficients $a_n$ and $b_n$ may be experimentally determined over a large population average. The biosensor 100 may include a calibration database to account for variances in the calibration coefficients $\alpha_1$ and $b_1$ (or extinction coefficients) for the hemoglobin species for various underlying tissue characteristics.

A two-stage statistical calibration and measurement method for performing PPG measurement of blood analyte concentrations may also be implemented by the biosensor 100. Concentrations of MetHb, $HbO_2$, RHb and HbCO are estimated by first estimating a concentration of MetHb (in a first stage) and subsequently, if the concentration of MetHb is within a predetermined range, then the estimated concentration of MetHb is assumed to be accurate and this estimated concentration of MetHb is utilized as a "known value" in determining the concentrations of the remaining analytes $HbO_2$, RHb and HbCO (in a second stage). This method for determining a concentration of hemoglobin species using a two stage calibration and analyte measurement method is described in more detail in U.S. Pat. No. 5,891,024 issued on Apr. 6, 1999, which is hereby incorporated by reference herein.

The concentration of the hemoglobin compounds may thus be determined. The biosensor 100 compensates for the hemoglobin concentration in determinations to obtain the concentration level of NO by the biosensor 100. Though several methods are described herein for obtaining a concentration of hemoglobin analytes, other methods or processes may be used by the biosensor 100 to determine the concentration of hemoglobin analytes or otherwise adjusting or compensating the obtained measurements to account for a hemoglobin concentration when determining the concentration levels of NO in a blood stream.

Embodiment—Determination of Concentration Levels of a Substance Using Shifts in Absorbance Peaks In another embodiment, a concentration level of a substance may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

The biosensor 100 may detect nitric oxide in vivo using PPG techniques by measuring the shift in the absorbance spectra curve of reduced hemoglobin in tissue and/or arterial blood flow. The absorbance spectra curve shifts with a peak from around 430 nm to a peak around 411 nm depending on the production of methemoglobin. The greater the degree of the shift of the peak of the curve, the higher the production of methemoglobin and NO concentration level. Correlations may be determined between the degree of the measured shift in the absorbance spectra curve of reduced hemoglobin to an NO concentration level. The correlations may be determined from a large sample population or for a particular user and stored in a calibration database. The biosensor 100 may thus obtain an NO concentration level by measuring the shift of the absorbance spectra curve of reduced hemoglobin. A similar method of determining shifts in an absorbance spectra may be implemented to determine a blood concentration level of other substances.

The biosensor 100 may obtain an NO concentration level by measuring the shift of the absorbance spectra curve of deoxygenated hemoglobin and/or by measuring the shift of the absorbance spectra curve of oxygenated hemoglobin in vivo. The biosensor 100 may then access a calibration database that correlates the measured shift in the absorbance spectra curve of deoxygenated hemoglobin to an NO concentration level. Similarly, the biosensor may access a calibration database that correlates the measured shift in the absorbance spectra curve of oxygenated hemoglobin to an NO concentration level.

Figure 8:
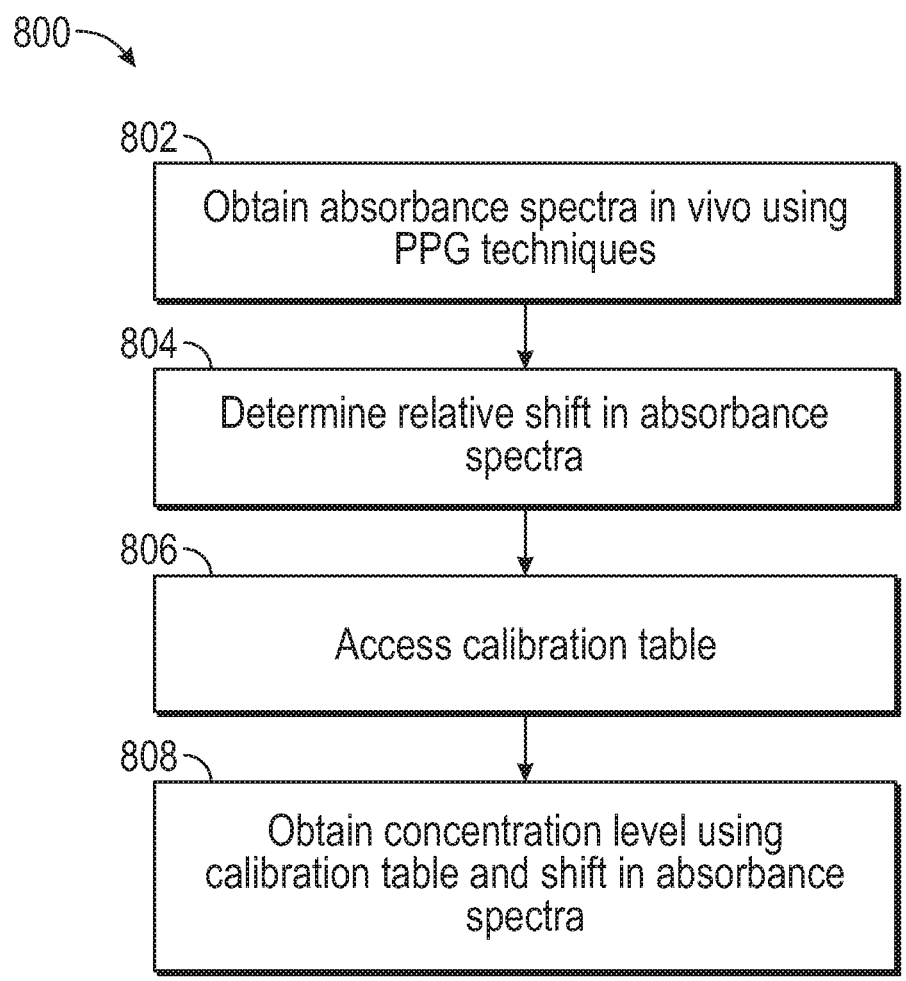
FIG. 8 illustrates a logical flow diagram of an exemplary embodiment of a method for measuring a concentration level of a substance in vivo using shifts in absorbance spectra.

FIG. 8 illustrates a logical flow diagram of an exemplary embodiment of a method 800 for measuring a concentration level of a substance in vivo using shifts in absorbance spectra. The biosensor 100 may obtain a concentration of the substance by measuring shifts in absorbance spectra of one or more substances that interact with the substance. For example, the one or more substances may include oxygenated and deoxygenated hemoglobin (HB). The PPG circuit 110 detects a spectral response at a plurality of wavelengths of the one or more substances that interact with the substance at 802. The biosensor 100 determines the relative shift in the absorbance spectra for the substance at 804. For example, the biosensor 100 may measure the absorbance spectra curve of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of the substance at 806. The biosensor 100 may thus obtain a concentration level of the substance in blood flow using a calibration database and the measured relative shift in absorbance spectra at 808.

The various methods thus include one or more of: Peak & Valley (e.g., peak detection), FFT, and differential absorption. Each of the methods require different amounts of computational time which affects overall embedded computing time for each signal, and therefore can be optimized and selectively validated with empirical data through large clinical sample studies. The biosensor 100 may use a plurality of these methods to determine a plurality of values for the concentration level of the substance. The biosensor 100 may determine a final concentration value using the plurality of values. For example, the biosensor 100 may average the values, obtain a mean of the values, etc.

The biosensor 100 may be configured for measurement on a fingertip or palm, wrist, an arm, forehead, chest, abdominal area, ear lobe, or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue. The PPG circuit 110 may adjust a power of the LEDs or a frequency or wavelength of the LEDs based on the underlying tissue. The biosensor 100 may adjust processing of the data. For example, an absorption coefficient may be adjusted when determining a concentration level of a substance based on Beer-Lambert principles due to the characteristics of the underlying tissue.

In addition, the calibrations utilized by the biosensor 100 may vary depending on the positioning of the biosensor. For example, the calibration database may include different table or other correlations between R values and concentration level of a substance depending on position of the biosensor. Due to the different density of tissue and vessels, the R value obtained from measurements over an abdominal area may be different than measurements over a wrist or forehead or fingertip. The calibration database may thus include different correlations of the R value and concentration level depending on the underlying tissue. Other adjustments may also be implemented in the biosensor 100 depending on predetermined or measured characteristics of the underlying tissue of the body part.

Embodiment—Respiration Rate and Heart Rate

Figure 9:
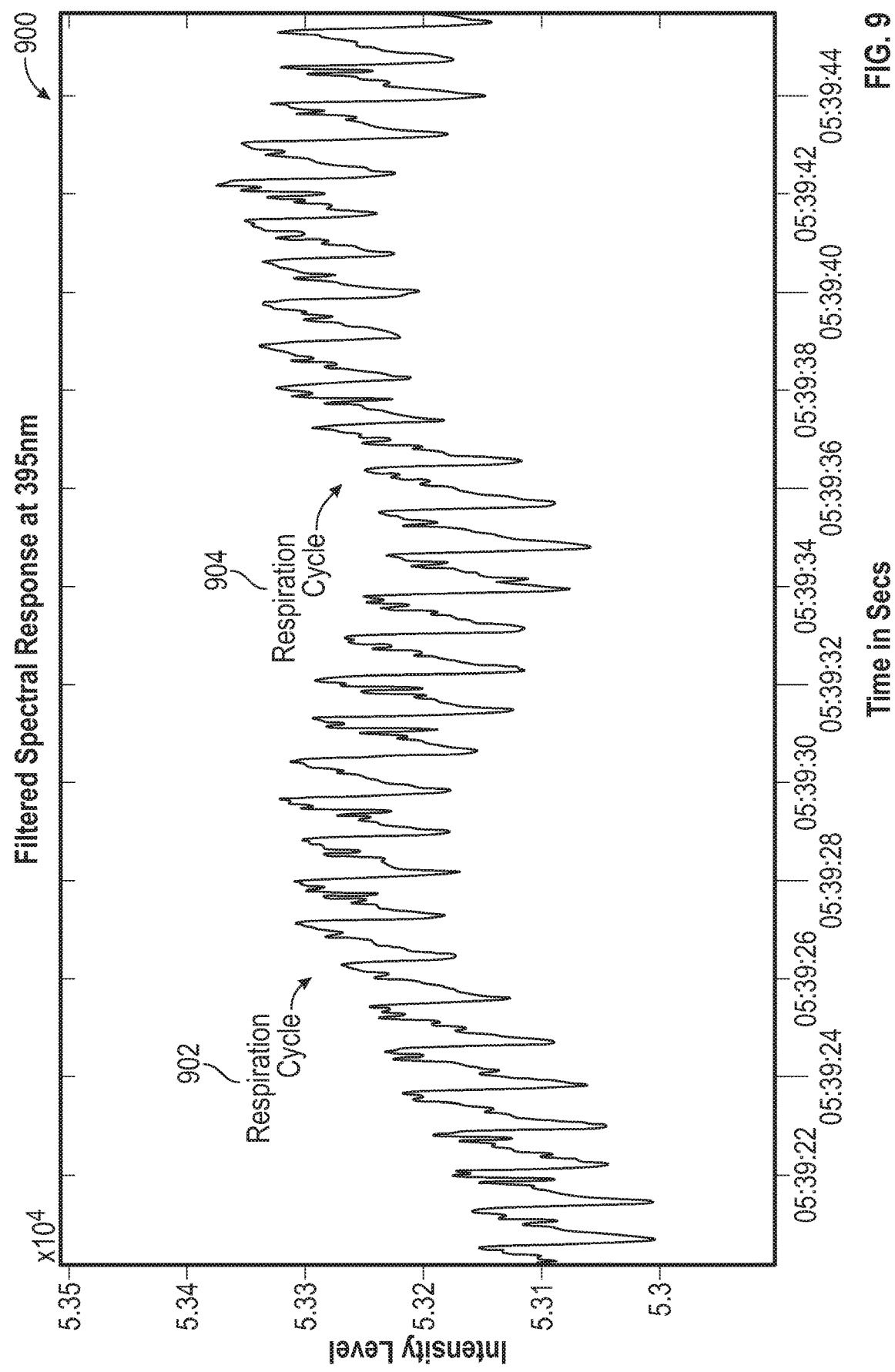
FIG. 9 illustrates a schematic drawing of an exemplary embodiment of a spectral response obtained using an embodiment of the biosensor from a user.

FIG. 9 illustrates a schematic drawing of an exemplary embodiment of a spectral response 900 obtained using an embodiment of the biosensor 100 from a user. The spectral response 900 was obtained at a wavelength of around 395 nm and is illustrated for a time period of about 40 seconds. The spectral response 900 was filtered using digital signal processing techniques to eliminate noise and background interference to obtain the filtered spectral response 900. A first respiration cycle 902 and a second respiration cycle 904 may be obtained by measuring the low frequency component or fluctuation of the filtered spectral response 900. From this low frequency component, the biosensor 100 may obtain a respiratory rate of a user from the spectral response 900. A heart rate may also be determined from the spectral response 900 as well. For example, the biosensor 100 may determine the time between diastolic points or between systolic points to determine a time period of a cardiac cycle.

Thus, a light source in the UV range may be used to determine heart rate and respiration rate. A light source in the UV range provides a good PPG signal for determining heart rate and respiration rate.

Figure 10:
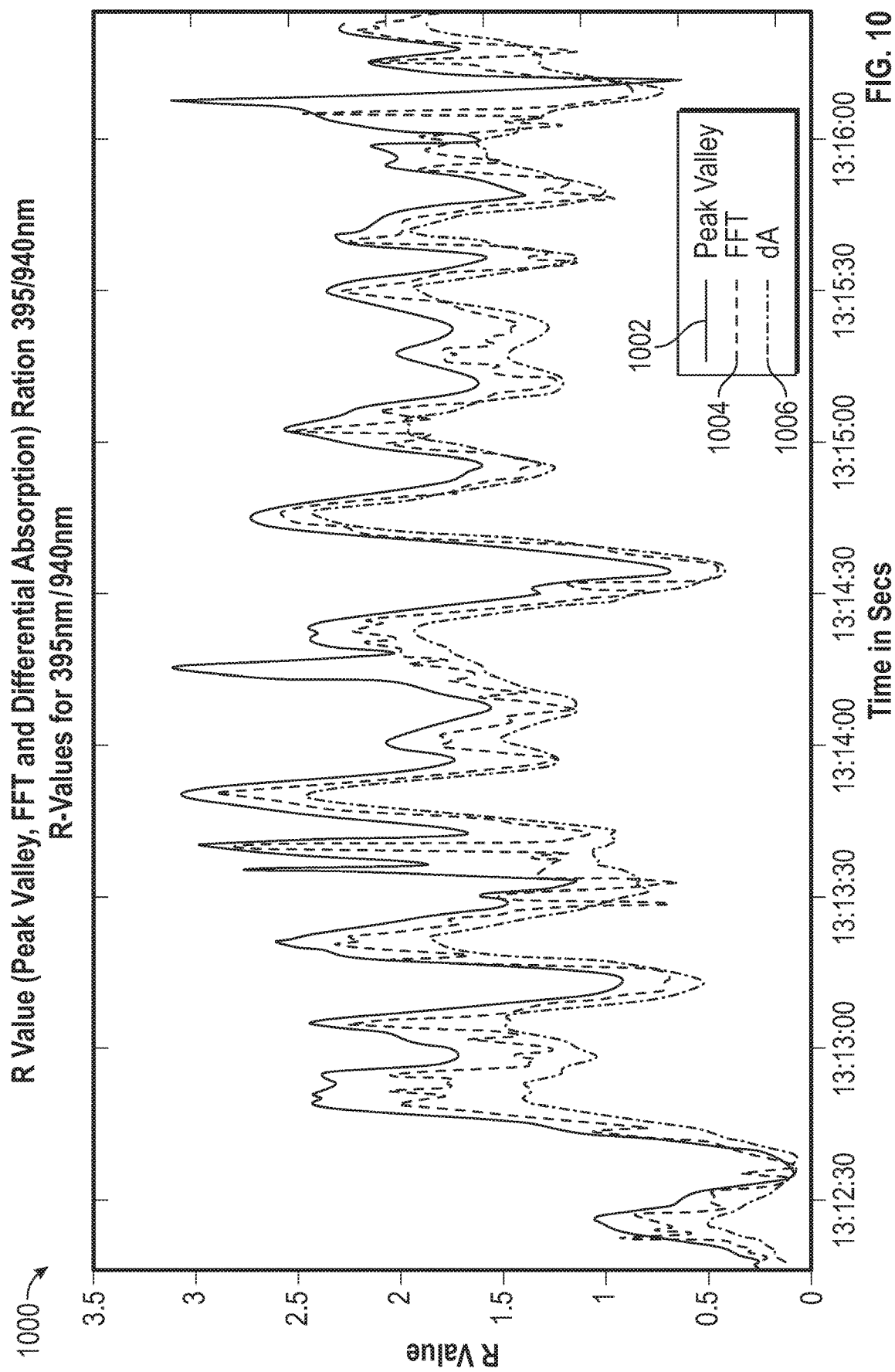
FIG. 10 illustrates a schematic drawing of an exemplary embodiment of results of R values determined using a plurality of methods.

FIG. 10 illustrates a schematic drawing of an exemplary embodiment of results of R values 1000 determined using a plurality of methods. The R values 1000 corresponding to the wavelengths of 395 nm/940 nm is determined using three methods. The R Peak Valley curve 1002 is determined using the Ratio $$R = \frac{L395}{L940}$$

as described hereinabove. The R FFT curve 1004 is obtained using FFT techniques to determine the $I_{DC}$ values and $I_{AC}$ component values of the spectral responses to determine the Ratio $$R = \frac{L395}{L940}.$$

The R differential absorption curve 1006 is determined using the shift in absorbance spectra as described hereinabove. As seen in FIG. 10, the determination of the R values using the three methods provides similar results, especially when averaged over a period of time. A mean or average of the R values 1002, 1004 and 1006 may be calculated to obtain a final R value or one of the methods may be preferred depending on the positioning of the biosensor or underlying tissue characteristics.

Figure 11:
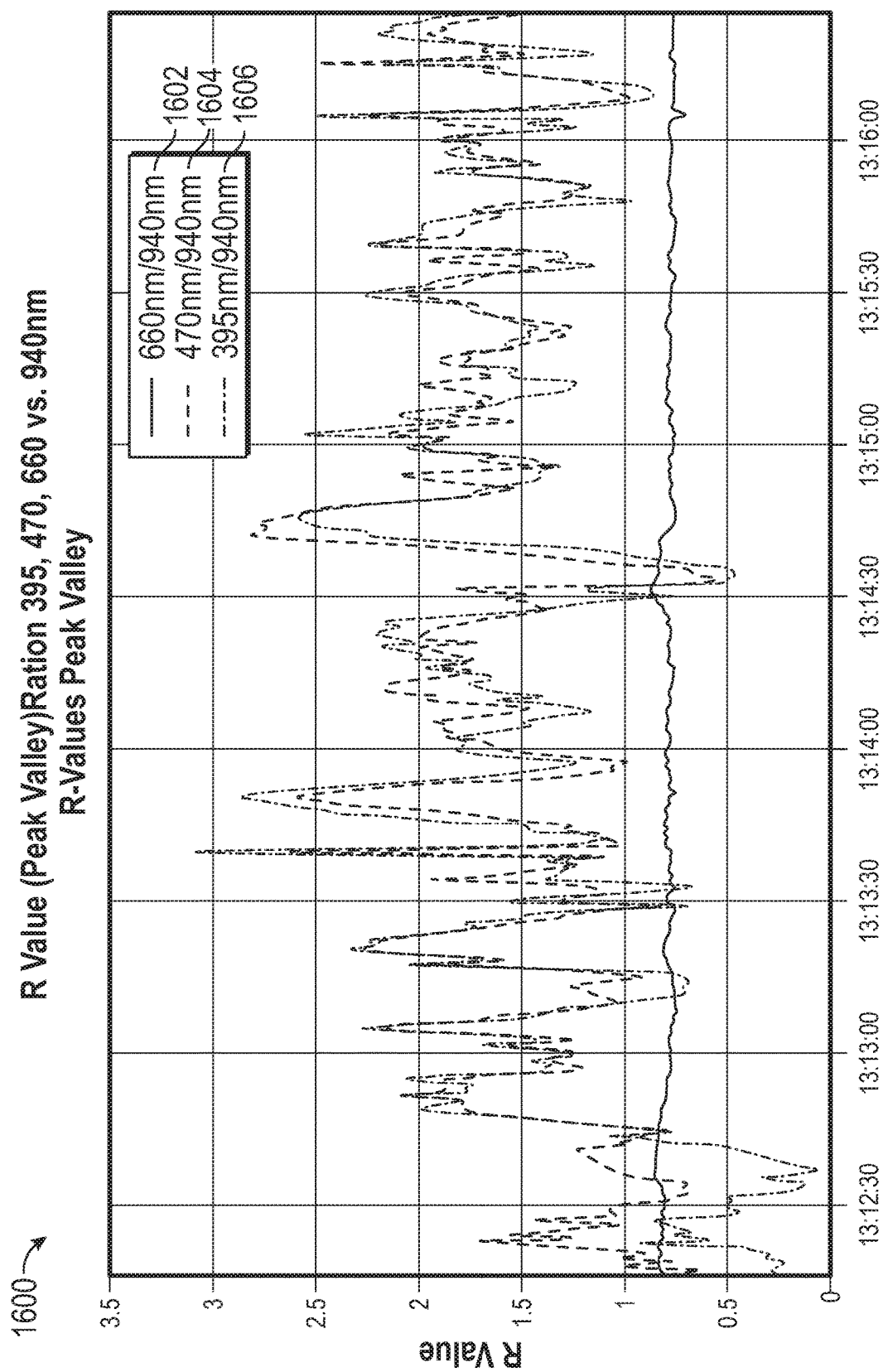
FIG. 11 illustrates a schematic drawing of an exemplary embodiment of results of R values for a plurality of wavelength ratios.

FIG. 11 illustrates a schematic drawing of an exemplary embodiment of results of R values 1600 for a plurality of wavelength ratios. The R values for 395 nm/940 nm 1606, the R values for 470 nm/940 nm 1604 and the R values for 660 nm/940 nm 1606 are shown over a time period of about 4 seconds.

Figure 12A:
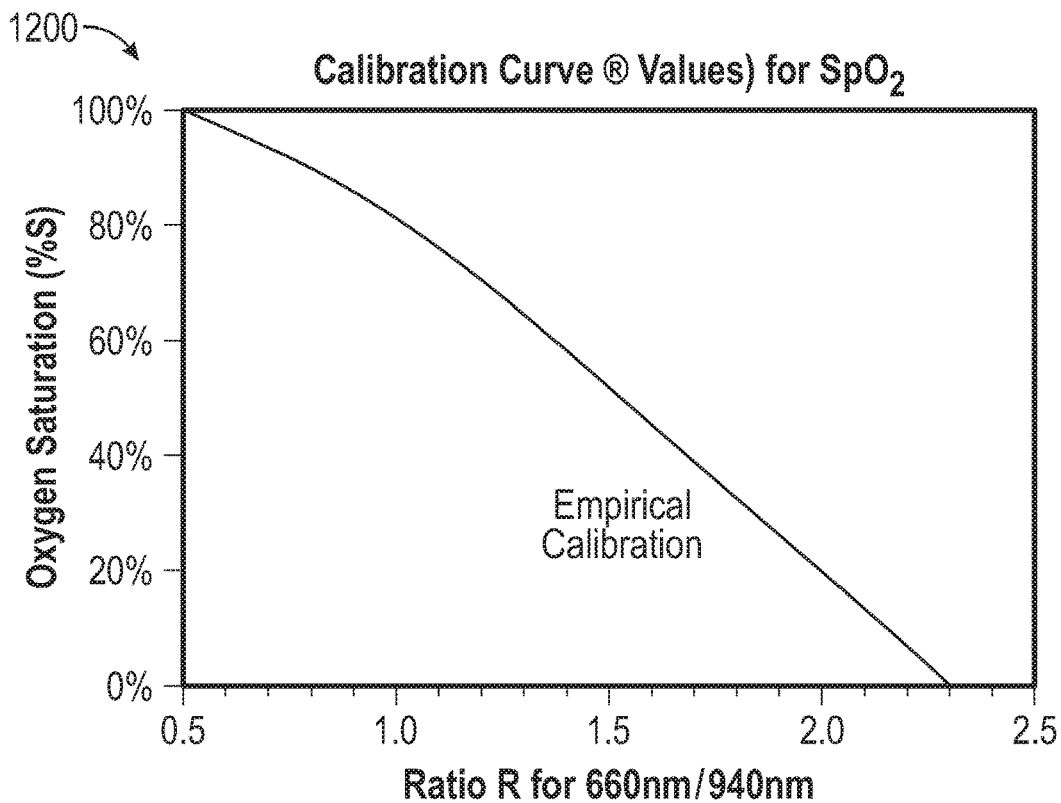
FIG. 12A illustrates a schematic drawing of an exemplary embodiment of an empirical calibration curve for correlating oxygen saturation levels ($SpO_2$) with R values.

FIG. 12A illustrates a schematic drawing of an exemplary embodiment of an empirical calibration curve 1200 for correlating oxygen saturation levels ($SpO_2$) with R values. The calibration curve 1200 may be included as part of the calibration database for the biosensor 100. For example, the R values may be obtained for $L_{660\ nm}/L_{940\ nm}$. In one embodiment, the biosensor 100 may use a light source in the 660 nm wavelength or in a range of +/−50 nm to determine $SpO_2$ levels, e.g. rather than a light source in the IR wavelength range. The 660 nm wavelength has been determined in unexpected results to have good results in measuring oxygenated hemoglobin, especially in skin tissue with fatty deposits, such as around the abdominal area.

Figure 12B:
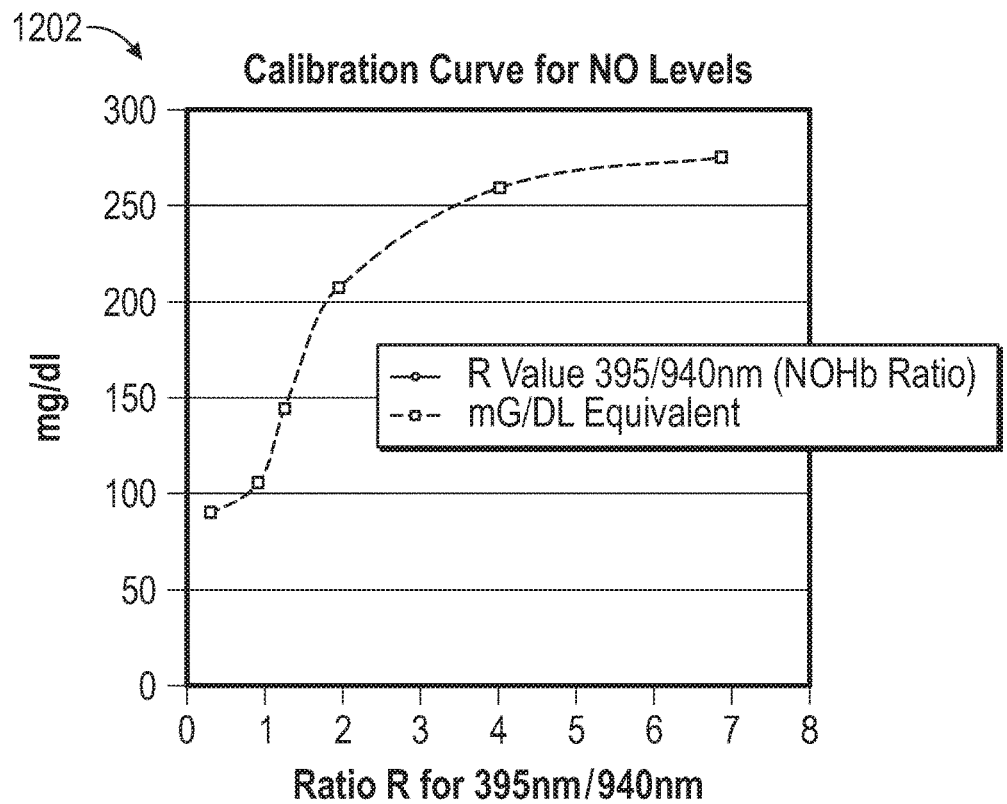
FIG. 12B illustrates a schematic drawing of an exemplary embodiment of an empirical calibration curve for correlating NO levels (mg/dl) with R values.

FIG. 12B illustrates a schematic drawing of an exemplary embodiment of an empirical calibration curve 1202 for correlating NO levels (mg/dl) with R values. The calibration curve 1702 may be included as part of the calibration database for the biosensor 100. For example, the R values may be obtained in clinical trials from measurements of $L_{395\ nm}/L_{940\ nm}$ and the NO levels of a general sample population. The NO levels may be measured using one or more other techniques for verification to generate such a calibration curve 1202. This embodiment of the calibration curve 1202 is based on limited clinical data and is for example only. Additional or alternative calibration curves 1202 may also be derived from measurements of a general population of users at one or more different positions of the biosensor 100. For example, a first calibration curve may be obtained at a forehead, another for an abdominal area, another for a fingertip, another for a palm, etc.

From the clinical trials, the L values obtained at wavelengths around 390 nm (e.g. 380-410) are measuring nitric level (NO) levels in the arterial blood flow. The R value for $L_{390}/L_{940\ nm}$ may thus be used to obtain NO levels in the pulsating blood flow. From the clinical trials, it seems that the NO levels are reflected in the R values obtained from $L_{390\ nm}/L_{940\ nm}$ and wavelengths around 390 nm such as $L_{395\ nm}/L_{940\ nm}$ The NO levels may thus be obtained from the R values and a calibration database that correlates the R value with known concentration levels of NO.

In other embodiments, rather than $L_{\lambda 1}$=390 nm, the L value may be measured at wavelengths in a range from 410 nm to 380 nm, e.g., as seen in the graphs wherein $L_{\lambda 1}$=395 nm is used to obtain a concentration level of NO. In addition, $L_{\lambda 2}$ may be obtained at any wavelength at approximately 660 nm or above. Thus, R obtained at approximately $L\lambda 1=380$ nm-400 nm and $L\lambda 2 \geq 660$ nm may also be obtained to determine concentration levels of NO.

In an embodiment, the concentration level of NO may be correlated to a diabetic risk or to blood glucose levels using a calibration database.

Embodiment—Detection of a Risk of Sepsis or an Infection Based on NO Levels

In an embodiment, the biosensor 100 may detect a risk of sepsis using NO concentration levels. In this embodiment, an R value derived from $L_{395}$ and $L_{940}$ is used to determine an NO measurement though other thresholds may be obtained using other NO measurements, such as $R_{390/940}$ or $L_{390}$. In the clinical trials herein, the $R_{395/940}$ value for a person without a sepsis condition was in a range of 0.1-8. In addition, it was determined that the $R_{395/940}$ value of 30 or higher is indicative of a patient with a sepsis condition and that the $R_{395/940}$ value of 8-30 was indicative of a risk of sepsis in the patient. In general, the $R_{3951940}$ value of 2-3 times a baseline of the $R_{395/940}$ value was indicative of a risk of sepsis in the patient. These ranges are based on preliminary clinical data and may vary. In addition, a position of the biosensor, pre-existing conditions of a patient or other factors may alter the numerical values of the ranges of the $R_{3951940}$ values described herein.

The R values are determined by using a wavelength in the UV range with high absorption coefficient for NO, e.g. in a range of 380 nm-410 nm. These R values have a large dynamic range from 0.1 to 300 and above. The percentage variance of R values in these measurements is from 0% to over 3,000%. The R values obtained by the biosensor 100 are thus more sensitive and may provide an earlier detection of septic conditions than blood tests for serum lactate or measurements based on MetHb.

For example, an optical measurement of MetHb in blood vessels is in a range of 0.8-2. This range has a difference of 1.1 to 1.2 between a normal value and a value indicating a septic risk. So these measurements based on MetHb have less than a 1% percentage variance. In addition, during a septic condition, MetHb may become saturated due to the large amount of NO in the blood vessels. So, an optical measurement of MetHb alone or other hemoglobin species alone is not able to measure these excess saturated NO levels. The R values determined by measuring NO level directly using a wavelength in the UV range are thus more sensitive, accurate, have a greater dynamic range and variance, and provide an earlier detection of septic conditions.

A baseline NO measurement in blood vessels of a healthy general population is obtained. For example, the biosensor 100 may obtain R values or other NO measurements using the biosensor 100. For example, the biosensor 100 may measure an $L_{395}$ value or determine SpNO % based on an R value for a general population over a period of time, such as hours or days. These NO measurements are then averaged to determine a baseline NO measurement. The NO measurement in blood vessels is then obtained for a general population with a diagnosis of sepsis. For example, the biosensor 100 may obtain R values or other NO measurements (such as an $L_{395}$ value or SpNO %) for patients diagnosed with sepsis using traditional blood tests, such as serum lactate blood tests. The biosensor 100 may monitor the patients throughout the diagnosis and treatment stages. The NO measurements are then averaged to determine a range of values that indicate a septic condition.

Predetermined thresholds may then be obtained from the NO measurements. For example, a threshold value indicative of a non-septic condition may be obtained. A threshold value for a septic condition may also be obtained. The biosensor 100 is then configured with the predetermined thresholds for the NO measurement.

The predetermined thresholds may be adjusted based on an individual patient's pre-existing conditions. For example, a patient with diabetes may have lower R values. A baseline NO value for a patient may also be determined based on monitoring of the patient during periods without infections. The predetermined thresholds stored in the bio sensor 100 may then be adjusted based on any individual monitoring and/or pre-existing conditions.

In addition, the predetermined thresholds may be determined and adjusted based on positioning of the biosensor 100. For example, different R values or other NO measurements may be obtained depending on the characteristics of the underlying tissue, such as tissue with high fatty deposits or with dense arterial blood flow. The thresholds and other configurations of the biosensor 100 may thus be adjusted depending on the underlying skin tissue, such as a forehead, chest, arm, leg, finger, abdomen, etc.

Embodiment—Detection of Other Conditions Based on NO Levels

Diabetic conditions may result in lower than normal NO levels. Based on R values, the biosensor 100 may determine a base insulin resistance factor based on the value $R_{\lambda 1,\lambda 2}$ that indicates a diabetic risk, as described in more detail in The present application claims priority under 35 U.S.C. § 120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein. For example, from unexpected results of clinical trials, an R value was obtained at approximately $L_{\lambda 1}=390$ nm and $L_{\lambda 2}=940$ nm by a biosensor 100 from a fingertip of a patient during a period of fasting, e.g. prior to ingestion of food or liquids. It was shown that such an $R_{390/940}$ value of less than 1 (e.g., approximately 0.5) indicated that a person has diabetes or early onset of diabetes. An $R_{390/940}$ value of 2 or above indicated that a person has a lower risk of a diabetes diagnosis. An $R_{390/940}$ value in the 5-6 range indicated no current risk of diabetes. Thus, based on the clinical trials, a non-invasive, quick 1-2 minute test produced an indicator of diabetes or diabetic risk in a person. In addition, an $R_{390/940}$ value may measure an insulin response of the patient after caloric intake over a measurement period. These unexpected results have advantages in early detection of diabetic risk and easier, non-invasive monitoring of insulin response and glucose levels. Though 390 nm and 940 nm were used in this embodiment, another first wavelength with a high absorption coefficient for NO and another second wavelength with a lower absorption coefficient may be used.

In another embodiment, carbon monoxide poisoning may result in higher than normal NO levels. Other compounds may also cause unsafe levels of NO in blood vessels, such as lidocaine and nitrates such as nitroglycerine, nitric oxide, or water sources contaminated by runoff containing nitrogen based fertilizers, anti-malaria drug dapsone, benzocaine, cyanide, anesthesia, nitroglycerin, nitrate drugs, water contaminated with nitro based fertilizers, landocaine, etc. The biosensor 100 may operate in one or more modes to detect or provide a warning of abnormal NO levels that may indicate one or more of these conditions.

In another embodiment, post-traumatic stress disorder (PTSD) may result in higher than normal NO levels. There are several reports that increased oxidative stress may be a factor in the evolution of some enduring neurological and psychiatric disorders and PTSD (Bremner, 2006). Stress, a risk factor for developing PTSD, evokes a sustained increase in nitric oxide synthase (NOS) activity that can generate excessive amounts of nitric oxide (Harvey et al., 2004). Oxidation of nitric oxide produces peroxynitrite that is very toxic to nerve cells (Ebadi et al., 2001), and elevated levels of peroxynitrite and its precursor nitric oxide have been observed in patients with PTSD. (Tezcan et al., 2003). The article by Kedar N. Prasad and Stephen C. Bondy, entitled, "Common biochemical defects linkage between post-traumatic stress disorders, mild traumatic brain injury (TBI) and penetrating TBI," Brain Research, Volume 1599, Pages 103-114, Mar. 2, 2015, and incorporated by reference herein, describes the elevation of nitric oxide NO that may indicate PTSD. The biosensor 100 may operate in one or more modes to detect or provide a warning of abnormal NO levels that may indicate PTSD.

In another embodiment, concussions, mild traumatic brain injury (TBI) and penetrating TBI, may also result in abnormal NO levels. The article by James H. Silver, entitled, "Inorganic Nitrite as a Potential Therapy or Biomarker for Concussion," J. Neurol Neurophysiol, Volume 7, Issue 2 (April 2016), and incorporated by reference herein, describes an abnormal pattern of nitric oxide NO levels after a concussion. For example, it has been observed that a rapid increase in nitric oxide occurs within minutes following head injury, followed by a decline to below baseline within hours. The biosensor 100 may monitor NO levels after a head trauma and detect this sudden increase and then reduction below baseline in NO levels. In use, a baseline level of NO may be determined for a user during normal conditions. After a potential head injury, the user is then monitored by the biosensor 100 for changes from this baseline level of NO. This process may be performed, e.g., for sideline evaluation of potentially concussed athletes. Thus, the biosensor 100 may operate in one or more modes to monitor NO levels and provide a warning of abnormal NO levels that may indicate a concussion or TBI.

Embodiment—Measurements of Other Substances in Blood Flow

Using similar principles described herein, the biosensor 100 may measure concentration levels or indicators of other substances in pulsating blood flow. For example, absorption coefficients for one or more frequencies that have an intensity level responsive to concentration level of substance may be determined. The biosensor 100 may then detect the substance at the determined one or more frequencies as described herein and determine the concentration levels using the Beer-Lambert principles and the absorption coefficients. The L values and R values may be calculated based on the obtained spectral response. In one aspect, the biosensor 100 may detect various electrolyte concentration levels or blood analyte levels, such as bilirubin and sodium and potassium. In another aspect, the biosensor 100 may detect sodium NACL concentration levels in the arterial blood flow to determine dehydration.

In yet another aspect, the biosensor 100 may be configured to detect proteins or abnormal cells or other elements or compounds associated with cancer. In another aspect, the PPG sensor may detect white blood cell counts to determine a risk of infection. The biosensor 100 may also detect blood pressure, peripheral oxygen ($SpO_2$ or $SaO_2$) saturation, heart rate, respiration rate or other patient vitals. Because blood flow to the skin can be modulated by multiple other physiological systems, the PPG sensor 110 may also be used to monitor breathing, hypovolemia, and other circulatory conditions.

For example, the biosensor 100 may also determine alcohol levels in the blood using wavelengths at approximately 390 nm and/or 468 nm. For example, an $R_{468,940}$ value (obtained from a ratio of $L_{468\ nm}$ and $L_{940\ nm}$) may be used as a liver enzyme indicator, e.g. P450 enzyme indicator. The P450 liver enzyme is generated in response to alcohol levels. Thus, the measurement of the spectral response for the wavelength at approximately 468 nm may be used to obtain blood alcohol levels from the concentration levels of P450 and a calibration database.

In another embodiment, an $R_{592,940}$ value (obtained from a ratio of $L_{592\ nm}$ and $L_{940\ nm}$) may be used as a digestive indicator to measure digestive responses, such as phase 1 and phase 2 digestive stages. In another aspect, the biosensor 100 may detect white blood cell counts or concentration levels in arterial blood flow using similar PPG techniques. The presence of white blood cell counts may indicate the presence of infection.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100. Since the biosensor 100 may operate in multiple frequencies, various health monitoring tests may be performed concurrently.

In another aspect, the biosensor 100 may measure creatinine levels using the PPG circuit by detecting a spectral response around 530 nm. Creatinine is produced by the kidneys and various factors can affect the kidney production levels of creatinine. The biosensor 100 may detect spectral responses, e.g. at 530 nm and 940 nm or in ranges+/−20 nm and obtain an $R_{530/940}$ value. The biosensor 100 may then provide an indicator of a concentration level of creatinine in blood flow based on the $R_{530/940}$ value and a calibration database.

In another aspect, the biosensor 100 may detect white blood cell counts in arterial blood flow using similar PPG techniques. The presence of white blood cell counts may also be used as an indicator of the presence of an infection.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100.

In another aspect, the biosensor 100 may detect cholesterol levels, such as LDL-Cholesterol, HDL-Cholesterol, and Triglycerides. In a first embodiment, the biosensor 100 detects cholesterol from PPG signals around a first wavelength with a high absorption coefficient for cholesterol, such as 440 nm or 550 nm. The wavelengths 440 nm and 550 nm may be used by the biosensor 100 to detect cholesterol as well as 468 nm. PPG signals around a second wavelength with a lower absorption coefficient for cholesterol are also obtained, such as 880 nm or 940 nm. A value R using the first and second wavelengths, such as $R_{440/940}$ or $R_{550/940}$, is then obtained. A correlation between the value R and a level of cholesterol is stored in a calibration database.

In another embodiment, the cholesterol levels, such as LDL-Cholesterol, HDL-Cholesterol, and Triglycerides, may be determined from a shape of the PPG waveforms. The characteristic features of the shape of the PPG waveform are correlated with a cholesterol level. The biosensor 100 may implement both methods for detection of cholesterol levels, e.g. using both an R value and characteristic features of the shape of the PPG waveform.

In one or more modes of operation, the biosensor 100 may thus be configured to detect one or more of these other substances in addition to or alternatively from NO levels in blood flow.

Figure 13:
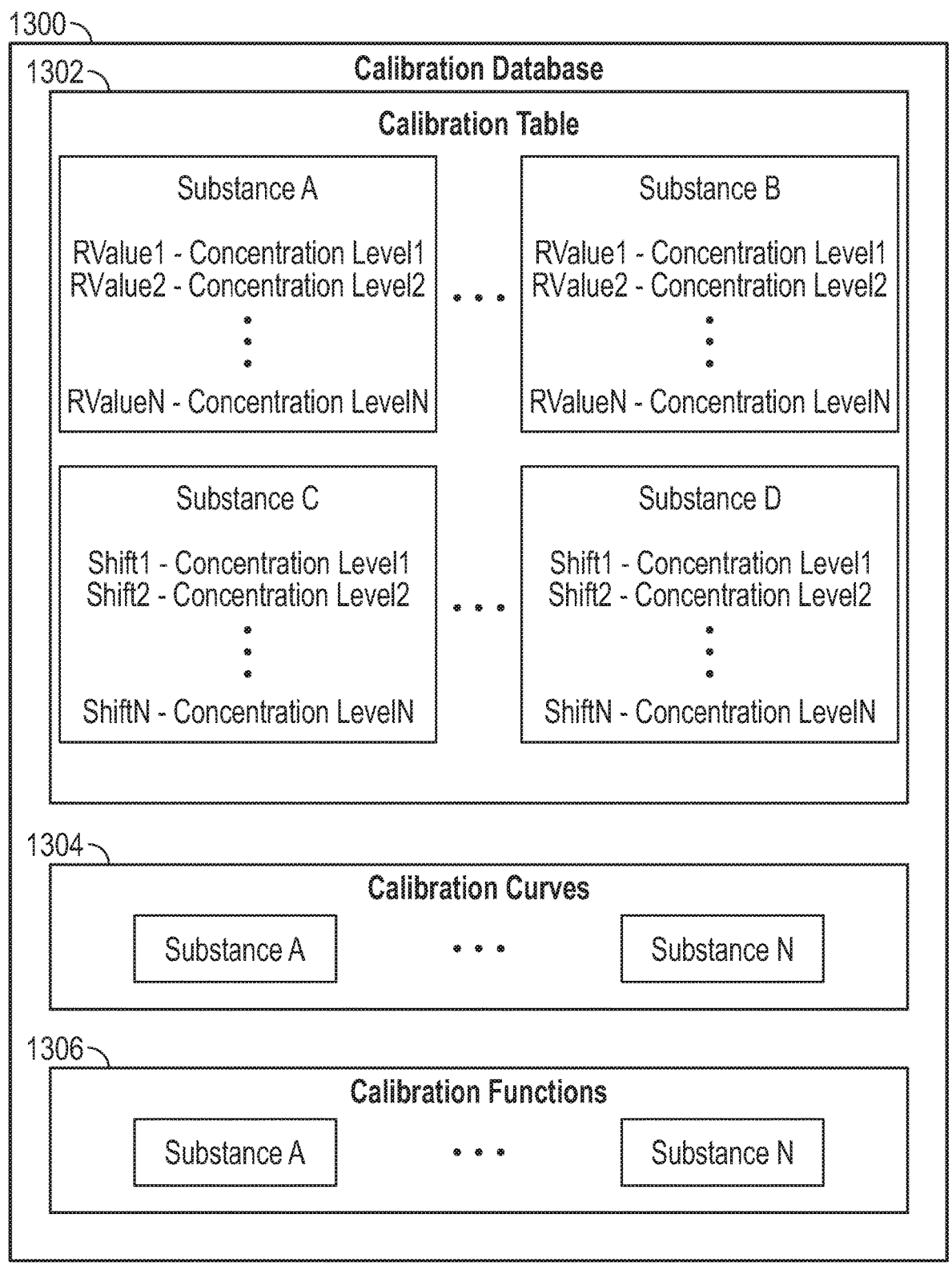
FIG. 13 illustrates a schematic block diagram of an embodiment of a calibration database.

FIG. 13 illustrates a schematic block diagram of an embodiment of a calibration database 1300. The calibration database 1300 includes one or more calibration tables 1302, calibration curves 1304 or calibration functions 1306 for correlating obtained values to concentration levels of one or more substances A-N. The concentration level of the substances may be expressed in the calibration tables 1302 as units of mmol/liter, as a saturation level percentage (SpNO %), as a relative level on a scale (e.g., 0-10), etc.

The calibration database 1300 may also include one or more calibration tables for one or more underlying skin tissue types. In one aspect, the calibration database 1300 may correlate an R value to a concentration level of a substance for a plurality of underlying skin tissue types.

In another aspect, a set of calibration tables 1302 may correlate an absorption spectra shift to a concentration level of one or more substances A-N. For example, a first table may correlate a degree of absorption spectra shift of oxygenated hemoglobin to NO concentration levels. The degree of shift may be for the peak of the absorbance spectra curve of oxygenated hemoglobin from around 421 nm. In another example, the set of table 1302 may correlate a degree of absorption spectra shift of deoxygenated hemoglobin to NO concentration levels. The degree of shift may be for the peak of the absorbance spectra curve of deoxygenated hemoglobin from around 430 nm.

The calibration database 1300 may also include a set of calibration curves 1304 for a plurality of substances A-N. The calibration curves may correlate L values or R values or degree of shifts of spectral data to concentration levels of the substances A-N.

The calibration database 1300 may also include calibration functions 1306. The calibration functions 1306 may be derived (e.g., using regressive functions) from the correlation data from the calibration curves 1304 or the calibration tables 1302. The calibration functions 1806 may correlate L values or R values or degree of shifts in spectral data to concentration levels of the substances A-N for one or more underlying skin tissue types.

The biosensor 100 may transmit the health information over a wide area network, such as a cellular network, to a third party service provider, such as a health care provider or emergency service provider.

PPG Signal as a Biometric

In an embodiment, the shape of a PPG waveform is measured and used as a unique biometric measurement to identify a user. The PPG waveforms of a user are unique, e.g. the PPG waveforms of a subject are different from the PPG waveforms of other subjects. The different characteristic features related to the shape of the PPG waveform are described, e.g., in the article, "On the Analysis of Fingertip Photoplethysmogram Signals," by Mohamed Elgendi, Current Cardiology Reviews, Volume 8, pages 14-25 (2012), which is hereby incorporated by reference herein, and in the article, "Feasibility of Authenticating Medical Data Using Photoplethysmography (ppg) as Signature Mark," by V Bhavana, Vidya M J, Padmaja K. V, Int'l J. of Adv. Research in CSSE, Volume 4, Issue 1, (January 2014), which is hereby incorporated by reference herein.

For example, a typical PPG waveform includes a systolic peak, a diastolic peak, dicrotic notch, and pulse width. Other characteristic features include pulse area, pulse interval, peak to peak interval, augmentation index, crest time, etc. Other characteristic features may be extracted from a first or second derivative of the PPG waveform. For example, various ratios may be derived from a second derivate of the PPG waveform, e.g., such as the early systolic negative wave to the early systolic positive wave (Ratio b/a). Thus, the PPG waveform features or characteristics related to the shape of the PPG waveform may include one or more of Sys Amp, Pulse Width, Pulse Area, Peak to Peak interval, pulse interval, augmentation index, artery stiffness, diastolic Point, delta T, crest time, and the Ratios: B/A, C/A, D/A, E/A, APG described in Elgendi 2012. These and other characteristic features related to the shape of the PPG waveform (including its derivatives) may be obtained and compared with one or more stored characteristics of PPG waveforms. Since PPG waveforms for a subject may vary over time, the stored PPG waveform and its characteristics for a user may need to be updated periodically.

In an embodiment, the characteristic features related to the shape of the PPG waveform are used for biometric identification of a user. For example, a biosensor 100 obtains a spectral response including PPG waveforms for a known or authorized user over one or more cardiac cycles. Various characteristics related to the shape of the PPG waveform (including its derivatives) are determined and stored in a database. The stored characteristics of the PPG waveform may then be compared with a measured PPG waveform to authenticate the user in the future.

Figure 14:
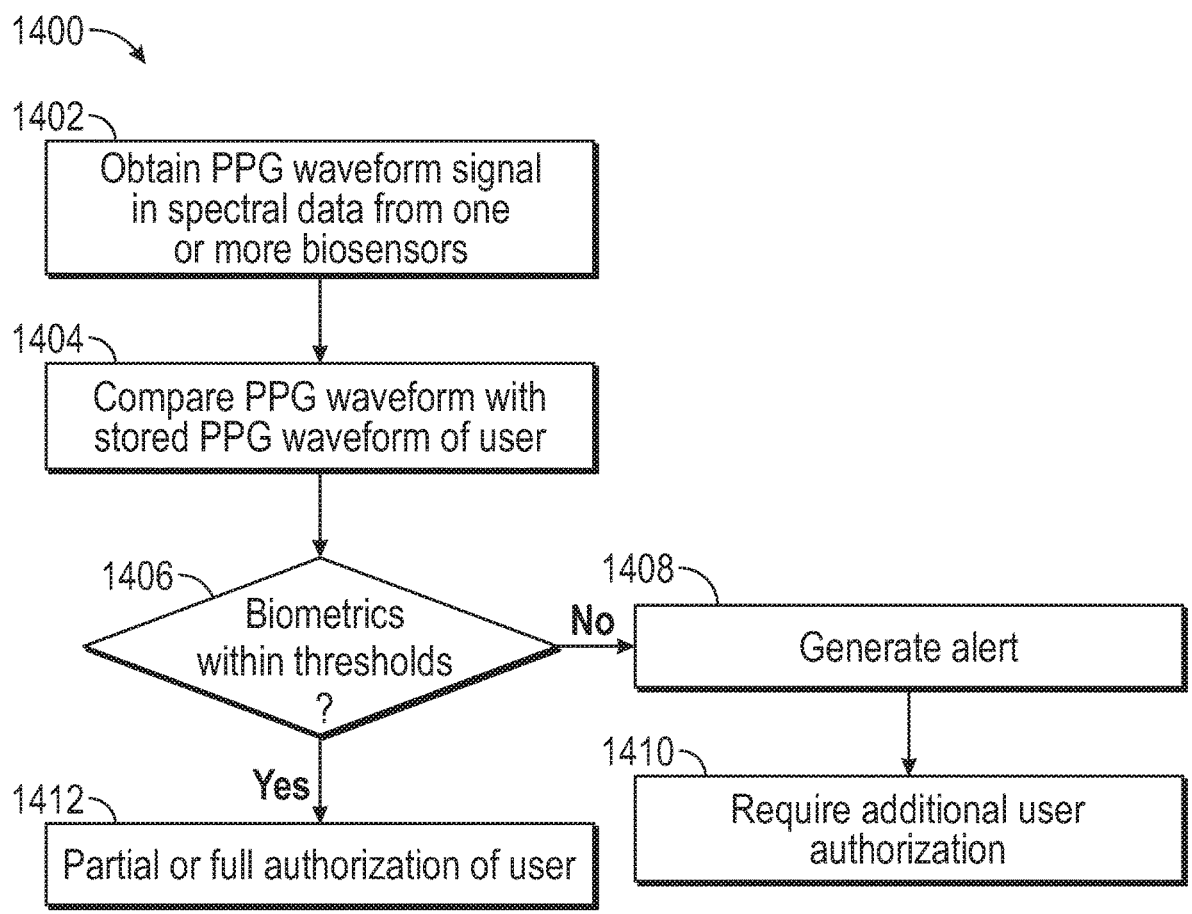
FIG. 14 illustrates a logical flow diagram of a method 1400 for authentication using a PPG waveform as a biometric measurement.

FIG. 14 illustrates a logical flow diagram of a method 1400 for authentication using a PPG waveform as a biometric measurement. The PPG waveform signal of a user is measured over one or more cardiac cycles at 1402. For example, the PPG waveform may be measured using one or more biosensors 100. Various characteristics of the PPG waveform are determined and compared with stored characteristics of one or more authorized users at 1404. Alternatively, a pattern recognition process may be performed to compare the PPG waveform with a stored PPG waveform of a user at 1404. It is then determined whether the PPG waveform is authenticated, e.g., whether the characteristics of the measured PPG waveform is within predetermined thresholds of stored characteristics of PPG waveforms of an authorized user at 1406.

If not, an alert may be generated at 1408. The authentication system may prevent activation of one or more functions of a device, e.g. such as a smart phone, entry to a door, etc. For example, the authentication system may prevent ignition of a vehicle or opening of a door for entry. The authentication system may require additional user authorization at 1410 prior to activation of the one or more functions of the device. For example, a unique code may need to be entered or fingerprint verification performed or other type of authorization completed.

When the obtained biometric measurements are within predetermined thresholds, full or partial authorization may be provided to activate one or more functions of the device. For example, an authentication message may be generated or an authorization performed for unlocking of a device. One or more steps of the authentication or identification process may be performed by a neural network or machine learning algorithm as described in more detail herein.

Embodiment—Detection of Blood Group

The biosensor 100 described herein may be configured to assess the blood group of a patient, human or animal, using the PPG circuit 110. Blood type or group is represented by the ABO and Rh(D) systems. The A, B, O, AB blood type of a person depends on the presence or absence of two genes, A and B. These genes determine the configuration of the red blood cell surface. A person who has two A genes has red blood cells of type A. A person who has two B genes has red cells of type B. If the person has one A and one B gene, the red cells are type AB. If the person has neither the A nor the B gene, the red cells are type O. It is essential to match the ABO status of both donor and recipient in blood transfusions and organ transplants. In addition to the four main blood groups—A, B, AB and O, each group can either be RhD positive or RhD negative. Antigens are proteins on the surface of blood cells that can cause a response from the immune system. The Rh factor is a type of protein on the surface of red blood cells. Most people who have the Rh factor are Rh-positive. Those who do not have the Rh factor are Rh-negative. This means that in total there are eight main blood groups. The blood type of a patient exhibits different antigens present on the surface of red blood cells. The Rh factor is another type of protein on the surface of red blood cells.

In the last 30 years fully automated blood testing instruments have been developed and are in operation at blood centers and major hospitals. These instruments have advantages like high speed and sensitivity but they also require large size and high costs. These are major drawbacks. Development of a portable, low-cost, and sensitive instrument for blood typing is therefore required to make an on-site blood testing feasible. Aggulutination of RBCs (hemagglutination) is caused by an immune reaction between the RBCs and antibodies against the corresponding blood type. In conventional blood typing methods, hemagglutination caused by antibodies is detected by human eyes or by imaging techniques. Alternative methods of blood types using optical techniques have also been reported.

The optical properties of the different blood groups can be detected. The red blood cells comprise about 45% of the human blood. The color differences between the different blood groups are detectable. Thus, the optical differences between the different RBC groups (A, B, AB and O) can be determined using an optical sensor. For example, in the Armenian Journal of Physics, 2011, vol. 4, issue 3 pp. 165-168 shows a method for blood grouping detection using fiber optics. The basic premise of the method described is to use a laser operating at 820 nm to fire a series of pulses into a blood sample at 10 Khz, then using a photo diode, convert the optical variations back into electrical variations by amplifying, filtering, rectifying and feed the primary signal into a capacitor filter. This capacitor changes a voltage which is different for various blood groups. Since the different blood types have different optical spectrum characteristics, this method of fiber optic injection into a blood sample and then reading the approximate integration response of the corresponding signal shows a basic mathematical integration method is possible. However this method requires a raw blood sample and is expensive and time consuming.

The biosensor 100 described herein may be configured to assess the blood group of a patient using the PPG circuit 110. In an embodiment, the PPG circuit 110 emits a series of pulses at a patient's tissue to obtain a series of R values. The series or average of the series of R values is used to identify a blood type, e.g. the antigen group present or absent on blood cells. The PPG circuit 110 uses a series of pulses firing LED's at a rate of between 100-200 Hz to obtain a good heart rate signal. One or more of the following R values for 550/940 nm, 660/940 nm, and 880 nm/940 nm frequencies may be obtained over an integration of a series of heartbeats. Due to the division of the L values, the R value eliminates the input from the skin tissue and non-pulsating blood flow to isolate the input from the pulsating blood flow (venous or arterial). To determine a blood group, the R values may be obtained over a sample window, such as over a plurality of heartbeats. A blood group indicator may be derived from the values of the R ratio over the sample window. For example, an integration of the R values over the sample window may be determined and then the integrated R values used as the blood group indicator. The blood group indicator is then used to identify a blood group from one or more blood group reference tables.

For example, in order to enhance the data signal of a spectral response, the data signal in a spectral response over a series of heart beats is used for the sample window. The R value may be obtained over the sample window using spectral responses around a plurality of frequencies. The frequencies may include, e.g., 550, 660 and 880 nm frequencies or in ranges of wavelengths around such frequencies. In one embodiment, the frequencies include 530 and 590 nm and values for the ratio $R=L_{530}/L_{940}$ and $R=L_{590}/L_{940}$ are determined over the sample window. The values for the first $R_{530/940}$ ratio are then integrated across the sample window to determine an integrated R value as a first blood group indicator. The values for the second $R_{590/940}$ ratio are then integrated across the sample window to determine an integrated R value as a second blood group indicator. A simple integration algorithm for each individual frequency may be implemented to obtain the blood group indicators. In another embodiment, the values for the R ratios are averaged over the sample window. Other functions using the values of the R ratios over the sample window may be implemented to obtain one or more blood group indicators.

The obtained one or more blood group indicators are then used with a calibration table to identify a blood group of the patient, human or animal. For example, the calibration table includes a correlation of values or ranges of the one or more blood group indicators to blood group or blood type. The calibration table may be determined by obtaining the blood group indicator for a sample general population for each known blood type.

Figure 15:
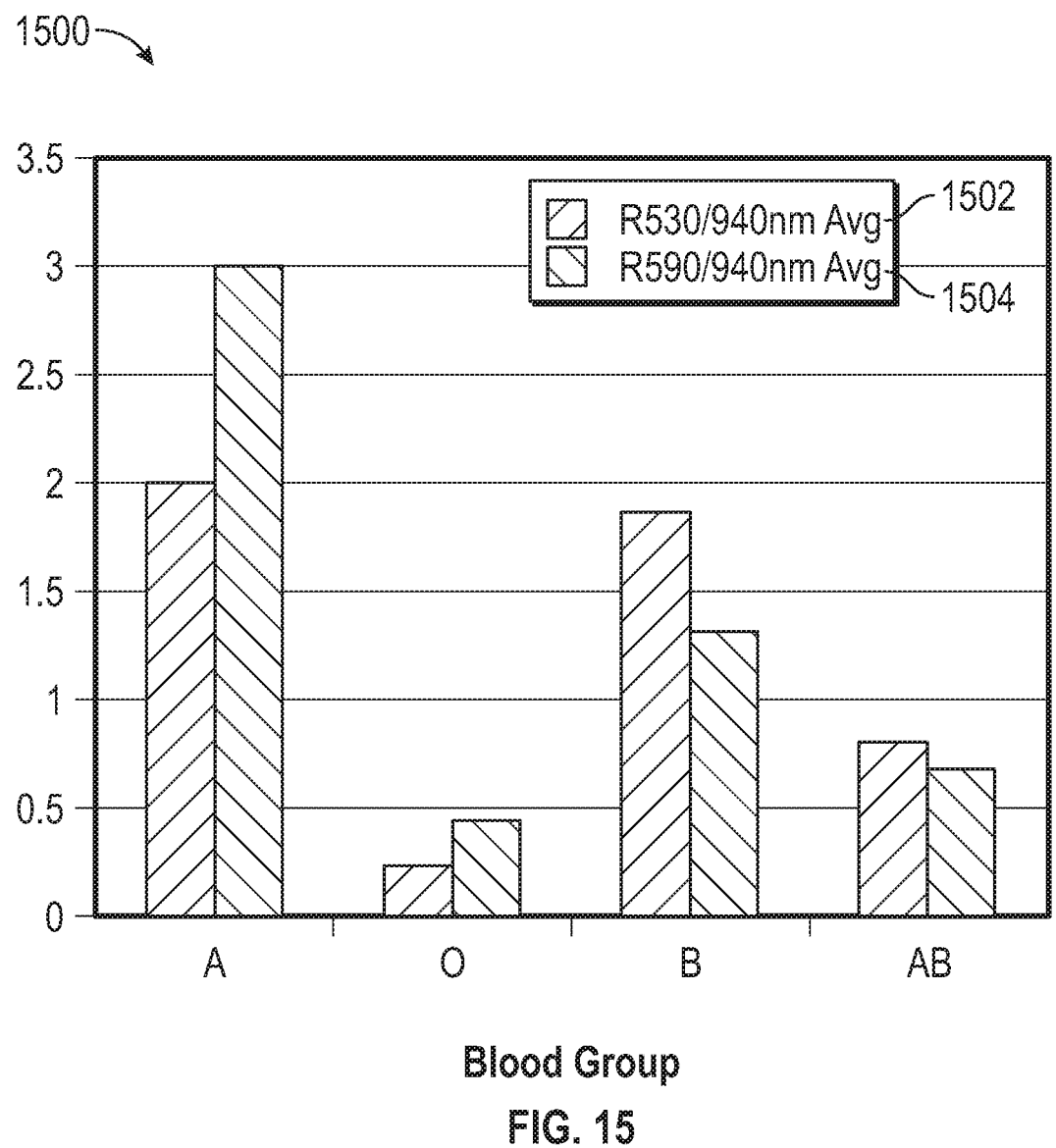
FIG. 15 illustrates a schematic drawing of an embodiment of a calibration table for blood groups.

FIG. 15 illustrates a schematic drawing of an embodiment of a calibration table 1500 for blood groups. The calibration table or blood group reference table 1500 includes an expected or know range of average values for R ratios for a plurality of the blood groups. The blood group reference table 1500 illustrates expected values for a plurality of blood group indicators for each blood group A, O, B, and AB. In this embodiment, the blood type indicators for the patient include an average $R_{530/940}$ value 1502 and an average $R_{530/940}$ value 1504. The expected average values for the blood group indicators of $R_{530/940}$ ratio 1502 and $R_{590/940}$ ratio 1504 are shown for each of the blood groups A, O, B and AB.

The measured average $R_{530/940}$ value and $R_{590/940}$ value may be compared to the blood group reference table 1500. Though the RH+ and RH− types are not shown in this blood group reference table 1500, a calibration graph or table may be used to determine the RH+ and RH− types of each Blood Groups A, B, AB and O. For example, the blood group A, B, AB and O may first be determined and then the RH+ and RH− types determined using the same or different blood type indicators. In another embodiment, the blood group A, B, AB and O and RH+ and RH− type may be determined using a same calibration table and blood type indicators. For example, values of the R ratio at 535 nm/940 nm may be used to detect either Rh+ or Rh−.

In another embodiment, though two blood type indicators are illustrated herein, three or more blood type indicators may be used to determine the blood type or a single blood type indicator may be used to determine the blood type. For example, a first blood type indicator may be determined and compared with the blood group reference table 1500. If the first blood type indicator fails to correlate with an expected value for a blood type, one or more additional blood type indicators may be obtained and compared with the blood group reference table 1500. In addition, though the blood group reference table 1500 illustrates a single expected value for each blood type indicator, the blood group reference table 1500 may indicate a range of expected values for one or more blood type indicators. The various R values indicate a presence of an antigen to identify a blood group of A, B, O or AB using the plurality of spectral responses. The biosensor 100 may use the same R values or different R values to determine a presence of another antigen within a blood group to identify an RH factor using the plurality of spectral responses. The biosensor 100 may thus be configured to determine a blood group A, B, O, AB and RH+ and RH− using one or more blood type indicators and a blood group reference table. A blood type indicator is obtained using values of an R ratio over a sample window. A different R ratio and blood type indicator may be used for comparison based on the blood group (such as, A, B, O, AB).

For example, an expected range of values for a first blood type indicator derived from a first R ratio may be listed for blood group A while an expected range of values for a second blood type indicator derived from a second different R ratio may be listed for blood group O. The biosensor 100 may obtain the first and/or second blood type indicators in series or parallel and use the calibration table to determine the blood type. The various calibration tables, curves or other correlations may be stored in the calibration database 1300. For example, the calibration table includes a correlation of values or ranges of the one or more blood group indicators to blood group or blood type. The calibration table may be determined by obtaining the blood group indicator for a sample general population for each known blood type.

One or more steps of the blood type identification process may be performed by a neural network or machine learning algorithm as described in more detail herein.

Embodiment—Detection of Blood Group Using Signal Quality Parameters

The spectral differences of the antigens present on the surface of red blood cells in different blood types affects the quality of the PPG signal. For example, the reflectance of different types of surfaces of the red blood cells affects the scattering of light transmitted from the PPG circuit 110. These differences in signal quality are measurable, especially in a reflectance PPG signal (vs. a transmissive PPG signal) due to the differing light scattering properties. In known solutions, an automatic gain filter or other digital signal processing compensates for the different qualities of the PPG signal.

However, when a uniform gain or filter is applied to the PPG signal from patients of different blood types, the differences in the signal strength and qualities of the PPG signal may be measured and used to determine the blood type. The different blood groups have different optical properties due to variances in the antigen groups on the surface of the red blood cells. Thus, the quality of the PPG signal quality is affected by the type of blood group due to the different antigens on the surface of the RBCs. Various parameters that measure signal quality or signal strength of the PPG signal may be determined and compared to predetermined values to determine the blood type. These differences in PPG signal quality are preferably determined at a similar gain or amplification.

There are various signal quality parameters that may be implemented to compare the differences in signal quality and strength of the PPG signal across blood types. For example, using a similar gain or amplification and other filtering or signal processing, the cross-correlation and auto-correlation of PPG signals, may be measured to determine different blood types. Other signal quality parameters may also be implemented to determine different blood types, such as a signal to noise ratio (SNR), skewness index ($S_{SQI}$), a kurtosis index ($K_{SQI}$), entropy ($E_{SQI}$), relative power, or other indices of signal quality or strength. An example of types of signal quality parameters that may be implemented herein are described in, Elgendi, Mohamed, "Optimal Signal Quality Index for Photoplethysmogram Signals." Ed. Gou-Jen Wang. Bioengineering 3.4 (2016): 21, which is hereby incorporated by reference herein. The various signal quality parameters measure the signal quality and/or signal strength of the PPG signal. A signal quality parameter may be implemented as another blood type indicator.

Figure 16:
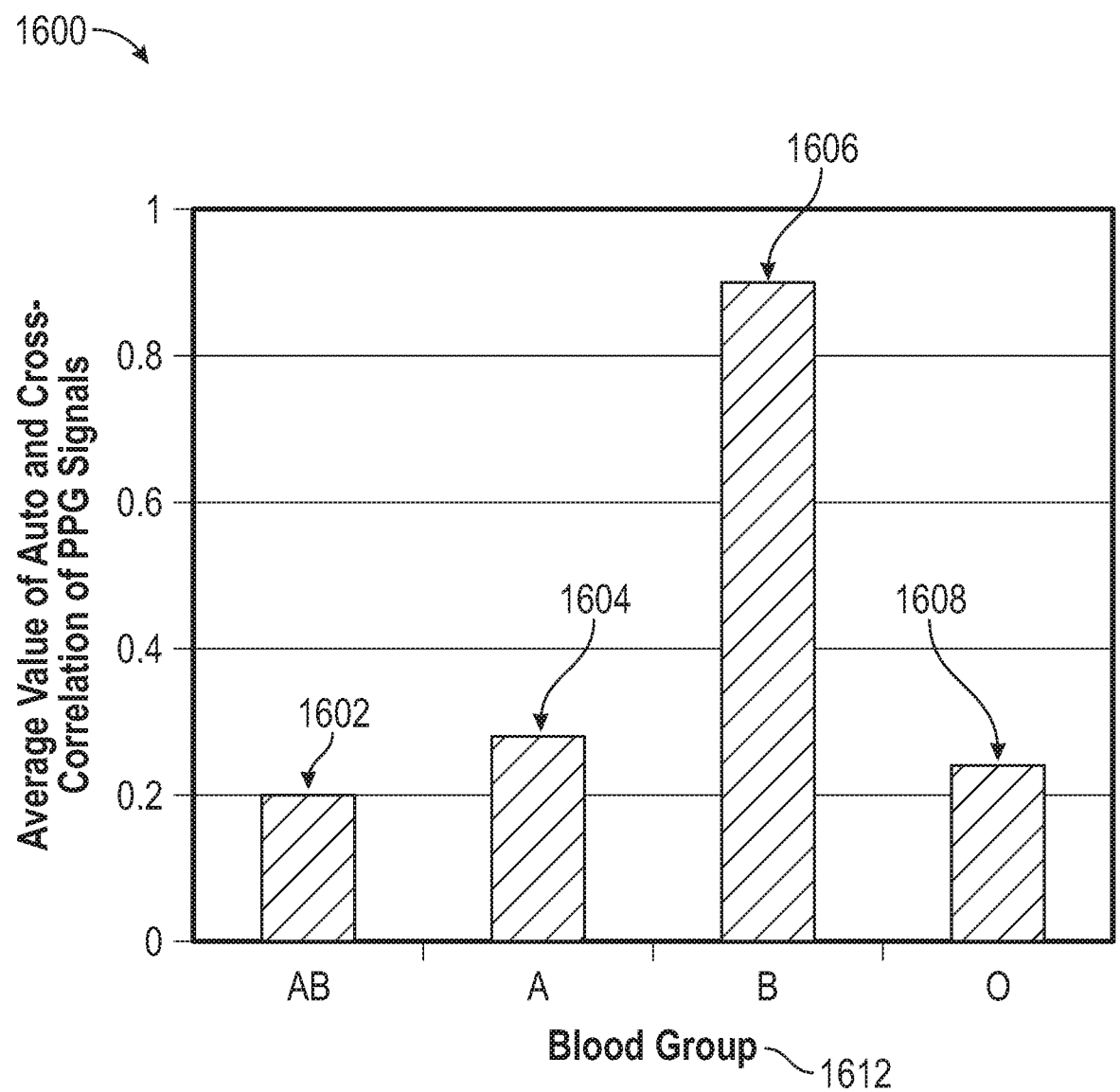
FIG. 16 illustrates a schematic graph of an embodiment of predetermined signal quality parameters for obtaining a blood type in a patient.

FIG. 16 illustrates a schematic graph 1600 of an embodiment of predetermined signal quality parameters for obtaining a blood type in a patient. In this graph 1600, the average values 1610 of the auto and cross-correlations of PPG signals from various blood types 1612 is illustrated. The predetermined average values include, e.g., an approximate 0.2 average for AB Blood group 1602, an approximate 0.3 average for A blood group 1604, an approximate 0.9 average for B blood group 1606, and an approximate 0.23 average for 0 blood group 1608. Though the approximate averages are shown, a range of average values may be predetermined for the different blood groups. Alternatively, a mean, threshold value, or other parameter derived from the auto or cross-correlation functions may be implemented.

In use, PPG signals are obtained from a patient at a plurality of wavelengths. The state of the gain controller is changed or disabled. For example, the automatic gain control is disabled, and a uniform gain or no gain is applied to the PPG signal across patients when determining blood group. In general, the PPG signal should have no gain applied or a similar gain applied for consistent measure and comparison of signal quality for blood typing.

One or more signal quality parameters are measured using one or more PPG signals at one or more wavelengths. The signal quality parameters may relate to signal quality and/or signal strength of the PPG signal. For example, a signal to noise ratio of a PPG signal with a wavelength in an IR range may be determined. An average value of an auto-correlation of a PPG signal may be determined or a cross-correlation of two PPG signals at two different wavelengths may be determined. Other signal quality parameters may also be implemented to determine different blood types, such as a skewness index ($S_{SQI}$), a kurtosis index ($K_{SQI}$), entropy ($E_{SQI}$), relative power, or other indices of signal quality or strength.

Though the signal quality parameter of the PPG signal $I_{AC+DC}$ is illustrated herein, the signal quality parameter may be measured from an isolated $I_{AC}$ component of the PPG signal. For example, melatonin or other skin tone differences may affect the $I_{DC}$ component of the PPG signal, but the $I_{AC}$ component reflects the pulsating volume of arterial or venous blood. The signal quality parameter of the isolated $I_{AC}$ component of the PPG signal may thus be used to determine a blood type as well.

The one or more measured signal quality parameters are compared to predetermined signal quality parameters for the one or more blood groups. For example, the calibration database 1300 may be accessed that associates values of predetermined signal quality parameters to a plurality of blood groups (e.g., types of antigens on surfaces of red blood cells). Based on the comparison, a blood group is obtained for the user. The blood group may be determined based on a single comparison or multiple comparisons.

Upon completion of the blood typing process, the state of the automatic gain controller may be changed or enabled. For example, the automatic gain controller or other varied gain may be applied to the PPG signal for determination of other patient vitals.

Embodiment—Non-Contact PPG Sensor

Non-contact methods for measuring vital signs are desirable both in hospital settings (e.g. in NICU) and for ubiquitous in-situ health tracking (e.g. on mobile phone with cameras and on computers with webcams or in vehicles with video of drivers). Such a non-contact PPG system is described in the article by Kumar M, Veeraraghavan A, Sabharwal A. entitled, "DistancePPG: Robust non-contact vital signs monitoring using a camera." Biomedical Optics Express. 2015; 6(5):1565-1588. doi:10.1364/BOE.6.001565, incorporated by reference herein.

As the heart pumps blood, the volume of blood in the arteries and capillaries changes by a small amount in response to the cardiac cycle. The change in blood volume in the arteries and capillaries underneath the skin leads to small change in the skin color and in the intensity of UV and IR light emitted by the skin. In a non-contact PPG system, the PPG waveform is proportional to these small changes in skin color and light emitted at UV and IR ranges.

In one embodiment, a plurality of frames or a video of a body part is recorded by a camera, and the PPG signal is estimated from the recorded frames. The recorded video or frames include intensity data of the emitted light $V(x, y, t)$ in each of the plurality of frames $V(x, y, t=1, 2, 3 \ldots)$. Each frame records the intensity level of the light reflected from the body part over a two dimensional array of pixels $(x, y)$ in the camera sensor or photodetector. If the camera sensor has multiple color channels (e.g. red, green, blue), one can get separate intensity signals corresponding to each channel (e.g. $Vr(x, y, t)$, $Vg(x, y, t)$, $Vb(x, y, t)$). In general, the measured intensity of the reflected light can be decomposed into two components: (i) intensity of illumination, and (ii) reflectance of the surface (skin), i.e. $V(x, y, t)=I(x, y, t)R(x, y, t)$.

The illumination intensity corresponds to the intensity of ambient or any dedicated light falling on the body part. For PPG estimation, it is generally assumed that the light intensity remains same over the PPG estimation window (typically 5-60 sec in past works). The skin reflectance $R(x, y, t)$ is equal to the fraction of light reflected back from the skin and consists of two level of light reflectance: (i) surface reflection, and (ii) subsurface reflection or backscattering.

A large part of the light incident on the body part gets reflected back from the surface of the skin, and is characterized by the skin's bidirectional reflectance distribution function (BRDF). Remaining part of the incident light goes underneath the skin surface and is absorbed by the tissue and the blood (Hb, HbO2) present in the blood vessels, veins, arteries and capillaries. The volume of blood in the arteries and capillaries changes with each cardiac cycle and thus the level of absorption of light changes as well. Since the PPG signal, by definition, is proportional to this cardio-synchronous pulsatile blood volume change the PPG signal p(t) may be estimated from these small changes in subsurface light absorption. Thus, the camera-based PPG signal is estimated by extracting small variations in the subsurface component of skin reflectance $R(x, y, t)$.

Since the incident light intensity $I(x, y)$ is assumed to be constant over PPG estimation time window, any temporal change in the intensity of the light reflected back from the face region will be proportional to the changes in the reflectance of the skin surface $R(x, y, t)$. Generally, these temporal changes in recorded intensity are due to changes in surface reflection component unrelated to the underlying blood volume changes. Thus, for non-contact PPG estimation, the recorded intensity level $V(x, y, t)$ over all the pixels in the body part are averaged to yield a measurement point per frame. By averaging the intensity signal, the incoherent changes in surface reflection component over all the pixels are cancelled out, and the coherent changes in subsurface reflection component due to blood volume changes add up to give an estimate $y(t)$. The spatially averaged intensity signal $y(t)$ is proportional to the changes in the subsurface reflectance component, and thus to the underlying PPG signal. The $y(t)$ signal is sampled between 0.5 Hz to 5 Hz (frequency band of interest) to extract the PPG signal.

For instance, observations of measured intensity in conventional contact PPG sensors indicate that the AC component accounts for only a small proportion of the total intensity (approximately 1% of the DC level). Therefore, the camera has a high sensitivity over the chosen light source spectral range and the flexibility to select variable readout speeds and exposure time for different applications. Thus, the change in subsurface skin reflectance due to cardio-synchronous changes in blood volume is very small. The small change in subsurface reflectance results in very small change in light intensity recorded using a camera placed at a distance.

Strength of the PPG signal extracted from a patch of the imaged skin surface depends on the intensity of light $I(x, y)$ incident on that patch and on the total amount of blood volume change underneath the skin patch. The total amount of blood volume change will depend on the blood perfusion in the region, which in turn will be determined by the density of blood carrying arteries and capillaries in that region. When pixel intensity is averaged over a body part to obtain $y(t)$, some skin patches may have limited blood perfusion, and hence contribute more noise than signal to the overall estimate of the camera-based PPG signal. Thus, some areas of skin may produce a PPG signal with less noise. For example, a video of a palm or forehead may provide a PPG signal with less noise than an arm or stomach. Thus, preferably, the camera is aimed at the face or hand of a user or a wrist of a user.

To estimate the pulse rate, the frequency spectrum of the PPG signal is obtained using a FFT algorithm over a predetermined period (hamming window). The pulse rate is estimated as the frequency that corresponds to the highest power in the estimated frequency spectrum. The frequency spectrum may be averaged or added over 5-10 second windows.

Figure 17:
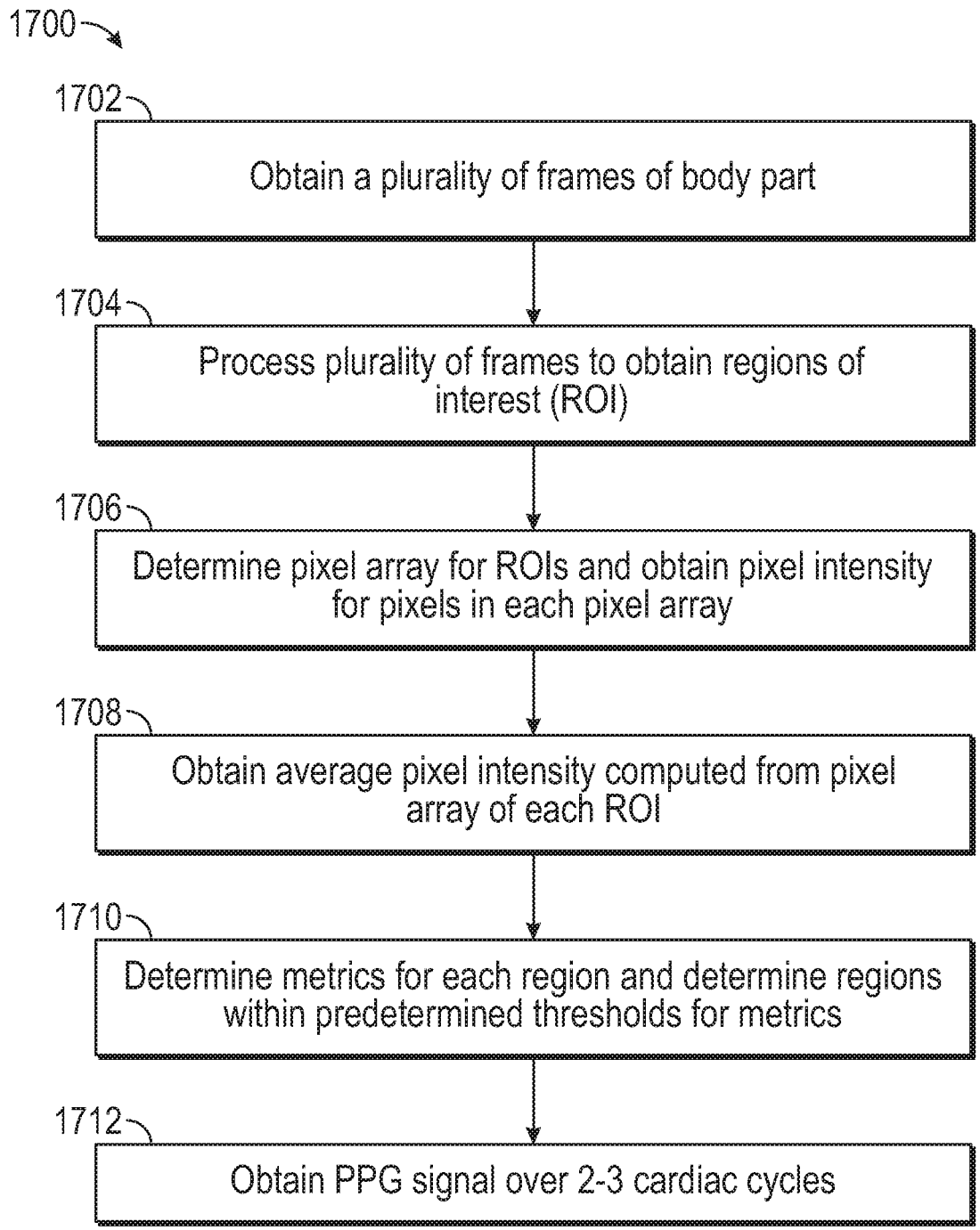
FIG. 17 illustrates a logical flow diagram of an embodiment of a method for obtaining PPG signals using a non-contact camera.

FIG. 17 illustrates a logical flow diagram of an embodiment of a method for obtaining PPG signals using a non-contact camera. A camera captures a plurality of frames or images of a body part at 1702. The images may be a video or frames obtained at a high frame rate. The camera may illuminate the body part using a flash or only ambient light. In an embodiment, the camera may include custom LEDs that emit light at one or more predetermined wavelengths. For example, LEDs may be implements to emit light at one or more of 390 nm, 468 nm, 592 nm, 660 nm, 940 nm or in a range of +/−20 nm from these wavelengths. For example, an LED that emits light at 380 nm-420 nm may be implemented in the camera.

An image sensor such as a photodetector captures the light reflected from the body part. In an embodiment, the photodetector is sensitive to UV, visible and IR light. For example, the image sensor may detect and record the intensity of reflected light in a broad spectrum including UV, visible and IR light. Some commercial cameras include an IR filter or do not record or store data in the UV and IR range. In such cases, violet light in the 400 nm range may be used instead of 390 nm and a red light at 660 nm may be used rather than IR light.

Preferably, the camera captures the plurality of frames over 2-3 cardiac cycles at a frame rate of 24 Hz or higher. When a user is moving, the plurality of frames may be chosen at different time periods to obtain frames with minimal motion artifacts. For example, a plurality of frames over a first time period (e.g., one second) may be selected and a second plurality of frames over a second time period (e.g., 3-4 seconds) may be selected, etc.

The plurality of frames are processed to identify a plurality of regions of interest (ROI) at 1704. For example, when the body part includes the face, the forehead, left cheek, right cheek, chin may be identified as regions of interest. When the video includes an underside of a hand, the regions of interest may include, e.g., a palm area, a first fingertip, a second fingertip, a wrist, etc.

A pixel array is determined for each of the regions of interest, and the pixel intensity for pixels in each pixel array are obtained at 1706. The size of the pixel array may vary depending on the ROI. The average or mean pixel intensity for each ROI is obtained at 1708 on a frame by frame basis. Metrics are determined for each ROI and compared to predetermined thresholds at 1710. For example, when the average or mean pixel intensity level of a ROI fails to meet a predetermined threshhold, or the S/N ratio threshold or other metric is not within a threshold, the ROI may be ignored. A higher weight may be given to ROIs with higher S/N ratios. The average pixel intensity or the spatial mean average or other mode of any distribution, is derived for the ROIs for each frame. A time series of these intensities is assembled for a series of frames in a time window of, for example, 2-10 seconds.

The PPG signal is then obtained, e.g. using the time series of intensities and autoregression techniques, over the 2-3 cardiac cycle at 1712. Individual wavelengths may be isolated using FFT techniques or using time-frequency analysis to obtain spectral responses over 2-3 cardiac cycles for the individual wavelengths. In an embodiment, a camera may have different RGB channels and each channel is processed separately. The camera may alternatively be equipped with a photodetector that is sensitive to a range of spectrums such as as UV, IR and visible light. Alternatively, the camera may sequentially illuminate the body part with light at different wavelengths. Different videos may then be acquired, each at a different one of the wavelengths.

Figure 18:
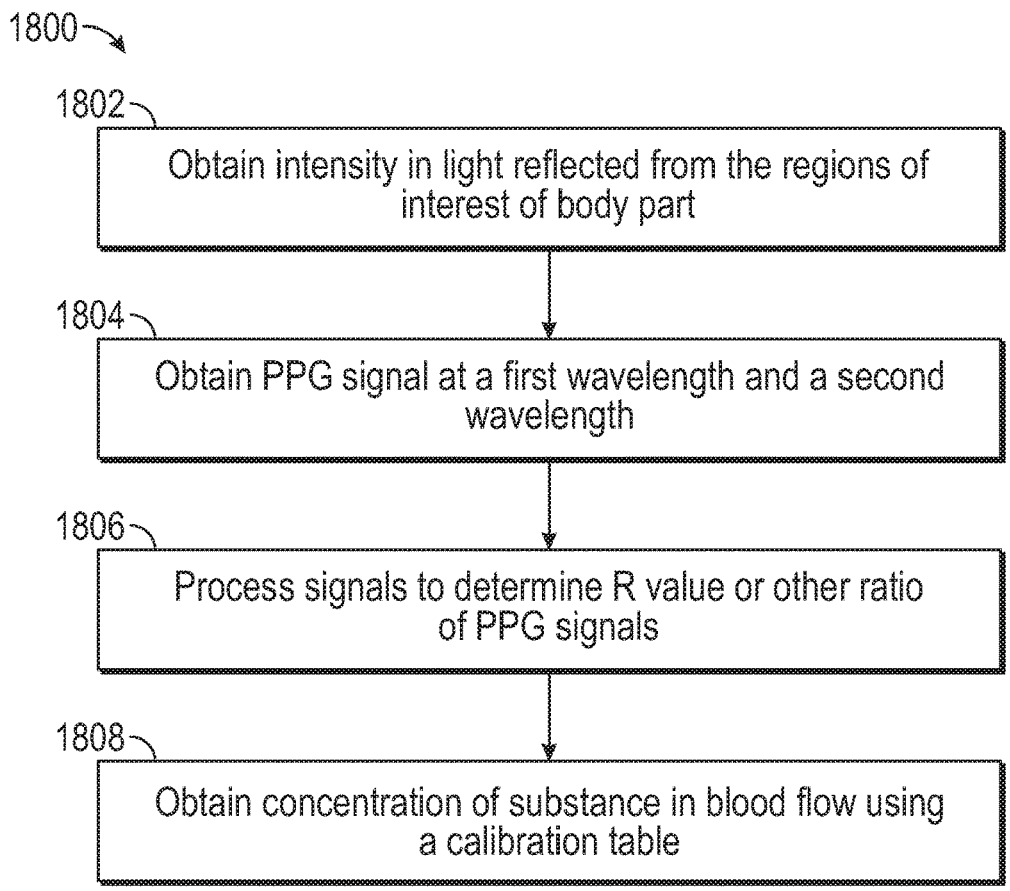
FIG. 18 illustrates a logical flow diagram of an embodiment of a method for detection of a substance in blood flow using a non-contact PPG camera.

In prior non-contact PPG imaging studies, $SpO_2$ is measured using visible light or IR light. For example, in the article by Wieringa F. P., Mastik F., van der Steen A. F. W., "Contactless multiple wavelength photoplethysmographic imaging: a first step toward SpO2 camera technology," Ann Biomed. Eng. 33, 1034-1041 (2005), which is incorporated by reference herein, a camera was built with a monochrome CMOS-camera with apochromatic lens and a three wavelength LED ringlight (lambda1=660 nm, lambda2=810 nm, lambda3=940 nm). Three different videos were acquired, each at a different one of the three wavelengths in the visible and IR range. The high definition camera coupled with a customized light source was employed in this study for the non-contact imaging to determine $SpO_2$ FIG. 18 illustrates a logical flow diagram of an embodiment of a method 1800 for detection of a substance in blood flow using a non-contact PPG camera. A plurality of frames is obtained, and the intensity of light reflected from a plurality of ROIs of a body is determined for a set of frames at 1802. A time series of the intensity of light is determined. The PPG signal is derived from the time series of the intensity of light at a first wavelength and a second wavelength at 1804. The signals are processed to determine an R value or ratio of intensities at the different wavelengths at 1806. For example, the ratio between the peak-to-peak pulse wave amplitudes in the PPG signals at the two different wavelengths is acquired. A concentration of a substance in blood flow is obtained using the ratio and a calibration database at 1808.

In one embodiment, a commercial camera is employed, and a PPG signal derived from a blue channel (preferably around 400 nm) and a PPG signal derived from a Red channel. An R value or other ratio may then be determined from the two PPG signals. The R value or other ratio is then used to obtain a concentration level of nitric oxide (NO) using a calibration table. Some commercial cameras include a controllable IR filter to illuminate dark images. The IR filter may be removed to obtain a PPG signal in the IR range. An R value or other ratio may then be determined from a PPG signal in the blue range (preferably around 400 nm) and a PPG signal in an IR range. A concentration level of nitric oxide NO in blood flow may then be determined using the R value (or other ratio of the PPG signals) and a calibration table.

In a custom camera, an LED in a range of 390 nm (+/−20 nm) and in a range of 940 nm (+/−20 nm) may be implemented along with a photodetector that is sensitive to UV, visible and IR light. An R value or other ratio may be determined using the spectral data at 390 nm and 940 nm. A concentration level of nitric oxide NO in blood flow may then be determined using the R value (or other ratio of the PPG signals) and a calibration table.

In an embodiment herein, detection of light in UV range may be implemented in the camera, e.g. from ambient light or a custom LED. Derivation of a PPG signal from light reflected in the UV range from a body part has been found to have advantages over light in the visible and IR range. For example, UV light reflected from a face may be used to derive a PPG signal. The UV light provides an improved PPG signal for detection of heart rate, respiration rate, $SpO_2$ and NO levels.

Figure 19:
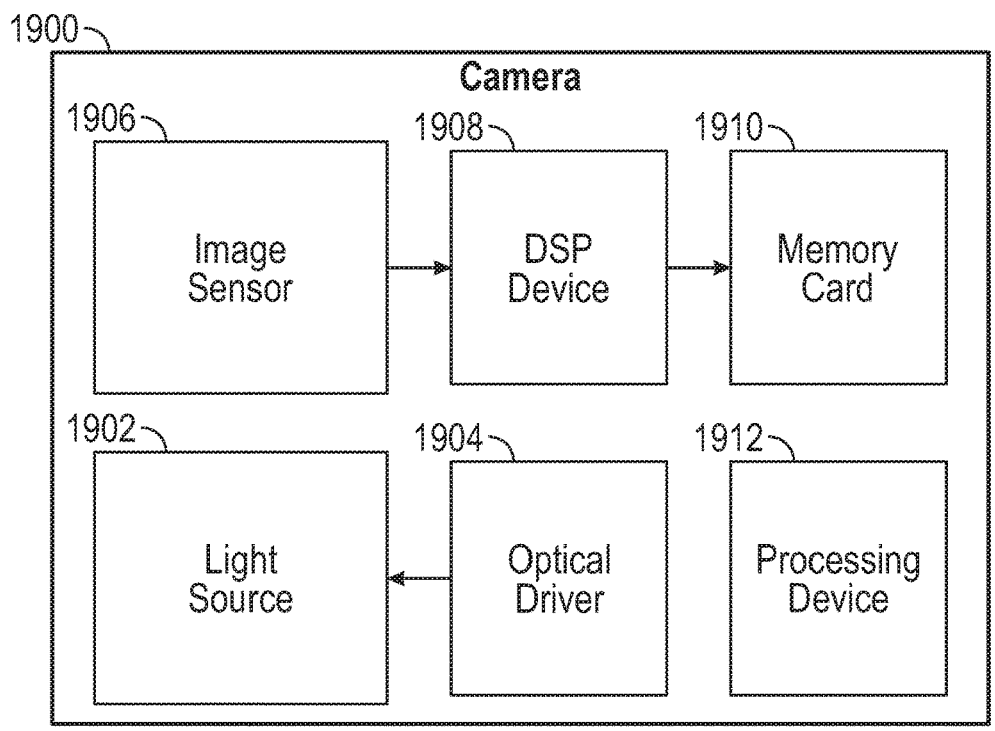
FIG. 19 illustrates a schematic block diagram of an embodiment of a camera for non-contact PPG imaging.

FIG. 19 illustrates a schematic block diagram of an embodiment of a camera 1900 for non-contact PPG imaging. In an embodiment, the camera includes a light source configured to emit light in one or more of the visible, IR and/or UV spectrum. In one embodiment, an optical driver 1904 is configured to control the light source 1902. In a health monitoring mode, the optical driver 1904 controls the light source to emit light at predetermined wavelengths to detect health data. The health data may include one or more of: heart rate, respiration rate, heart rate variability, blood pressure, etc. The health data may also include concentration levels of substances in blood flow such as $SpO_2$, nitric oxide (NO), liver enzymes such as P450, or other blood substances. For example, for detection of SpO2, the optical driver 1904 controls the light source 1902 to emit light in an IR range (such as 940 nm) and in a visible range (such as 660 nm). For detection of an NO concentration level, the optical driver 1904 controls the light source 1902 to emit light in the UV range (such as around 390 nm) and in the IR range (such as 940 nm). In another embodiment, the light source 1902 emits these wavelengths of light in the UV and IR range but a controllable filter prevents detection by the image sensor 1906 or signal processing device 1908.

The camera 1900 further includes an image sensor 1906 (such as a photodetector) that is sensitive to UV, visible and IR light. A digital signal processing (DSP) device 1908 receives the pixel intensity levels for an array of pixels (such as 1024×1068) at each channel (RGB, IR, UV, etc.) for each frame. The UV and IR light may be filtered when not in a health monitoring mode. In a health monitoring mode, the image sensor 1906 and DSP device 1908 process IR and UV channels as well as RGB channels. A memory card 1910 stores the image data for each frame. A processing device 1912 is configured to process the image data for the frames to determine PPG signals at one or more wavelengths and obtain health data. In another embodiment, the image data may be transmitted to another control module for determination of the health data. The camera 1900 may be implemented in a user device, such as a smart phone, laptop, smart tablet, watch, bracelet, button, webcam, video camera in a vehicle, etc.

For example, the camera 1900 may be implemented in a smart phone. A user may take a 4-5 second video of their face or hand. The user device may then generate PPG signals at one or more wavelengths and obtain health data of the user. In another example, the camera 1900 may be embedded in a vehicle to monitor health data of a driver. The health data of the driver may be displayed on a user device or on a vehicle display. In another example, the camera may be installed to monitor a patient in a hospital bed or an infant in a NICU. The camera feed may be transmitted to a user device or monitoring station that displays the video feed and health data of the patient.

Embodiment—Neural Network

One or more types of artificial neural networks (a.k.a. machine learning algorithms) may be implemented herein to determine health data from PPG signals. For example, neural networks may be used to obtain a concentration level of NO or glucose or other health data from input data derived from PPG signals. Neural network models can be viewed as simple mathematical models defining a function $f$ wherein $f:X \rightarrow Y$ or a distribution over X or both X and Y. Types of neural network engines or APIs currently available include, e.g. TensorFlow™, Keras™, Microsoft® CNTK™, Caffe™, Theano™ and Lasagne™.

Sometimes the various machine learning techniques are intimately associated with a particular learning rule. The function $f$ may be a definition of a class of functions (where members of the class are obtained by varying parameters, connection weights, thresholds, etc). The neural network learns by adjusting its parameters, weights and thresholds iteratively to yield desired output. The training is performed using defined set of rules also known as the learning algorithm. Machine learning techniques include ridge linear regression, a multilayer perceptron neural network, support vector machines and random forests. For example, a gradient descent training algorithm is used in case of supervised training model. In case, the actual output is different from target output, the difference or error is determined. The gradient descent algorithm changes the weights of the network in such a manner to minimize this error. Other learning algorithms include back propagation, least mean square (LMS) algorithm, etc. A set of examples or a training set is used for learning by the neural network. The training set is used to identify the parameters [e.g., weights] of the network.

Figure 20:
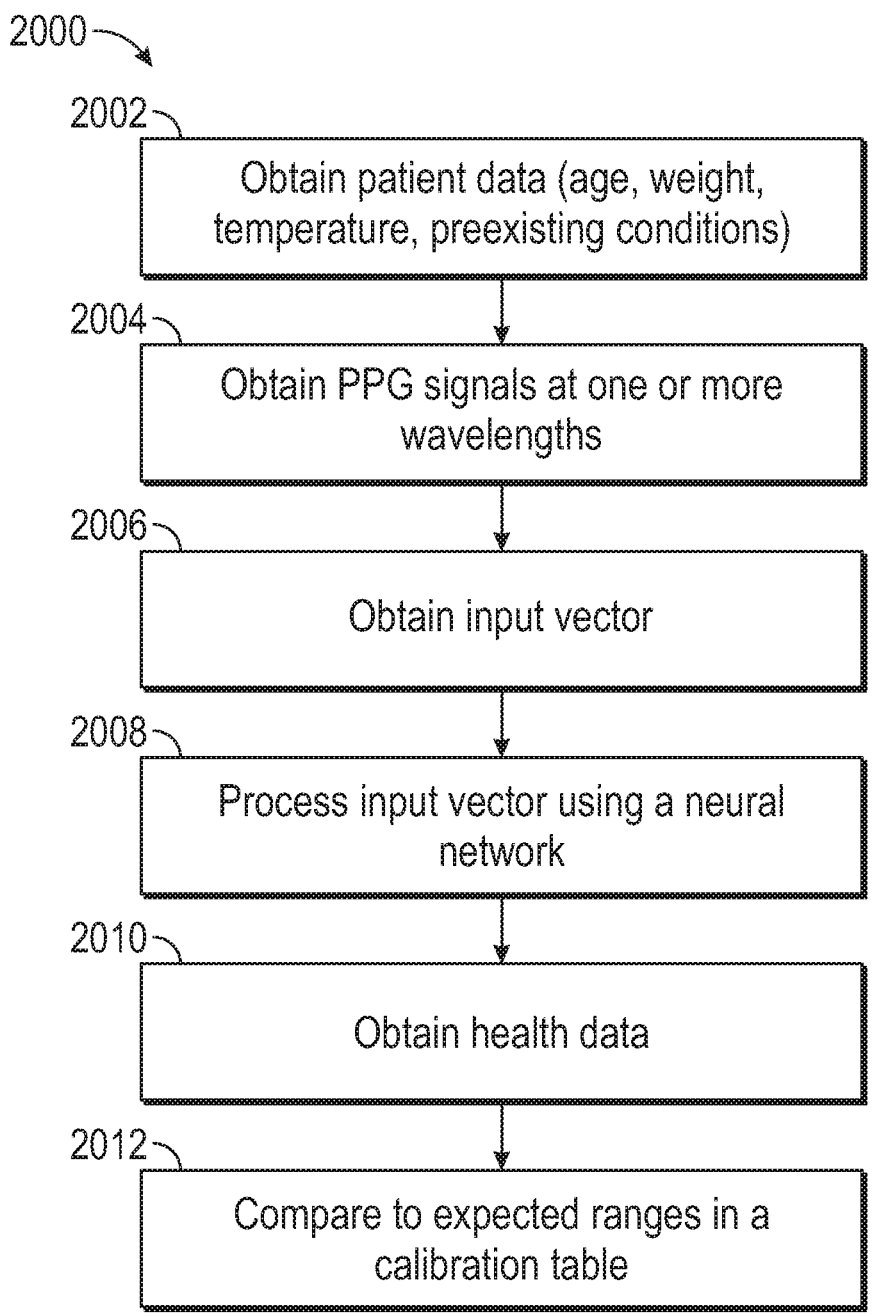
FIG. 20 illustrates a logical flow diagram of an embodiment of a method for using a machine learning technique for detection of health data.

FIG. 20 illustrates a logical flow diagram of an embodiment of a method for using a machine learning technique for detection of health data. In an embodiment, patient data is obtained at 2002. The patient data may include one or more of: age, weight, body mass index, temperature, blood pressure, pre-existing medical conditions, trauma events, mental conditions, injuries, demographic data, physical examinations, laboratory tests, diagnosis, treatment procedures, prescriptions, radiology examinations, historic pathology, medical history, surgeries, etc. PPG signals at one or more wavelengths are obtained at 2004.

Various parameters of the PPG signals may be determined or measured. These parameters include the diastolic and systolic points, the L values, R values, pulse shape (measured by autoregression coefficients and moving averages), characteristic features of the shape of the PPG waveform, the average distance between pulses, variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, and determining the zero crossings of the PPG signal. These and other parameters may be obtained using a PPG signal. The PPG input data may include the PPG signals and/or one or more parameters derived from the PPG signals.

An input vector is obtained at 2006. The input vector includes the PPG input data, such as the PPG signals at one or more wavelengths and/or one or more parameters generated from the PPG signals at the one or more wavelengths. Since the PPG signal is of variable duration, a fixed dimension vector for a measurement of the PPG signal may be obtained. The input vector may also include patient data.

The input vector is processed by a processing device executing a neural network (aka machine learning algorithm). The processing device executes the machine learning algorithm with the input vector and determines health data at 2010. The health data includes one or more of heart rate, respiration rate, blood pressure, oxygen saturation level, NO level, liver enzyme level, Glucose level, Blood alcohol level, blood type, sepsis risk factor, infection risk factor, cancer, virus detection, creatinine level or electrolyte level. The health data may be generated as an output fixed length vector.

The obtained health data may be compared to expected ranges or thresholds in a calibration table at 2012.

Figure 21:
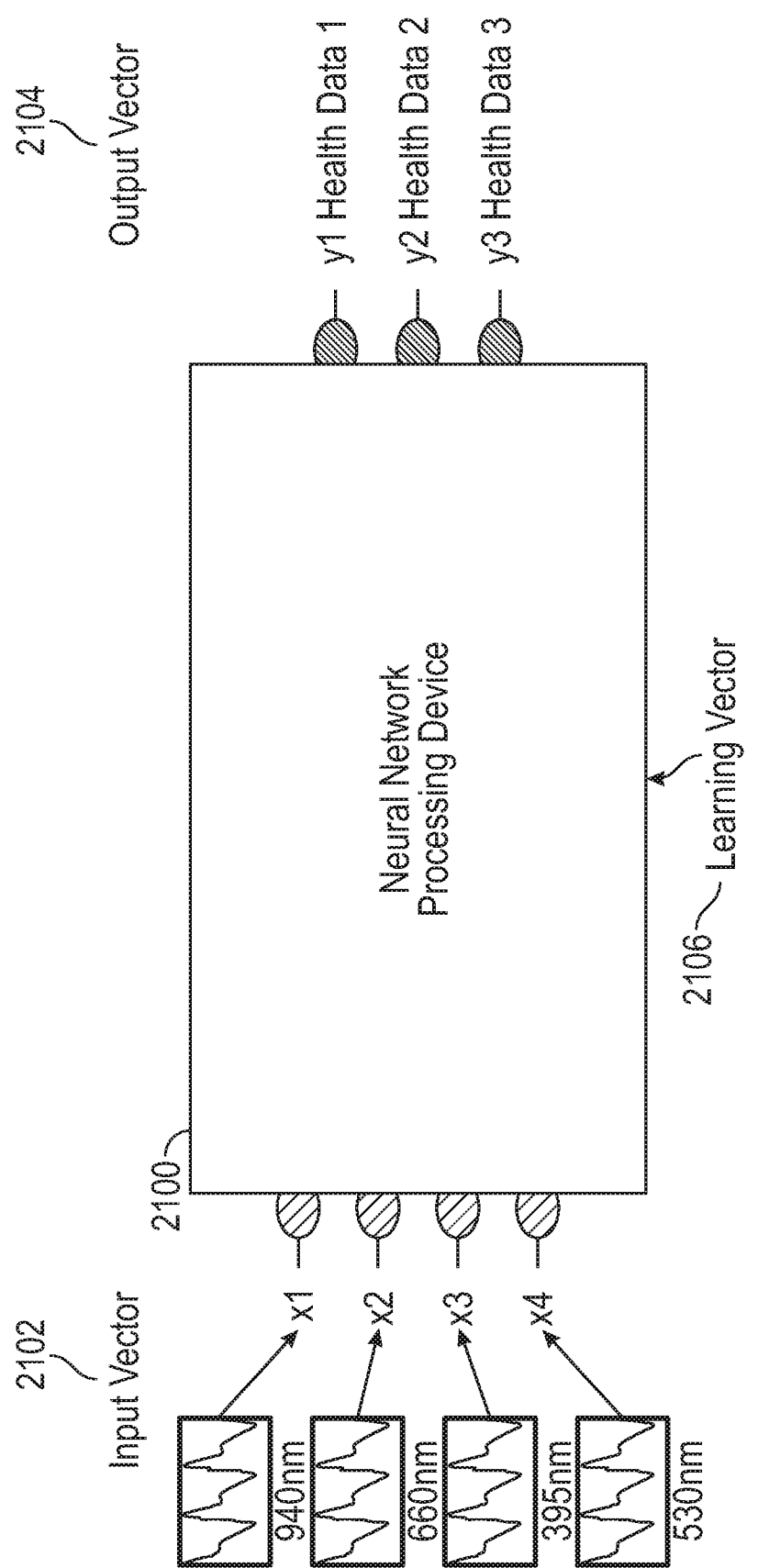
FIG. 21 illustrates a schematic block diagram of an embodiment of a neural network processing device.

FIG. 21 illustrates a schematic block diagram of an embodiment of a neural network processing device 2100. The neural network processing device 2100 obtains or generates an input vector 2102. In this embodiment, the input vector includes an AC component $I_{AC}$ of one or more PPG signals at different wavelengths. For example, a PPG signal may be processed to isolate or filter an AC component $I_{AC}$ from a DC component. The PPG signal is obtained from light in a UV range, e.g. at approximately 395 nm (+/−20 nm). The input vector may include an identification of the wavelength, an intensity level, a time measured, etc. over a measurement period, such as 2-3 cardiac cycles. The input vector may include an AC component $I_{AC}$ of one or more PPG signals at other wavelengths, such as in the IR range of 940 nm (+/−20 nm). The output vector 2104 may then include health data, such as one or more of: heart rate, respiration rate, NO concentration level, sepsis risk, diabetic risk, glucose level, etc.

The neural network processing device 2100 may be pre-configured with weights, parameters or other learning vectors 2106 derived from a training set. The training set preferably included sets with the same type of information in the input vector and known values of the health data in the output vector 2104. For example, glucose levels for a healthy population may be obtained along with the AC component $I_{AC}$ of PPG signals at 390 nm and 940 nm. This training set is provided to a neural network training algorithm to generate the learning vectors 2106. The training set may include further patient data such as age, weight, bmi, pre-existing conditions (diabetes), medical history (family members with diabetes), etc. The input vector 2102 may then include such patient data to provide more accurate values for the output vector 2104.

The input vector 2102 may include an AC component $I_{AC}$ of one or more other PPG signals at other wavelengths, such as at 880 nm, 660 nm, 468 nm, 440 m, 550 nm, 530 nm, 592 nm or in a range of +/−20 nm from these wavelengths. The output vector 2104 may then include health data, such as one or more of: liver enzyme level, blood alcohol level, ethanol, digestive indicator to measure digestive responses, concussion, PTSD, cholesterol levels, creatinine level, electrolytes, etc.

Though the input vector 2102 is described as including an AC component $I_{AC}$ of one or more PPG signals at one or more different wavelengths, the input vector 2102 may additionally or alternatively include other PPG input data. For example, the input vector 2102 may include a DC component $I_{DC}$ from PPG signals obtained at one or more wavelengths of 390 nm, 660 nm, 468 nm, 530 nm, 592 nm, 880 nm, 940 nm, 1050, or in a range of +/−20 nm from these wavelengths.

For example, the input vector 2102 may include L values derived from PPG signals obtained at one or more wavelengths of 390 nm, 660 nm, 468 nm, 530 nm, 592 nm, 880 nm, 940 nm, 1050 or in a range of +/−20 nm from these wavelengths. The L values may be derived at predetermined intervals over a measurement window. The input vector 2102 may include R values derived from PPG signals obtained at two or more wavelengths of 390 nm, 660 nm, 468 nm, 530 nm, 592 nm, 940 nm, 1050 or in a range of +/−20 nm from these wavelengths. For example, one or more of the following R values measured over a time period may be included in an input vector: $R_{390/940}$, $R_{660/940}$, $R_{468/940}$, $R_{1050/940}$ etc.

In another example, the input vector 2102 may include systolic values and/or diastolic values (peak detect points) derived from PPG signals obtained at one or more wavelengths of 390 nm, 660 nm, 468 nm, 530 nm, 592 nm, 880 nm, 940 nm or in a range of +/−20 nm from these wavelengths.

Figure 22:
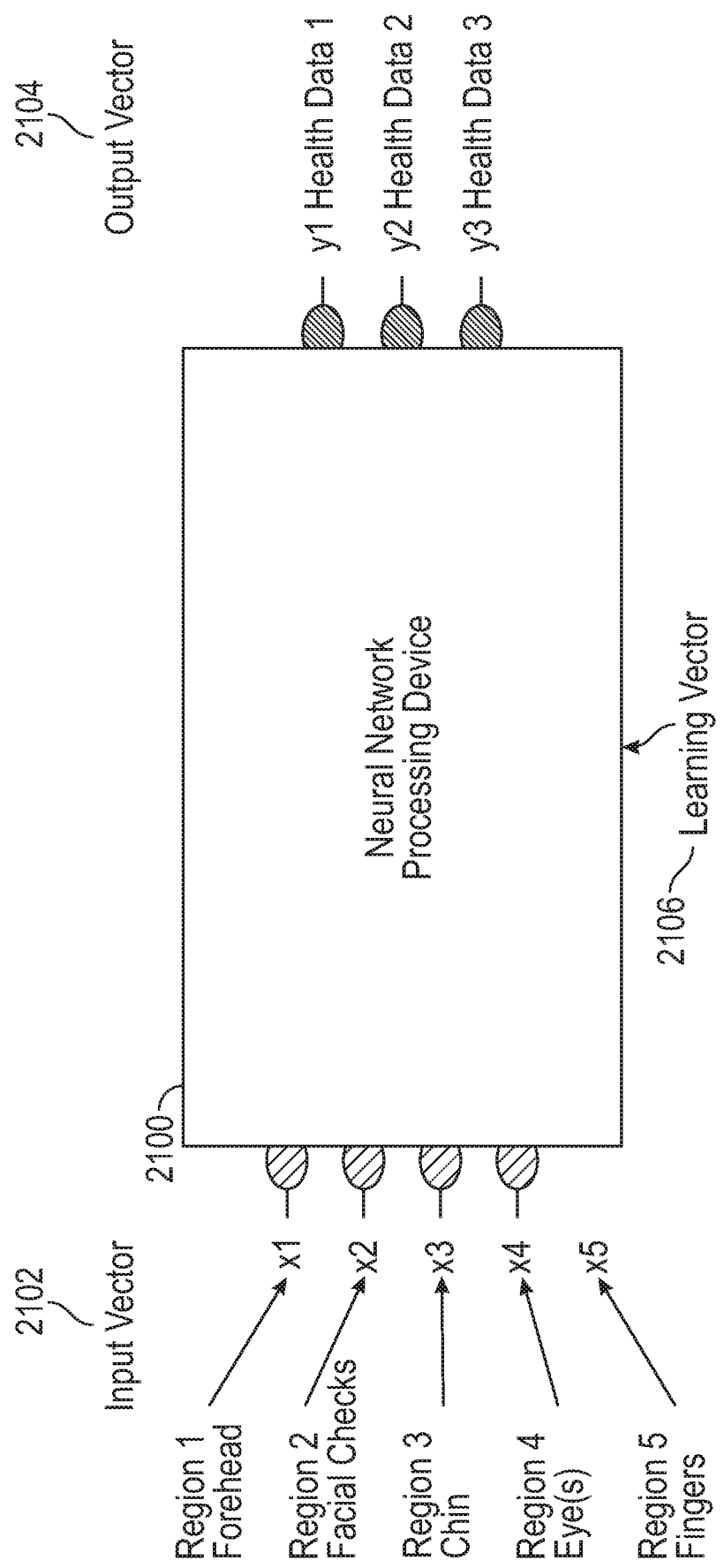
FIG. 22 illustrates a schematic block diagram of another embodiment of the neural network processing device.

FIG. 22 illustrates a schematic block diagram of another embodiment of the neural network processing device 2100. The neural network processing device 2100 obtains or generates an input vector 2102 derived from non-contact PPG signals. In this embodiment, the input vector includes image data from a non-contact camera. The image data may include PPG signals derived from different regions of interest (ROI), such as forehead, facial cheek, chin, eye region, fingers, wrist, palm, etc. The input vector may include the pixel intensity of a plurality of frames obtained from light reflected from the ROI. The neural network processing device 2100 may be trained to identify the ROI in each frame and the pixel array corresponding to the ROI in each frame. The neural network processing device 2100 may also determine ROI metrics and thresholds to eliminate frames or ROIs from consideration. The image data may be obtained at a single wavelength or at multiple wavelengths, such as one or more wavelengths of 390 nm, 440 nm, 468 nm, 530 nm, 550 nm, 592 nm, 660 nm, 880 nm, 940 nm or in a range of +/−20 nm from these wavelengths. The neural network processing device 2100 may then obtain an output vector 2104 including health data from the input vector 2102.

Figure 23:
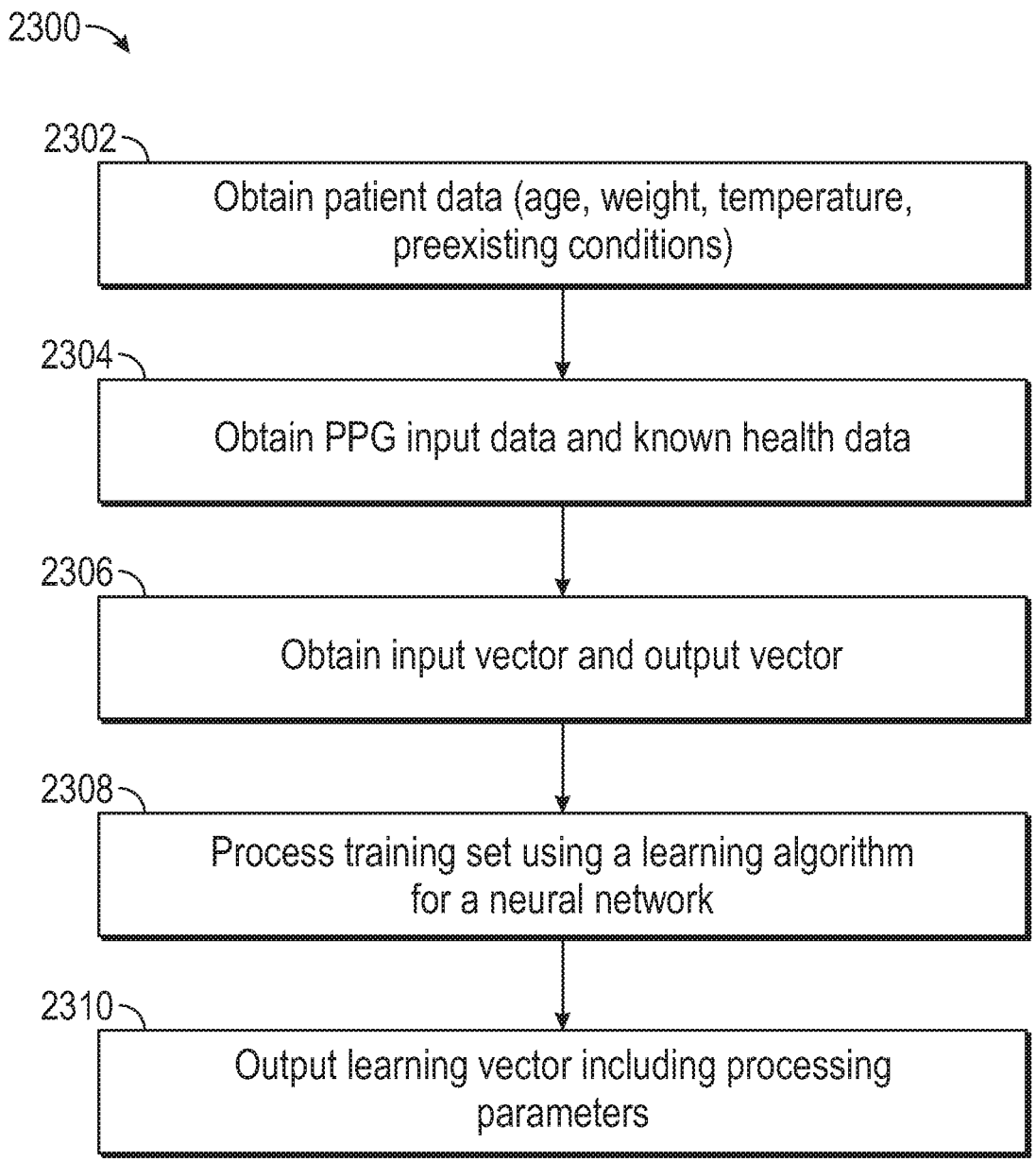
FIG. 23 illustrates a logical flow diagram of an embodiment of a method of generating a learning vector from a training set.

FIG. 23 illustrates a logical flow diagram of an embodiment of a method 2300 of generating a learning vector 2106 from a training set. During a learning stage, a neural network adjusts parameters, weights and thresholds iteratively to yield a known output vector from an input vector. The training is performed using defined set of rules also known as the learning algorithm. For example, a gradient descent training algorithm is used in case of supervised training model. In case, the actual output is different from target output, the difference or error is determined. The gradient descent algorithm changes the weights of the network in such a manner to minimize this error. Other learning algorithms include back propagation, least mean square (LMS) algorithm, etc. A set of examples or a training set is used for learning by the neural network. The training set is used to identify the parameters [e.g., weights] of the neural network.

The input vectors and known output vectors are included in a training set. In an embodiment, the training set is obtained in a clinical setting. For example, patient data is obtained at 2302, such as age, weight, temperature, blood pressure, pre-existing conditions, and medical history. PPG input data and health data is then obtained at 2304. Preferably, the health data is obtained using an independent method. For example, an NO level and/or a glucose level of the patient are obtained using a known method such as fingerprick and a blood test. Then PPG signals at one or more wavelengths are obtained, such as at 390 nm and 940 nm or in a range of +/−20 nm from these wavelengths. PPG input data is determined from the PPG signals, as described hereinabove. The input vector is then derived from the PPG input data and patient data. The training set preferably includes a plurality of input vectors and corresponding output vectors.

The training set is processed at 2306 using a learning algorithm for a neural network. The neural network determines a learning vector 2106, e.g. processing parameters at 2308. The estimator function system 140 may work blindly, in the sense that no functional restriction is imposed on the relationship between pulse shapes and glucose levels. In an embodiment, the machine learning algorithm may include one or more of: a "random forest", deep belief network trained using restricted Boltzmann machines, or support vector machine. The analysis may use any known regression analysis technique, such as, for example and without limitation, random forests, support vector machines, or a deep belief network trained using restricted Boltzmann machines.

The learning vector 2106 including processing parameters are provided to the biosensor 100 or neural network processing device 2100 at 2308. The neural network processing device is configured with processing parameters in the learning vector 2106 to process input vectors to obtain output vectors.

In an embodiment, the input vector 2102 is derived from one or more PPG signals at one or more wavelengths, such as of 390 nm, 660 nm, 440 nm, 468 nm, 530 nm, 550 nm, 592 nm, 880 nm, 940 nm or in a range of +/−20 nm from these wavelengths. The PPG signals are measured over a time period including at least 2-3 cardiac cycles. As described herein, the PPG signal at 390 nm or in a range of +/−20 nm may be used to determine an NO level, glucose level, as well as a respiration rate and a heart rate. The light in the UV range, such as 390 nm or in a range of +/−20 nm, reflected from certain body parts provides an improved PPG signal. For example, UV light reflected from a face provides an improved PPG signal, especially in non-contact PPG imaging systems.

In an embodiment, the training set is continually updated, e.g. from clinical settings and user input. The learning vector 2106 may be periodically updated (such as hourly, daily, etc.). The updated learning vector 2106 may then be obtained and configured on the neural network processing device 2100 periodically as well (such as hourly, daily, etc.). In addition, a user may update a learning vector 2106 based on personal measurements of health data and PPG signals. For example, a user may measure glucose level using a finger prick type blood test and input the glucose level and activate the camera or biosensor to obtain PPG signals. These measurements may be taken over a few days or weeks to calibrate a neural network processing device 2100 to generate a user's training set. This training set may be used to update the learning vector 2106 for the user's neural network processing device 2100.

Figure 24:
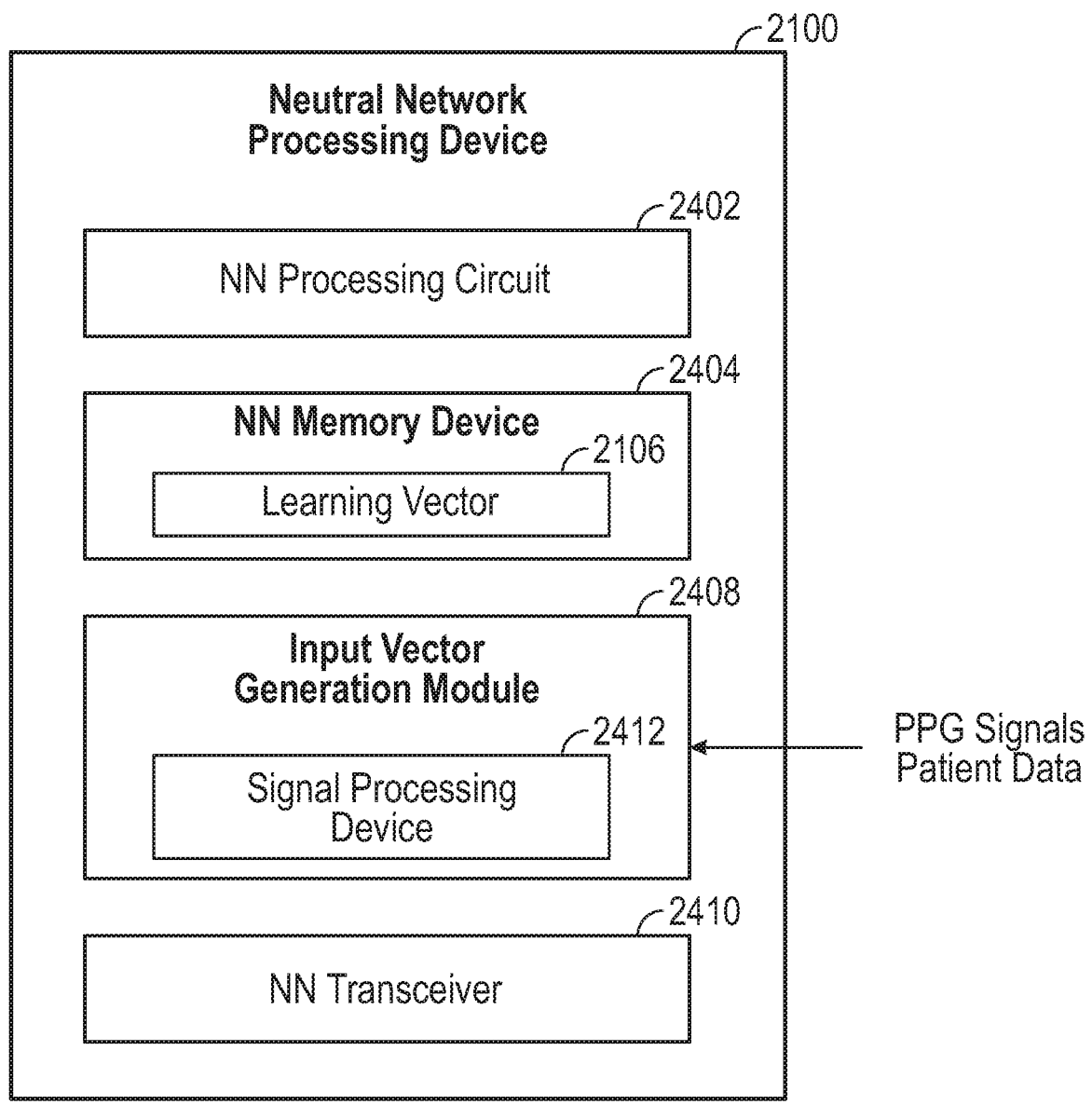
FIG. 24 illustrates a schematic block diagram of an embodiment of a neural network processing device in more detail.

FIG. 24 illustrates a schematic block diagram of an embodiment of a neural network processing device 2100 in more detail. The neural network (NN) processing device 2100 includes a NN processing circuit 2402 and NN memory device 2404. The NN memory device 2404 stores a learning vector 2106 and updates thereto. An input vector generation module 2408 is configured to generate the input vector 2102 from PPG signals and health data. The PPG signals may be obtained by a PPG circuit 110 or a non-contact camera 1900. A signal processing circuit 2412 may be incorporated into the NN processing device 2100 to process the PPG signals to generate the PPG input data.

The input vector generation module 2408 generates an input vector 2102 including the PPG input data and/or the patient data. The NN processing circuit 2402 is configured to implement a machine learning algorithm configured with the learning vector 2106. The NN processing circuit may also compare the output vector 2104 to thresholds in the output vector to calibrate or verify the results. The NN transceiver 2410 may transmit the output vector 2104 and input vector 2102 to another device, such as a biosensor 100, user device or central control server.

In an embodiment, a PPG signal at 390 nm (+/−20 nm) or parameters derived therefrom is included in the input vector 2102 to obtain an NO level or glucose level or diabetic risk factor. As such, other parameters may not need to be included in the input vector such as blood pressure readings to obtain a glucose level. The neural network processing device 2100 may also obtain an indicator of a risk of sepsis or infection from the PPG signal at 390 nm (+/−20 nm) or parameters derived therefrom.

In another embodiment, the neural network processing device 2100 may also obtain a concentration level of a liver enzyme (such as P450) and/or a blood alcohol level. For example, a PPG signal at 468 nm (+/−20 nm) or parameters derived therefrom is included in the input vector 2102. The PPG signal at 468 nm is sensitive to P450 levels, and thus blood alcohol level in blood flow. The NN processing device 2100 may thus be trained to obtain P450 concentration levels in blood flow and/or blood alcohol levels from an input vector including a PPG signal at 468 nm (+/−20 nm) or parameters derived therefrom. The NN processing device 2100 may also be configured to obtain a concentration level of an indicator in blood flow of alcohol levels using other alcohol dehydrogenase (ADH) related enzymes, such as NAD+ or NADH, which are released in response to alcohol in the blood stream. The NN processing device 2100 may thus determine the blood alcohol level using obtained spectral responses reflected from the skin of the patient around a first wavelength of approximately 468 nm and around a second wavelength of approximately 940 nm.

In another embodiment, the neural network processing device 2100 may also obtain a a level of vasodilation. For example, in an embodiment, a level of vasodilation is determined using an intensity of the PPG signals. In another embodiment, a first spectral response is in the UV range and a second spectral response in the IR range. The health data may further include a blood pressure, a heart rate, or a respiration rate.

In another embodiment, the neural network processing device 2100 may also perform authentication or identification of a user based on a PPG waveform. A training set of PPG signals from a known user at one or more ROIs (such as face, hand, fingerprint, earlobe, etc.) and/or at one or more wavelengths is collected. The training set may be updated over time since the PPG waveform of a user may vary over time (e.g. updated at least once per year). The NN processing device 2100 may perform pattern recognition to determine whether the measured PPG waveform is from an authorized user or provide an identity of the user.

In another embodiment, the neural network processing device 2100 may also obtain a concentration level of ethanol in blood flow. For example, a PPG signal at 1050 nm (+/−20 nm) or parameters derived therefrom is included in the input vector 2102. The PPG signal at 1050 nm is sensitive to ethanol levels, and thus blood alcohol level in blood flow. The NN processing device 2100 may thus be trained to obtain ethanol concentration levels in blood flow and/or blood alcohol levels from an input vector including a PPG signal at 1050 nm (+/−20 nm) and/or parameters derived therefrom. A second wavelength, such as at 940 nm (+/−20 nm), may be utilized with a low absorbance coefficient for ethanol.

In another aspect, the neural network processing device 2100 may also obtain creatinine levels in blood flow. For example, a PPG signal at 530 nm (+/−20 nm) or parameters derived therefrom is included in the input vector 2102. Creatinine is produced by the kidneys and various factors can affect the kidney production levels of creatinine. The biosensor 100 may detect spectral responses, e.g. at 530 nm and 940 nm or in ranges+/−20 nm and obtain an $R_{530/940}$ value. The biosensor 100 may then provide an indicator of a concentration level of creatinine in blood flow based on the $R_{530/940}$ value and a calibration database.

In another aspect, an indicator of glucose levels may be included in the input vector 2102. The glucose levels may be obtained over fasting and/or in response to caloric intake over a predetermined time period. The neural network processing device 2100 may then be trained to determine an indicator of various conditions, such as diabetes, diabetic risk, hypoglycemic risk, kidney function, etc.

In another embodiment, one or more steps of the blood type identification process may be performed by the neural network processing device 2100. For example, the PPG signals at various wavelengths may be included in the input vector 2102 and an output vector 2104 includes a blood type. For example, PPG signals at one or more of 530 nm, 590 nm or 940 nm or in a range of +/−20 nm from these wavelengths (or parameters derived therefrom) are included in the input vector 2102. The neural network processing device 2100 may then determine a blood type of the user (A, B, O, AB, RH+, RH−) based on the input vector 2102.

In another embodiment, a blood type identification process may be performed by the neural network processing device 2100 based on signal quality parameters of the PPG signals. For example, the average value of the auto or cross-correlation of the PPG signals at one or more wavelengths may be included in the input vector 2102 and an output vector 2104 includes a blood type.

In another embodiment, the neural network processing device 2100 may determine cholesterol levels. For example, PPG signals around a first wavelength with a high absorption coefficient for cholesterol, such as 440 nm or 550 nm, are included in the PPG input data. PPG signals around a second wavelength with a lower absorption coefficient for cholesterol are also obtained, such as 880 nm or 940 nm, and included in the input data. The PPG input data may include L values and/or an R value obtained using the first and second wavelengths, such as $R_{440/940}$ or $R_{550/940}$. In another embodiment, the cholesterol levels, such as LDL-Cholesterol, HDL-Cholesterol, and Triglycerides, may be determined from a shape of the PPG waveforms. One or more characteristic features of the shape of the PPG waveform are included in the PPG input data. In another embodiment, the input vector includes both an R value and characteristic features of the shape of the PPG waveform. The neural network processing device 2100 may then determine cholesterol levels from the input vector.

In another embodiment, the neural network processing device 2100 may determine concussions or mild traumatic brain injury (TBI) from an input vector. These conditions produce abnormal NO levels or patterns, especially when monitored over time after a potential head injury. The PPG signals around 390 nm+/−20 nm range or parameters thereof may be included in the input vector. The PPG signals are preferably obtained within second or minutes after the potential head injury and for at least 2-3 hours thereafter. In addition, information or data on any traumatic events or potential head injury may be included as patient data in the input vector. The input vector may be updated periodically after the potential head injury as PPG signals are obtained after the injury. For example, the input vector is updated with additional PPG signal data several times a minute, and processed by the neural network processing device 2100. This process may be performed, e.g., for sideline evaluation of potentially concussed athletes, or for evaluation in an emergency room. The neural network processing device 2100 may issue a warning of a concussion or mild traumatic brain injury (TBI).

In another embodiment, the neural network processing device 2100 may determine a potential PTSD diagnosis. PTSD produces abnormally high NO levels or patterns over an extended period. The PPG signals around 390 nm+/−20 nm range or parameters thereof may be included in the input vector. The PPG signals are preferably obtained over a period of weeks or months. In addition, information or data related to a history of any traumatic events experienced by the user (such as combat, victim of crime or abuse, accident victim, etc.) or other PTSD symptoms may be included as patient data in the input vector. The neural network processing device 2100 may determine a diagnosis of PTSD or a risk of PTSD from the input vector.

In each of these embodiments, the NN processing device 2100 is pre-configured with learning parameters, e.g. from a learning vector generated using a training set. The training set includes a similar data in an input vector and known results in an output vector.

In another embodiment, the NN processing device 2100 may authenticate a user or determine an identity of user. The PPG waveforms of a user are unique, e.g. the PPG waveforms of a subject are different from the PPG waveforms of other subjects.

In another embodiment, the NN processing device 2100 may determine a heart rate, e.g. from a high frequency component of the PPG signal or systolic and diastolic points of the PPG signal. In addition, the NN processing device 2100 may determine a low frequency component of a PPG signal to obtain a respiration rate. In another embodiment, characteristic features of the PPG waveform, such as amplitudes and phases of cardiac components, may be extracted and used to train the neural network to determine a blood pressure. See, e.g., Xing X, Sun M., "Optical blood pressure estimation with photoplethysmography and FFT-based neural networks." Biomedical Optics Express. 2016; 7(8):3007-3020, which is hereby incorporated by reference herein.

Figure 25:
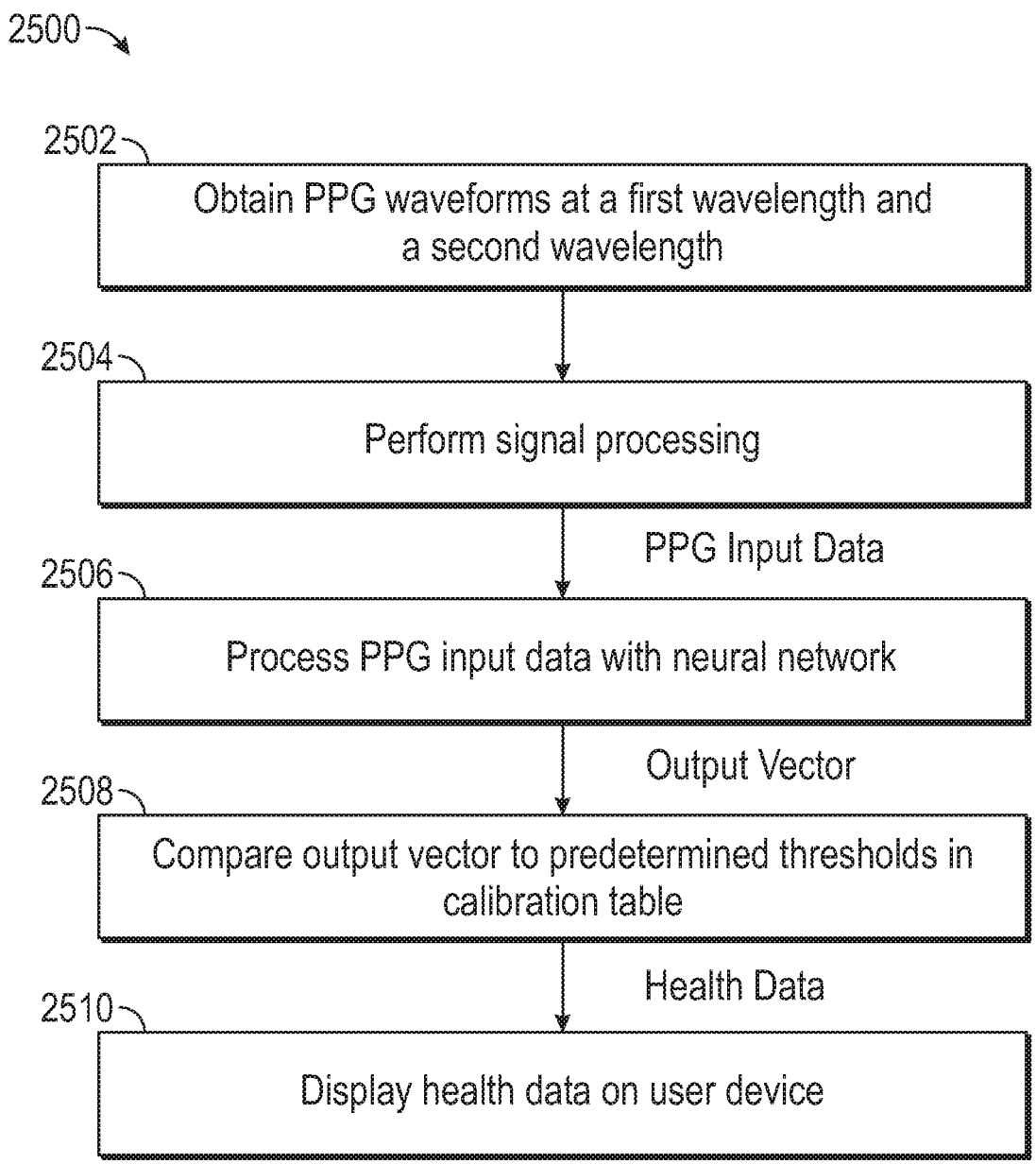
FIG. 25 illustrates a logical flow diagram of an embodiment of a method for generating health data.

FIG. 25 illustrates a logical flow diagram of an embodiment of a method 2500 for generating health data. PPG waveforms are obtained using a biosensor or non-contact camera at 2502. The PPG waveforms preferably include a first spectral response at a first wavelength with a high absorption coefficient for a target substance and a second spectral response at a second wavelength with a lower absorption coefficient for the target substance. For example, 880 nm or 940 nm (+/−20 nm) or other IR wavelengths generally have a low absorption coefficient for blood and blood substances. Thus, the second wavelength may include 880 nm or 940 nm (+/−20 nm) or other IR wavelengths. The first wavelength varies depending on the target substance, as described herein. In general, the first wavelength with a high absorption coefficient for a target substance has at least a 50% higher intensity than the second spectral response at the second wavelength with a lower absorption coefficient for the target substance.

Signal processing is performed on the PPG waveforms to generate PPG input data at 2504. The PPG input data is formatted into the input vector 2102 and processed by a neural network processing device to generate an output vector 2104 at 2506. The processing of the PPG input data may be performed by a biosensor, user device or central server. The output vector 2104 may be compared to predetermined thresholds in a calibration table at 2508. The calibration table may include various adjustments to the data based on patient information, such as age, weight, male/female, pre-existing conditions, etc. The health data is then displayed on a user device 2510.

Figure 26:
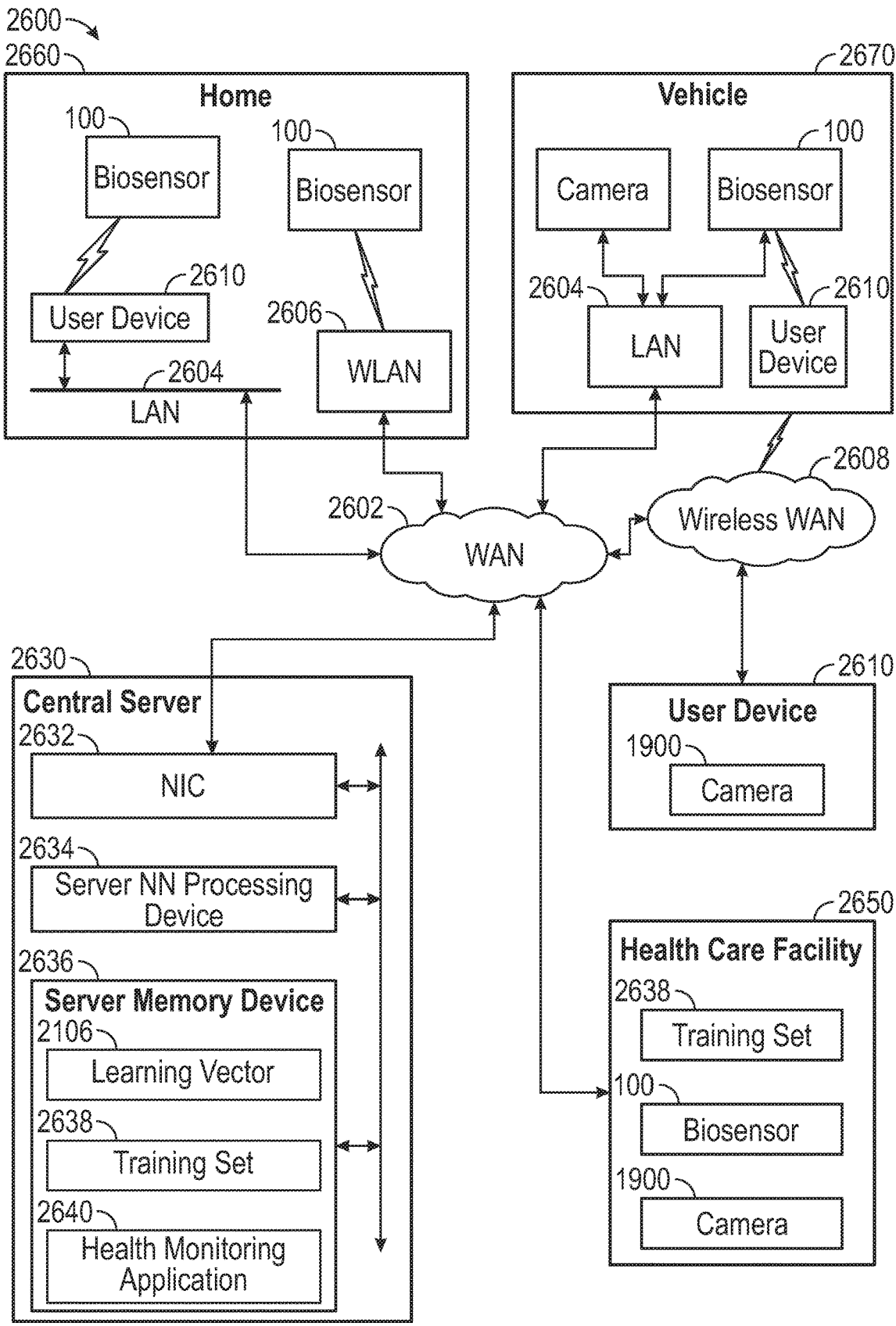
FIG. 26 illustrates a schematic block diagram of an embodiment of an example network for monitoring health data.

FIG. 26 illustrates a schematic block diagram of an embodiment of an example network 2600 for monitoring health data. The network 2600 may include a combination of one or more networks that are communicatively coupled, e.g., such as a wide area network (WAN) 2602, a wired local area network (LAN) 2604, a wireless local area network (WLAN) 2606, or a wireless wide area network (WAN) 2608. The wireless WAN 2608 may include, for example, a 3G or 4G cellular network, a GSM network, a WIMAX network, an EDGE network, a GERAN network, etc. or a satellite network or a combination thereof. The WAN 2602 includes, e.g. the Internet, service provider network, other type of WAN, or a combination of one or more thereof. The LAN 2604 and the WLANs 2606 may operate inside a home 2016, an enterprise environment, such as a health care facility, commercial building, apartment building, school, park, etc. or in a vehicle.

The biosensor 100 may communicate with or be incorporated in one or more user devices 2610, such as a smart phone, laptop, desktop, smart tablet, smart watch, activity monitoring bracelet, earpiece, button, finger attachment, or any other electronic device. In one aspect, the user device 2610 or biosensor 100 may communicate the health data to a health care facility 2650, such as a doctor's office, hospital, etc. The user device 2610 or biosensor 100 may communicate with a vehicle 2670 or a home network 2660. For example, a camera 1900 or biosensor 100 may be incorporated into a vehicle 2670 for generation of PPG input data.

The biosensors 100 and/or user devices 2610 are communicatively coupled to a central server 2630 by the network 2600. The central server 2630 may include a plurality of devices, servers, and/or memory devices in one or more geographic regions. The central server 2630 includes, e.g., a network interface card (NIC) 2632, a server neural network (NN) processing circuit 2634, and a server memory device 2636. The network interface circuit (NIC) 2632 includes an interface for wireless and/or wired network communications with one or more of the exemplary networks in the network 2600. The network interface circuit 2632 may also include authentication capability that provides authentication prior to allowing access to some or all of the resources of the central server 2630. The network interface circuit 2632 may also include firewall, gateway and proxy server functions.

The memory device 2636 is a non-transitory, processor readable medium that stores instructions which when executed by the server NN processing circuit 2634, causes the server processing circuit 2634 to perform one or more functions described herein. In an embodiment, the memory device 2636 stores a learning vector 2106 and a training set 2638.

The central server 1200 includes a health monitoring application 2640. The health monitoring application 2640 is operable to communicate with the biosensors 100 and/or user devices 2010. The health monitoring application 2640 may be a web-based application supported by the central server 2630. For example, the central server 2630 may include a web server and support the health monitoring application 2640 via a website. In another embodiment, the health monitoring application 2640 is a stand-alone application that is downloaded to the user devices 2610 and is operable on the user devices 2610 without access to the central server 2630 or only needs to accesses the central server 2630 for additional information and updates.

In an embodiment, the central server 2630 includes the NN processing device 2100. The biosensors 100 or user devices 2610 communicate PPG input data and/or patient data to the central server 2630 for processing and generation of the output vector 2104 including the health data. The health data is then transmitted over the network 2600 to the user device 2610 or biosensor 100 for display. In another embodiment, the biosensors 100 or user devices 2610 include the NN processing device 2100 and determine the health data using the PPG input data/patient data. The output vector 2104 or health data is then transmitted to the central server 2630.

In an embodiment, the central server 2630 determines the learning vector 2106 from a training set 2638. For example, the health monitoring application 2640 may periodically obtain clinical data from the health care facility 2650 or other sources, such as PPG waveforms along with health data, such as heart rate, blood pressure, respiration rate, oxygen saturation levels ($SpO_2$, $SaO_2$), blood levels of various substances (NO, glucose, blood alcohol, liver enzymes, creatinine, electrolytes, or medication dosages or blood concentration levels of other relevant substances). The central server 2630 may also receive data for updating the training set from the biosensors 100 or user devices 2610. The health monitoring application 2640 then updates the training set 2638 and processes the updated training set to generate an updated learning vector 2106. The central server 2630 then transmits the updated learning vector 2106 to the user devices 2610 and/or biosensors 100 including a NN processing device 2100.

Thus, in an embodiment, the training set 2638 is continually updated, e.g. from clinical data and user input. As the training set is updated, the learning vector 2106 may also be periodically updated (such as hourly, daily, weekly, etc.). The updated learning vector may then be transmitted to and configured on the neural network processing devices 2100. In addition, a user may update a learning vector on a personal user device based on their unique measurements of health data and PPG signals.

Figure 27:
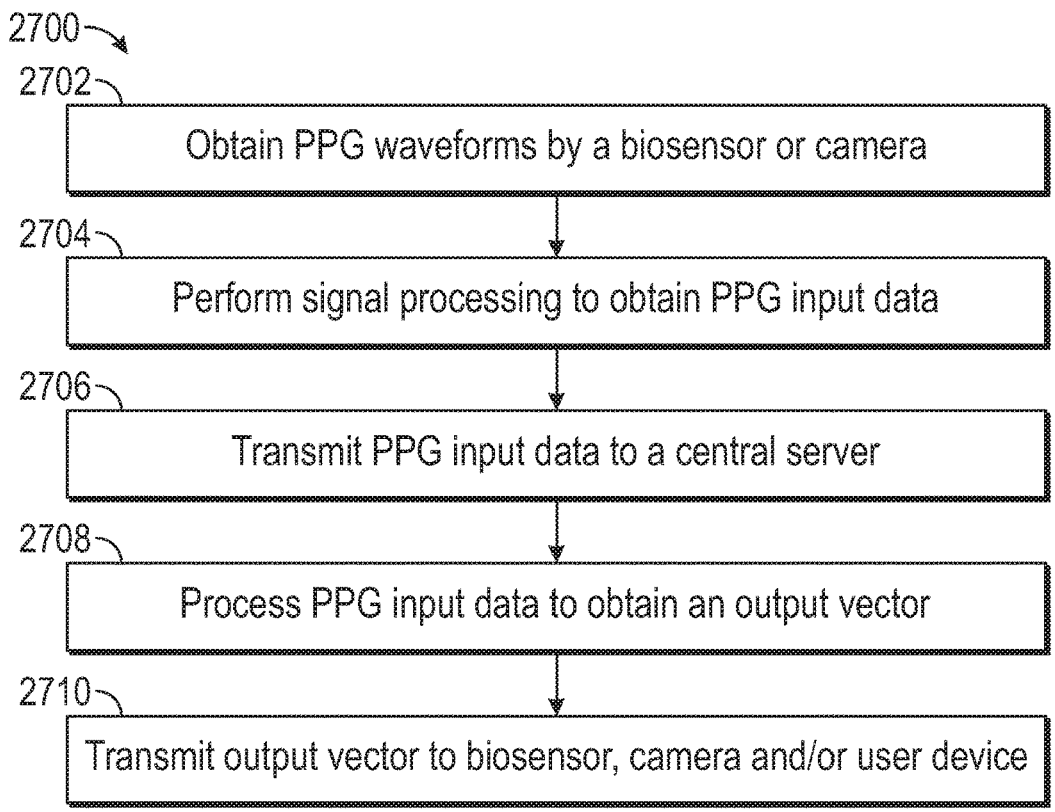
FIG. 27 illustrates a logical flow diagram of an embodiment of a method for generating health data by a central server.

FIG. 27 illustrates a logical flow diagram of an embodiment of a method 2700 for generating health data by a central server 2630. PPG waveforms are obtained by a biosensor 100 or a non-contact camera 1900. The biosensor 100 or non-contact camera 1900 may be incorporated in a user device 2610 or communicate with a user device 2610. Signal processing is performed on the PPG waveforms to generate PPG input data at 2704. The PPG input data is transmitted to a central server 2630 over a network 2600 at 2706. The central server 2630 processes the PPG input data using a server NN processing device 2634 to obtain an output vector 2104 including health data at 2708. The health data or output vector is transmitted to a biosensor 100 and/or user device 2610 for display to a user at 2710.

Figure 28:
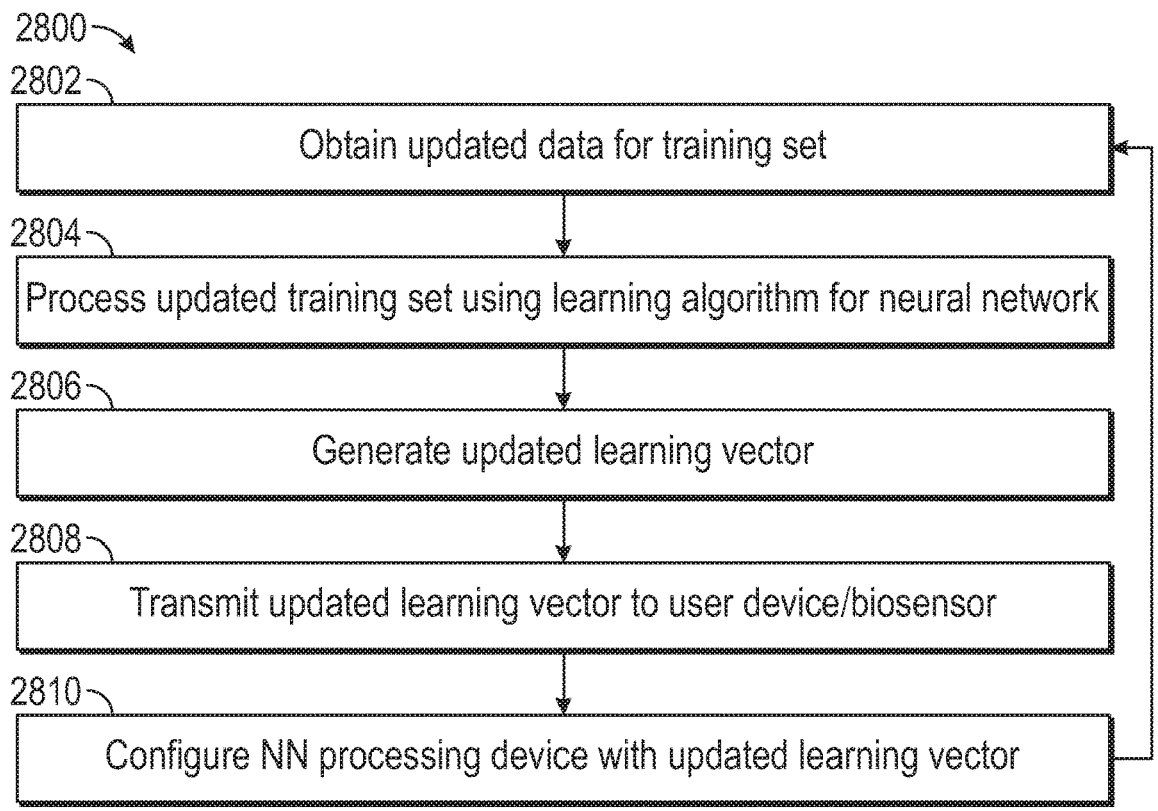
FIG. 28 illustrates a logical flow diagram of an embodiment of a method for generating health data by a central server.

FIG. 28 illustrates a logical flow diagram of an embodiment of a method 2700 for generating health data by a central server 2630. The central server 2630 continually updates the training set 2638 as it receives additional data. For example, updated data may be obtained for the training set at 2802, from clinical studies, a health care facility, physician office, or other sources. The updated data includes, e.g., PPG waveforms measured along with health data, such as heart rate, blood pressure, respiration rate, oxygen saturation levels, blood levels of various substances (NO, glucose, blood alcohol, liver enzymes, creatinine, electrolytes, or medication dosages or blood concentration levels of other relevant substances). The health data is obtained using other known methods, such as blood tests, ECG, blood pressure cuff, etc.

The central server 2630 may also receive data for updating the training set from the biosensors 100 or user devices 2610. For example, a user may obtain a glucose level using a finger prick and test strip. The glucose reading is input by the user and a PPG waveform measured. A personal physician may also provide health data obtained at a yearly physical or other doctor visit. This data may be collected over a day, week, or month to personally configure a training set for the user. This data may also be included in a global training set used to generate a learning vector 2106 for other users.

The updated training set is processing using a learning algorithm for a neural network at 2804. An updated learning vector 2106 is generated at 2806 including processing parameters for a NN processing device 2100. The updated learning vector 2808 is transmitted to a user device 2610 or biosensor 100 including the NN processing device 2100 at 2808. The NN processing device 2100 is configured using the updated learning vector/processing parameters at 2810. This process of updating the training set and learning vector may continue with periodic updates of the learning vector generated hourly, daily, weekly or monthly.

Figure 29:
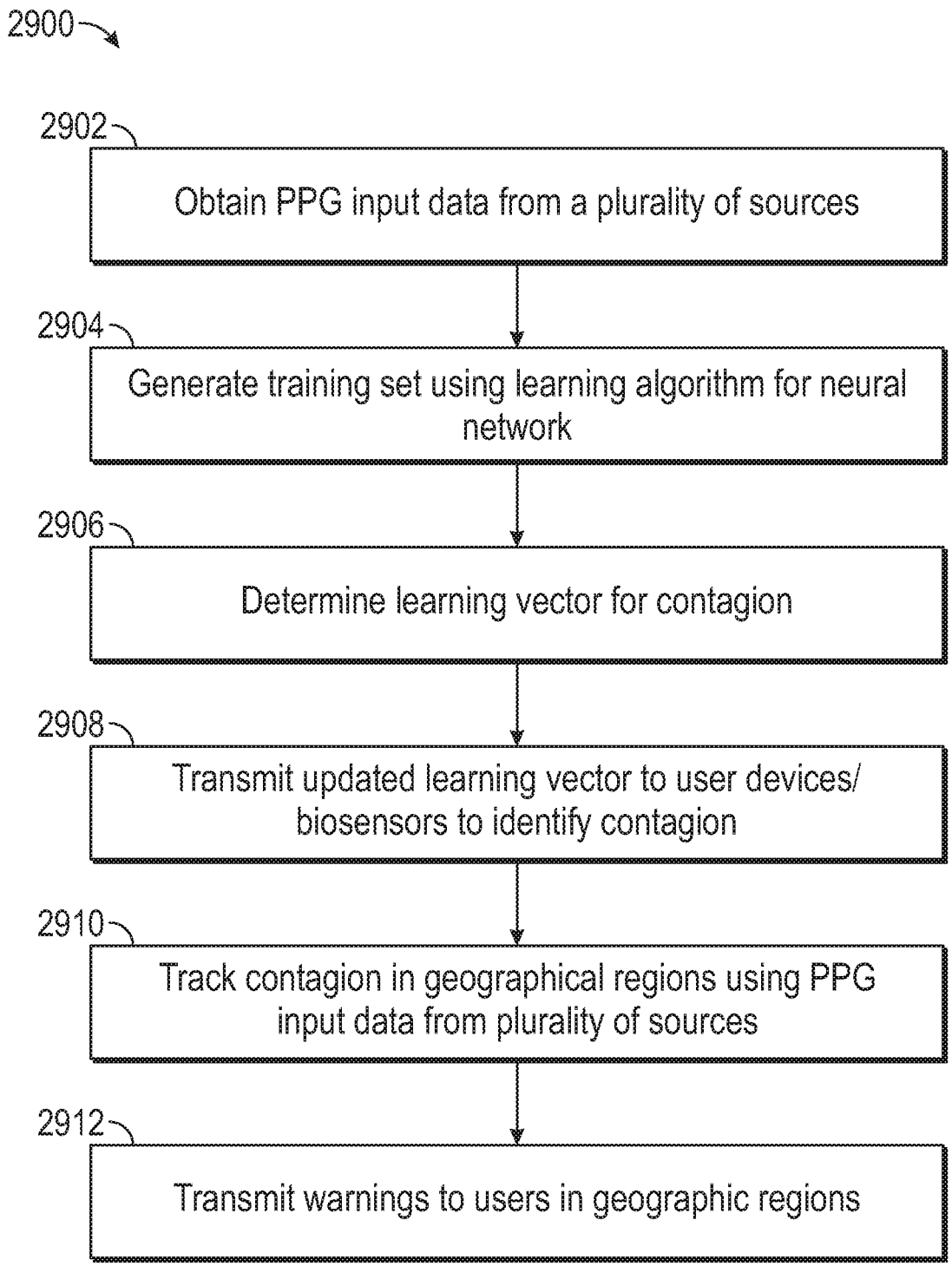
FIG. 29 illustrates a logical flow diagram of an embodiment of a method for tracking public health information by a central service.

FIG. 29 illustrates a logical flow diagram of an embodiment of a method 2900 for tracking public health information by a central service. For example, the Center for Disease Control (CDC) tracks contagions (Hepatitis A, flu strains, Malaria, Yellow Fever, Measles, Mumps, Zika virus, etc.), poisonings (such as *Salmonella* outbreaks), food safety recalls, etc. The CDC may then issue a watch or alert when a public safety concern is identified.

In an embodiment, such a service may include one or more central servers 2630 to identify and track public health information from PPG input data. The PPG input data is received from a plurality of users over a wide geographic region. Unknown contagions or substances may be identified from the PPG input data of users. A potential diagnosis may be transmitted to the user. An alert or warning may be generated in regions of infection or at potential risk.

PPG input data and corresponding patient data are received from a plurality of sources at 2902. For example, the information may be received from user devices, sensors, health care facilities, etc. When the contagion/substance is new or not yet known, the central server 2630 may generate a training set using a learning algorithm for a neural network at 2904. The central server 2630 then determines a learning vector for the contagion. When the contagion is known, the central server 2630 may determine an updated learning vector. The learning vector may be transmitted to other user devices and biosensors such that the other devices may identify the contagion at 2908. The central server 2630 may continue to receive PPG input data and corresponding patient data and analyze the data for the contagion. The central server 2630 may thus track the contagion in users and geographical regions using the PPG input data from the plurality of sources at 2910. The central server 2630 may transmit warnings for individual users, groups or geographic regions at 2912.

Figure 30:
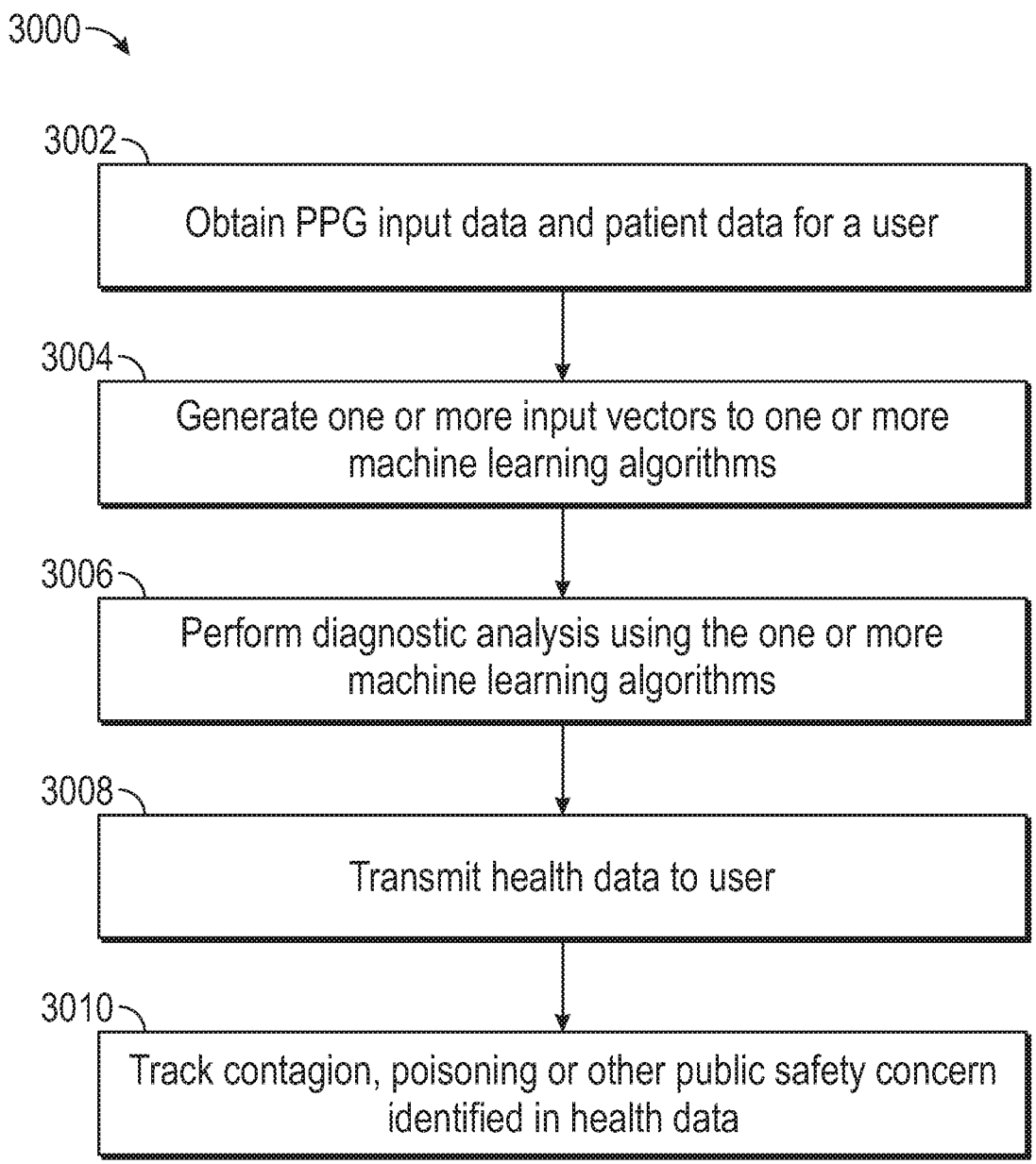
FIG. 30 illustrates a logical flow diagram of an embodiment of a method 3000 for monitoring health data of a user.

FIG. 30 illustrates a logical flow diagram of an embodiment of a method 3000 for monitoring health data of a user. PPG input data and patient data may be periodically monitored for a user at 3002. For example, PPG input data of a user may be analyzed hourly, daily, weekly or monthly. One or more input vectors may be generated for one or more machine learning algorithms at 2004. The one or more machine learning algorithms generate output vectors including health data of the user. The health data may include blood analytic tests, infection tests, etc. and potential warnings and alerts. The health data is transmitted to a user device for display at 3008. The health data may also be transmitted to a central server 2630 to track contagions or other public safety concerns identified in health data at 3010.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A device, comprising:
    an optical circuit including:
        a plurality of light emitting diodes configured to emit light at least at a first wavelength in a range of 370 nm to 410 nm and at a second wavelength equal to or greater than 660 nm;
        at least one photodetector configured to detect photoplethysmography (PPG) signals in response to pulsating blood flow, wherein the PPG signals include a first spectral response obtained from light reflected at the first wavelength from skin tissue of a patient and a second spectral response obtained from light reflected at the second wavelength from the skin tissue of the patient;
    a signal processing circuit configured to generate PPG input data using the first spectral response at the first wavelength in a range of 370 nm to 410 nm and the second spectral response at the second wavelength equal to or greater than 660 nm; and
    a neural network processing device implementing a machine learning algorithm, wherein one or more parameters of the machine learning algorithm are determined using a training set, wherein the training set includes training PPG input data obtained from a healthy population and corresponding known glucose levels from the healthy population, wherein the training PPG input data includes spectral responses at the first wavelength and at the second wavelength from the healthy population and wherein the neural network processing device is configured to:
        determine a glucose level in blood flow of the patient from the PPG input data including the first spectral response at the first wavelength and the second spectral response at the second wavelength.

2. The device of claim 1, wherein the second wavelength is in one of: a visible range or an infrared (IR) range.

3. The device of claim 1, wherein the PPG input data includes:
    a value $L_{\lambda 1}$ generated using the first spectral response, wherein the value $L_{\lambda 1}$ isolates the first spectral response due to pulsating blood flow; and
    a value $L_{\lambda 2}$ generated using the second spectral response, wherein the value $L_{\lambda 2}$ isolates the second spectral response due to pulsating blood flow.

4. The device of claim 3, wherein the PPG input data further includes:
    a value $R_{\lambda 1, \lambda 2}$ obtained from a ratio of the value $L_{\lambda 1}$ and the value $L_{\lambda 2}$.

5. The device of claim 1, wherein the PPG input data includes:
    a first AC component signal $I_{AC}$ generated using the first spectral response; or
    a second AC component signal $I_{AC}$ generated using the second spectral response.

6. The device of claim 1, wherein the PPG input data includes:
    a plurality of systolic points and diastolic points generated using the first spectral response; and
    a plurality of systolic points and diastolic points generated using the second spectral response.

7. The device of claim 1, wherein the PPG signals are generated by at least one of: a PPG circuit or a non-contact camera.

8. The device of claim 1, wherein the neural network processing device is further configured to:
    periodically receive an updated learning vector, wherein the updated learning vector is generated from an updated training set, wherein the updated training set includes updated PPG input data obtained using updated PPG signals at the first wavelength and at the second wavelength and corresponding known glucose concentration levels; and
    reconfigure one or more parameters of the machine learning algorithm for determining the glucose level in blood flow of the patient using the updated learning vector.

9. The device of claim 1, wherein the device is implemented within a user device or is configured to communicate with a user device.

10. A device, comprising:
    a signal processing circuit configured to:
    receive photoplethysmography (PPG) signals, wherein the PPG signals include a first spectral response obtained from light at a first wavelength reflected from skin tissue of a patient and a second spectral response obtained from light reflected at a second wavelength reflected from skin tissue of the patient, wherein the first wavelength is between 370 nm and 410 nm and wherein the second wavelength is equal to or greater than 660 nm;

generate PPG input data using the first spectral response obtained from light reflected at the first wavelength and the second spectral response obtained from light reflected at the second wavelength; and a neural network processing device configured to:

pre-configure one or more parameters using a learning vector generated from a training set, wherein the training set includes additional PPG input data obtained from a healthy population and corresponding known nitric oxide (NO) levels, wherein the additional PPG input data includes additional spectral responses at the first wavelength and at the second wavelength; and determine an NO level in blood flow from the first spectral response obtained from light reflected at the first wavelength and the second spectral response obtained from light reflected at the second wavelength.

11. The device of claim 10, wherein the second wavelength includes a wavelength in the IR range.

12. The device of claim 10, wherein the first wavelength is 390 nm or 395 nm.

13. The device of claim 10, wherein the signal processing module is configured to generate the PPG input data using the first spectral response and the second spectral response by generating characteristic features related to the shape of the PPG waveform from each of the first spectral response and the second spectral response.

14. The device of claim 13, wherein the signal processing module is configured to generate PPG input data using the first spectral response and the second spectral response by generating from each of the first spectral response and the second spectral response;

one or more of: a pulse shape, average distance between pulses, variance, instant energy information, or energy variance.

15. The device of claim 10, wherein the neural network processing device is further configured to correlate one or more parameters obtained from at least one of the first spectral response and the second spectral response to an oxygen saturation level in blood flow.

16. The device of claim 15, wherein the neural network processing device is further configured to correlate the one or more parameters obtained from the first spectral response and the second spectral response to the oxygen saturation level in blood flow.

17. The device of claim 10, wherein the neural network processing device is further configured to correlate one or more parameters obtained from at least one of the first spectral response and the second spectral response to a glucose level in blood flow.

18. A device, comprising:

a signal processing circuit including a plurality of light emitting diodes and at least one photodetector configured to:

obtain photoplethysmography (PPG) signals at a first wavelength from skin tissue of a patient and at a second wavelength from skin tissue of the patient, wherein the first wavelength is in a range of 370 nm-410 nm and wherein the second wavelength is in a visible or an infrared (IR) range;

generate PPG input data using the PPG signals obtained from the patient at the first wavelength in the range of 370 nm-410 nm and at the second wavelength in the visible or the IR range; and a neural network processing device configured to:

obtain one or more parameters generated from a training set, wherein the training set includes PPG signals obtained from a healthy population at the first wavelength in a range of 370 nm to 410 nm and at the second wavelength in the visible or the IR range and corresponding known glucose levels obtained from the healthy population;

receive the PPG input data; and determine a glucose level in blood flow of the patient from the PPG signals obtained from the patient at the first wavelength in the range of 370 nm to 410 nm and at the second wavelength in the visible or the IR range.

19. The device of claim 18, wherein the second wavelength includes one of: 660 nm, 880 nm, 940 nm, or 1050 nm.

20. The device of claim 18, wherein the neural network processing device is further configured to determine an NO level in the blood flow from the PPG input data.

21. The device of claim 18, wherein the signal processing module is configured to generate the PPG input data from the PPG signals by generating one or more of: a pulse shape, average distance between pulses, variance, instant energy information, or energy variance.

22. The device of claim 18, wherein the signal processing module is configured to generate the PPG input data from the PPG signals by generating characteristic features related to a shape of waveforms of the PPG signals.

23. The device of claim 18, wherein the neural network processing device is further configured to:

periodically receive an updated learning vector, wherein the updated learning vector is generated from an updated training set, wherein the updated training set includes additional PPG input data obtained using additional PPG signals at the first wavelength in the range of 370 nm-410 nm and at the second wavelength in the visible or IR range and known glucose concentration levels; and reconfigure one or more parameters for generating the glucose level in blood flow of the patient from the PPG input data.

24. The device of claim 18, wherein the device is implemented within a user device or is configured to communicate with a user device.

* * * * *